US008097721B2

(12) United States Patent
Armstrong et al.

(10) Patent No.: US 8,097,721 B2
(45) Date of Patent: Jan. 17, 2012

(54) HIGH STABILITY POLYIONIC LIQUID SALTS

(75) Inventors: Daniel W. Armstrong, Arlington, TX (US); Junmin Huang, Piscataway, NJ (US)

(73) Assignee: Sigma-Aldrich Co. LLC, St. Louis, MO (US)

(*) Notice: Subject to any disclaimer, the term of this patent is extended or adjusted under 35 U.S.C. 154(b) by 877 days.

(21) Appl. No.: 12/023,468

(22) Filed: Jan. 31, 2008

(65) Prior Publication Data

US 2008/0210858 A1   Sep. 4, 2008

Related U.S. Application Data

(60) Provisional application No. 60/898,843, filed on Jan. 31, 2007.

(51) Int. Cl.
*C07D 243/00* (2006.01)
*C07D 403/00* (2006.01)
*C07D 207/00* (2006.01)
*C07C 211/00* (2006.01)
*C07F 9/02* (2006.01)

(52) U.S. Cl. ............... 540/567; 548/313.7; 548/524; 564/305; 568/17

(58) Field of Classification Search ............... 540/567; 548/313.7, 524; 564/305; 568/17
See application file for complete search history.

(56) References Cited

U.S. PATENT DOCUMENTS

| | | | | |
|---|---|---|---|---|
| 2,500,110 | A | 3/1950 | Allen et al. | 260/290 |
| 2,865,964 | A | 12/1958 | Dornfeld et al. | 260/606.5 |
| 4,557,919 | A | 12/1985 | Sumitani et al. | 423/329 |
| 5,484,556 | A | 1/1996 | Akhavan-Tafti et al. | 252/700 |
| 5,620,595 | A | 4/1997 | Austin et al. | 210/169 |
| 5,827,602 | A | 10/1998 | Koch et al. | 429/194 |
| 6,531,241 | B1 | 3/2003 | McEwen | 429/46 |
| 6,900,313 | B2 | 5/2005 | Wasserscheid et al. | 544/59 |
| 2006/0014955 | A1 | 1/2006 | Armstrong et al. | 546/2 |
| 2006/0025598 | A1 | 2/2006 | Armstrong et al. | 548/101 |
| 2008/0027231 | A1 | 1/2008 | Armstrong et al. | 548/313.7 |

FOREIGN PATENT DOCUMENTS

| | | |
|---|---|---|
| DE | 39618 | 6/1965 |
| DE | 1204226 | 11/1965 |
| DE | 2031213 | 12/1971 |
| DE | 3333124 | 5/1985 |
| EP | 0137241 A1 | 4/1985 |
| GB | 633158 | 12/1949 |
| GB | 711654 | 7/1954 |
| GB | 821242 | 10/1959 |
| GB | 1344839 | 6/1971 |
| JP | 59190213 | 10/1984 |
| JP | 08301703 | 11/1996 |
| JP | 2003/017148 | 1/2003 |
| SU | 1727789 | 7/1965 |
| WO | WO 91/04668 A | 4/1991 |
| WO | WO 9104668 | 4/1991 |
| WO | WO01/85093 | 11/2001 |
| WO | WO 2005/054241 | 6/2005 |
| WO | WO2006/012513 A2 | 2/2006 |
| WO | WO 2007/124397 | 11/2007 |
| WO | WO 2008/110007 | 9/2008 |

OTHER PUBLICATIONS

[Sunggoo, Yun. Molecular Recognition of Fluoride Anion: Benzene-Based Tripodal Imidazolium Receptor. J. Org. Chem. 2003, 68, 2467-2470.]*
[Zhao, Yuanhong. Suzuki cross-coupling mediated by tetradentate N-heterocyclic carbene (NHC)-palladium complexes in an environmentally benign solvent. Org. Biomol. Chem., 2003, 1, 1643-1646.]*
[Hu, Xile. Copper Complexes of Nitrogen-Anchored Tripodal N-Heterocyclic Carbene Ligands. J. Am. Chem. Soc. 2003, 125, 12237-12245.]*
Abraham MH, et al., *XVII. The Characterisation of 24 Gas-Liquid Chromatographic Stationary Phases Studied by Poole and Co-Workers, Including Molten Salts, and Evaluation of Solute-Stationary Phase Interactions*, J. Chromatogr. 587:229-236 (1991).
Abraham MH, *Scales of Solute Hydrogen-Bonding: Their Construction and Application to Physicochemical and Biochemical Processes*, Chem. Soc. Rev. 22:73-83 (1993).
Anderson JL, et al., *Characterizing Ionic Liquids on the Basis of Multiple Solvation Interactions*, J. Am. Chem. Soc. 124:14247-14254 (2002).
Anderson JL, et al., *High-Stability Ionic Liquids. A New Class of Stationary Phases for Gas Chromatography*, Anal. Chem. 75:4851-4858 (2003).
Anderson JL, et al., *Structure and Properties of High Stability Geminal Dicationic Ionic Liquids*, J. Am. Chem. Soc. 127:593-604 (2005).
Anderson JL, et al., *Surfactant Solvation Effects and Micelle Formation in Ionic Liquids*, J. Am. Chem. Commun. 2444-2445 (2003).
Arimura T, et al., *Template Effects on Calixarene Conformations Through Host-Guest Type Interactions*, Tetrahedron Lett. 30(19):2563-2566 (1989).
Armstrong DW, et al., *Examination of Ionic Liquids and Their Interaction with Molecules, When Used as Stationary Phases in Gas Chromatography*, Anal. Chem. 71:3873-3876 (1999). Baranyai KJ, et al., *Thermal Degradation of Ionic Liquids at Elevated Temperatures*, Aust. J. Chem. 57:145-147 (2004).
Bitterer F, et al., "Wasserlösliche Phosphane, IV. Tertiäre Alkylphosphane mit Ammoniumgruppen in den Seitenketten—Amphiphile mit basischen P-Atomen—Water-soluble phosphanes, IV. Tertiary alkylphosphanes with ammonium groups in the side chains—amphiphiles with basic P-atoms", Chemische Bericht, 128(3):275-279 (1995).
Blessing RH, *An Empirical Correction for Absorption Anisotrophy*, Acta Crystallogr., A51:33-38 (1995).
Bondi A, *Van Der Waals Volumes and Radii*, J. Phys. Chem.. 68:441-453 (1964).
Bonhote P, et al., *Hydrophobic, Highly Conductive Ambient-Temperature Molten Salts*, Inorg. Chem. 35:1168-1178 (1996).

(Continued)

*Primary Examiner* — Rebecca Anderson
*Assistant Examiner* — Samantha Shterengarts
(74) *Attorney, Agent, or Firm* — Harness, Dickey & Pierce, P.L.C.

(57) ABSTRACT

Polyionic liquid salts are provided comprising polycationic or polyanionic molecules. Further provided are solvents comprising one or more polyionic liquid salts, and the use of such polyionic liquid salts as stationary phases in gas chromatography, and as a reagent in electrospray ionization-mass spectrometry (ESI-MS).

12 Claims, 3 Drawing Sheets

OTHER PUBLICATIONS

Bouche J and Verzele M, *A Static Coating Procedure for Glass Capillary Columns*, J. Gas Chromatogr. 6:501-505 (1968).

Boxall DL and Osteryoung RA, *Switching Potentials and Conductivity of Polypyrrole Films Prepared in the Ionic Liquid 1-Butyl-3-Methylimidazolium Hexafluorophosphate*, J. Electrochem. Soc. 151(2):E41-E45 (2004).

Brophy JJ, et al.: "*The cleavage of bisphosphonium salts by sodium hydride*" Chemical Communications, 15:531-532 (1966).

Bryce MR, *Recent Progress on Conducting Organic Charge-Transfer Salts*, Chem. Soc. Rev. 20:355-390 (1991).

Cadena C, et al., *Why is $CO_2$ SO Soluble in Imidazolium-Based Ionic Liquids?*, J. Am. Chem. Soc. 126:5300-5308 (2004).

Carda-Broch S, et al., *Solvent Properties of the 1-Butyl-3-Methylimidazolium Hexafluorophosphate Ionic Liquid*, Anal. Bioanal. Chem. 375:191-199 (2003).

Carter E, et al., *Sweet Success: Ionic Liquids Derived from Non-Nutritive Sweetenters*, Anal. Chem. Commun. 630-631 (2004).

Chellappan K, et al., *A Calix[4]Imidazolium[2]Pyridine as an Anion Receptor*, Angew. Chem. Int. Ed. 44(19):2899-2903 (2005).

Dearden JC, *The QSAR Prediction of Melting Point, a Property of Environmental Relevance*, Sci. Total Environ. 59:109-110 (1991).

Dzyuba SV and Bartsch RA, *Influence of Structural Variations in 1-Alkyl(aralkyl)-3-Methylimidazolium Hexafluorophosphates and Bis(trifluoromethylsulfonyl)Imides on Physical Properties of the Ionic Liquids*, Chem. Phys. Chem. 3:161-166 (2002).

Earle MJ, et al., *Paradigm Confirmed: The First Use of Ionic Liquids to Dramatically Influence the Outcome of Chemical Reactions*, Org. Lett. 6(5):707-710 (2004).

Eike DM, et al., *Predicting Melting Points of Quaternary Ammonium Ionic Liquids*, Green Chem. 5:323-328 (2003).

Forsyth SA, et al., *Ionic Liquids-An Overview*, Aust. J. Chem. 57:113-119 (2004).

Fletcher KA and Pandey S, *Surfactant Aggregation Within Room-Temperature Ionic Liquid 1-Ethyl-3-Methylimidazolium Bis(trifluoromethylsulfonyl)Imide*, Langmuir 20:33-36 (2004).

Gao H, et al., *Aqueous/Ionic Liquid Interfacial Polymerization for Preparing Polyaniline Nanoparticles*, Polymer. 45:3017-3019 (2004).

Grob K Jr., et al., *Comprehensive, Standardized Quality Test for Glass Capillary Columns*, J. Chromatogr. 156:1-20 (1978).

Grob K, et al., *Testing Capillary Gas Chromatographic Columns*, J. Chromatogr. 219:13-20 (1981).

Han X and Armstrong D, *Using Geminal Dicationic Ionic Liquids as Solvents for High-Temperature Organic Reactions*, Org. Lett. 7(19):4205-4208 (2005).

Hideg K and Hankovszky OH, *Benzazoles, III. Alkylation of Benzimidazoles*, Acta Chimica Academiae Scientarum Hungaricae 49(3):303-310 (1966).

Holbrey JD, et al., *Crystal Polymorphism in 1-Butyl-Methylimidazolium Halides: Supporting Ionic Liquid Formation by Inhibition of Crystallization*, Chem. Commun. 219:1636-1637 (2003).

Horn PE, et al., *The reactions of organic derivatives of elements capable of valency-shell expansion. Part VII. Further experiements with quaternary phosphonium salts* Journal of the Chemical Society, 1036-1040 (1963).

Howell BA, et al., *High phosphorus/bromine content compounds as polyolefin flame retardants*, Recent Advances in Flame Retardancy of Polymeric Materials, 7:119-126 (1997).

Hu X, et al., *A Bis-Carbenealkenyl Copper(I) Complex from a Tripodal Tris-Carbene Ligand*, Organometallics 22(15):3016-3018 (2003).

Hu X, et al., *Copper Complexes of Nitrogen-Anchored Tripodal N-Heterocyclic Carbene Ligands*, J. Am. Chem. Soc. 125(40):12237-12245 (2003).

Hu X, et al., *Dioxygen Activation by a Low-Valent Coblat Complex Employing a Flexible Tripodal N-Heterocyclic Carbene Ligand*, J. Am. Chem. Soc. 126(41):13464-13473 (2004).

Hu X, et al., *Group II Metal Complexes of N-Heterocyclic Carbene Ligands: Nature of the Metal-Carbene Bond*, Organometallics 23(4):755-764 (2004).

Hu X, et al., *Silver Complexes of a Novel Tripodal N-Heterocyclic Carbene Ligand: Evidence for Significant Metal-Carbene π-Interaction*, Organometallics 22(4):612-614 (2003).

Hu X, et al., *Terminal Cobalt(III) Imido Complexes Supported by Tris(Carbene) Ligands: Imido Insertion into the Cobalt-Carbene Bond*, J. Am. Chem. Soc. 126(50):16322-16323 (2004).

Ilies MA, et al., *Lipophilic Pyrylium Salts in the Synthesis of Efficient Pyridinium-Based Cationic Lipids, Gemini Surfactants, and Lipophilic Oligomers for Gene Delivery*, J. Med. Chem. 49(13):3872-3887 (2006).

Itoh H, et al., *Synthesis of Gold Nanoparticles Modified with Ionic liquid Based on the Imidazolium Cation*, J. Am. Chem. Soc. 126:3026-3027 (2004).

Jin CM, et al., *Polyethylene Glycol Functionalized Dicationic Ionic Liquids With Alkyl or Polyfluoroalkyl Substituents as High Temperature Lubricants*, J. Master. Chem. 16:1529-1535 (2006).

Kaar JL, et al., *Impact of Ionic Liquid Physical Properties on Lipase Activity and Stability*, J. Am. Chem. Soc. 125:4125-4131 (2003).

Katritzky AR, et al., *Correlation of the Melting Points of Potential Ionic Liquids (Imidazolium Bromides and Benzimidazolium Bromides) Using the CODESSA Program*, J. Chem. Inf. Comput. Sci. 42:225-231 (2002).

Kawahara S and Uchimaru T, *One-Pot Preparation of o-Xylylene Diamine and its Related Amines*, Zfitschrift Fuer Naturforschung, B: Chemical Sciences, 55(10):985-987 (2000).

Kim H and Kang J, *Iodide Selective Fluorescent Anion Receptor with Two Methylene Bridged Bis-Imidazolium Rings on Naphthalene*, Tetrahedron Lett. 46(33):5443-5445 (2005).

Kostyanovskii RG, et al., "*Geminal systems. 19. Reactions of aminomethylphosphines with electrophilic reagents*" Bulletin of the Academy of Sciences of the USSR, Division of Chemical Sciences, 31(7):1433-1441 (1982).

Kwon JY, et al., *Fluorescent GTP-Sensing in Aqueous Solution of Physiological pH*, J. Am. Chem. Soc. 126(29):8892-8893 (2004).

Law G and Watson PR, *Surface Tension Measurements of N-Alkylimidazolium Ionic Liquids*, Langmuir 17:6138-6141 (2001).

Lane ES, et al., *Quaternary ammonium nitrates. Part II. Reaction of nitratoalkyl ethers, amines, amides, and urethanes with tertiary amines and related compounds* J. Chem. Soc. 2006-2010 (1956).

Lee JK and Kim M-J, *Ionic Liquid-Coated Enzyme for Biocatalysis in Organic Solvent*, J. Org. Chem 67:6845-6847 (2002).

Liu JF, et al., *Disposable Ionic Liquid Coating for Headspace Solid-Phase Microextraction of Benzene, Toluene, Ethylbenzene, and Xylenes in Paints Followed by Gas Chromatography-Flame Ionization Detection*, J. Chromatogr. A 1066(1-2):27-32 (2005).

Liu J, et al., *Imidazolylidene Carbene Ligated Palladium Catalysis of the Heck Reaction in the Presence of Air*, Org. Biomol. Chem. 1(18):3227-3231 (2003).

Liu et al., *Determination of formaldehyde in shiitake mushroom by ionic liquid-based liquid-phase microextraction coupled with liquid chromatography*, Talanta 65(3):705-709 (2005).

Löhr HG, et al., *Organylammonium-Wirtsubstanzen als vielseitige Clathratbildner*, Chem. Ber. 117(4):1487-1496 (1984).

Lord H and Pawliszyn J, *Evolution of Solid-Phase Mircoextraction Technology*, J. Chromatogr. A 885:153-193 (2000).

Lundberg KL, et al., "*Gem-Dibasic ligands with phosphorus, sulphur and nitrogen sites, and some borane derivatives*" Inorganic Chemistry, 8(6):1336-1340 (1969).

Luo H, et al., *Extraction of Cesium Ions from Aqueous Solutions Using Calix[4]arene-bis(tertoctylbenxo-crown-6) In Ionic Liquids*, Anal. Chem. 76:3078-3083 (2004).

Mamane V, et al., *Palladium-Catalyzed Cross-Coupling Reaction of a Chiral Ferrocenyl Zinc Reagent with Aromatic Bromides: Application to the Design of Chiral Octupoles for Second Harmonic Generation*, Synthesis 3:455-467 (2003).

Marcilla R, et al., *Tuning the Solubility of Polymerized Ionic Liquids by Simple Anion-Exchange Reactions*, J. Polym. Sci. Part A: Polym. Chem. 42:208-212 (2004).

Martinelango PK, et al., *Gas-Phase Ion Association Provides Increased Selectivity and Sensitivity for Measuring Perchlorate by Mass Spectrometry*, Anal. Chem. 77:4829-4835 (2005).

Mas-Marzá E, et al., *Carbene Complexes of Rhodium and Iridium from Tripodal N-Heterocyclic Carbene Ligands: Synthesis and Catalytic Properties*, Inorg. Chem. 43(6):2213-2219 (2004).

Mas-Marzá E, et al., *Synthesis and Catalytic Properties of Two Trinuclear Complexes of Rhodium and Iridium with the N-Heterocyclic Tris-carbene Ligand TIMEN$^{iPr}$*, Organometallics 24(13):3158-3162 (2005).

McCullough D, et al., *Glued Langmuir-Blodgett Bilayers from Porous Versus Nonporous Surfactants*, J. Am. Chem. Soc. 126(32):9916-9917 (2004).

Mizzoni RH, et al., *Polyamine Salts with Autonomic Blocking Properties*, J. Am. Chem. Soc. 76:2414-2417 (1954).

Molodykh ZV, et al., *Antimicrobial Activity of Ortho-Aminomethylphenols and Their Derivatives*, Pharm. Chem. J. 21(2):110-114 (1987).

Muldoon MJ and Gordon CM, *Synthesis of Gel-Type Polymer Beads from Ionic Liquid Monomers*, J. Polym. Sci. Part A: Polym Chem. 42:3865-3869 (2004).

Ngo HL, et al., *Thermal Properties of Imidazolium Ionic Liquids*, Thermochim. Acta. 357-358:97102 (2000).

Ohki A, et al., *Sensing of Poly(Styrenesulfonate)s by Polymeric Membrane Electrodes Based on Liquid Anion-Exchangers*, Bull. Chem. Soc. Jpn., 70(4):799-804 (1997).

Payagala T, et al., "*Unsymmetrical dicationic ionic liquids: Manipulation of physicochemical properties using specific structural architectures*" Chemistry of Materials, 19(24):5848-5850 (2007).

Parenty ADC, et al., *General One-Pot, Three-Step Methodology Leading to an Extended Class of N-Heterocyclic Cations: Spontaneous Nucleophilic Addition, Cyclization, and Hydride Loss*, J. Org. Chem. 69(18):5934-5946 (2004).

Patinec V, et al., *The Use of Triquaternary Alkylammonium Ions in the Synthesis of STA-5, a Magnesioaluminophosphate with the BPH Framework* Topology, Chemistry of Materials 11(9):2456-2562 (1999).

Pernak J, et al., *Synthesis and Properties of Trigeminal Tricationic Ionic Liquids*, Chem. Eur. J. 13:3106-3112 (2007).

Rehse K and Kämpfe M, *Oligotertiäre Amine and Oligoquartare Ammoniumsalze*, Archiv Der Pharmazie 322:811-815 (1989).

Remsberg et al., *Evaluation of Dicationic Reagents for Their Use in Detection of Anions Using Positive Ion Mode ESI-MS Via Gas Phase Ion Association*, Journal of the American Society for Mass Spectrometry, 19(2):261-269 (2007).

Schilf W, et al., *NMR and X-ray Investigations of Model Tris- and Bis-Pyridinium Fluoroborates*, J. Mol. Struct. 707(1-3):115-121 (2004).

Seddon KR, et al., *Viscosity and Density of 1-Alkyl-3-Methylimidazolium Ionic Liquids*, ACS Symposium Series 819:34-49 (2002).

Shinkai S, et al., *Ion Template Effects on the Conformation of Water-Soluble Calixarenes*, J. Org. Chem. 56(1):295-300 (1991).

Soukup-Hein RJ, et al., *Evaluating the Use of Tricationic Reagents for the Detection of Doubly Charged Anions in the Positive Mode by ESI-MS*, Anal. Chem.80(7):2612-2616 (2008).

Terazima M, et al., *Diffusion of a Radical from an Initiator of a Free Radical Polymerization: A Radical from AIBN*, Chem. Phys. Lett. 332:503-507 (2000).

Van Valkenburg ME, et al., *Ionic Liquids as Thermal Fluids*, Electrochemical Society Proceedings 2002-19:112-123 (2002).

Van Hook JP and Tobolsky AV, *The Thermal Decomposition of 2,2'-Azo-bis-isobutyronitrile*, J. Am. Chem. Soc. 80:779-782 (1958).

Vas G and Vekey K, *Solid-Phase Microextraction: A Powerful Sample Preparation Tool Prior to Mass Spectrometric Analysis*, J. Mass Spectrom. 39:233-254 (2004).

Vijayaraghavan R and MacFarlane DR, *Living Cationic Polymerisation of Styrene in an Ionic Liquid*, Chem Commun. 700-701 (2004).

Visser AE, et al., *Task-Specific Ionic Liquids Incorporating Novel Cations for the Coordination and Extraction of $Hg^{2+}$ and $Cd^{2+}$: Synthesis, Characterization, and Extraction Studies* Environ. Sci. Technol. 36:2523-2529 (2002).

Wasserscheid P, et al., *Ionic Liquids-Weakly-Coordinating Solvents for the Biphasic Ethylene Oligometization to α-olefins Using Cationic Ni-complexes*, J. Mol. Catal. A: Chem. 214:83-90 (2004).

Wei GT, et al., *Aqueous-Organic Phase Transfer of Gold Nanoparticles and Gold Nanorods Using an Ionic Liquid*, J. Am. Chem. Soc. 126:5036-5037 (2004).

Welton T, *Room Temperature Ionic Liquids. Solvents for Synthesis and Catalysis*, J Chem Rev. 99:2071-2083 (1999).

Wilkes JS, *Properties of Ionic Liquid Solvents for Catalysis*, J. Mol. Catal. A: Chem. 214:11-17 (2004).

Wong WWH, et al., *Tetrakis(imidazolium)Macrocyclic Receptors for Anion Binding*, Org. Biomol, Chem. 3(23):4201-4208 (2005).

Wu J, et al., *Homogeneous Acetylation of Cellulose in a New Ionic Liquid*, Biomacromolecules 5:266-268 (2004).

Zhao et al., *Suzuki Cross-Coupling Mediated by Tetradentate N-Heterocyclic Carbene (NHC)- Palladium Complexes in an Environmentally Benign Solvent*, Org. Biomol. Chem. 1(10):1643-1646 (2003).

Zhao H and Malhotra SV, *Enzymatic Resolution of Amino Acid Esters Using Ionic Liquid N-ethyl Pyridinium Trifluoroacetate*, Biotechnol. Lett. 24:1257-1260 (2002).

Zhou Y and Antonietti M, *Synthesis of Very Small $TiO_2$ Nanocrystals in a Room-Temperature Ionic Liquid and Their Self-Assembly Toward Mesoporous Spherical Aggregates*, J. Am. Chem. Soc. 125:14960-14961 (2003).

International Search Report, PCT/US2005/26036, dated Jun. 16, 2006.

International Search Report, PCT/US2008/052583, dated Mar. 25, 2009.

International Search Report, PCT/US2008/052590, dated Mar. 4, 2009.

Office Action, dated Sep. 9, 2008 issued in U.S. Appl. No. 11/177,093.

Office Action, dated Sep. 17, 2008 issued in U.S. Appl. No. 11/701,537.

Office Action, dated Sep. 22, 2008 issued in U.S. Appl. No. 11/187,389.

Office Action, dated May 6, 2009 issued in U.S. Appl. No. 11/701,537.

Office Action, dated May 8, 2009 issued in U.S. Appl. No. 11/187,389.

Office Action, dated Sep. 9, 2009 issued in U.S. Appl. No. 11/701,537.

Office Action, dated Oct. 20, 2009 issued in U.S. Appl. No. 12/331,108.

Office Action, dated Dec. 11, 2009 issued in U.S. Appl. No. 11/187,389.

Office Action, dated Mar. 11, 2010 issued in U.S. Appl. No. 11/701,537.

Anderson, et al., (2003) "High-stability ionic liquids. A new class of stationary phases for gas chromatography" Anal. Chem. 75:4851-4858.

Brune, et al. (1970) "Chlorophyllin a-catalyzed photoreduction of viologen dyes (Krasnovsky Reaction)" Archives of Biochemistry and Biophysics, 141:371-373.

Kordosky, et al. (1973) "Tetramethyldiphosphine and flexible aliphatic (dimethylphosphino) ligands" Inorganic Synthesis, vol. XIV, 14-23.

Oshikiri, et al. (2005) "Kinetic control of threading of cyclodextrins onto axle molecules" Journal of the Chemical Society, 127:12186-12187.

Rothstein, et al. (1953) "The reactions of organic derivatives of elements capable of valency-shell expansion. Part II Unsaturated quaternary phosphonium salts" 3994-4004.

Vasserman (1956) Sbornik Nauch. Rabot, Rizhskii Med. Inst., 5:23-36.

Office Action, dated Jun. 8, 2010 issued in U.S. Appl. No. 11/187,389.

Office Action, dated Jul. 26, 2010 issued in U.S. Appl. No. 11/701,537.

Office Action, dated Sep. 9, 2010 issued in U.S. Appl. No. 11/187,389.

Office Action, dated Sep. 9, 2010 issued in U.S. Appl. No. 11/701,537.

Office Action, dated Dec. 9, 2010 issued in U.S. Appl. No. 11/187,389.

Office Action, dated Feb. 8, 2011 issued in U.S. Appl. No. 11/701,537.

Office Action, dated Apr. 15, 2011 issued in U.S. Appl. No. 11/187,389.

* cited by examiner

HIGH STABILITY POLYIONIC LIQUID SALTS

This application claims priority to U.S. provisional application Ser. No. 60/898,843 filed on 31 Jan. 2007, the disclosure of which is incorporated herein by reference in its entirety.

BACKGROUND OF THE INVENTION

One of the more rapidly growing areas of chemistry research involves ionic liquids (ILs) and room temperature ionic liquids (RTILs). The wide range of possible cation and anion combinations allows for a large variety of tunable interactions and applications. The uses and applications of RTILs have traversed many areas of chemistry and even areas of biochemistry. Reported thermal stability ranges of 300° C. in some cases, their ability to solubilize a variety of disparate molecules, and the fact that ionic liquids can be synthesized that are immiscible with both water and nonpolar organic solvents further add to their usefulness. While much work involving RTILs deals with their use as "green" solvents in organic synthesis, their characterization and the understanding of their unique physico-chemical and solvation properties are important areas of ongoing investigation. Some research in the field of ionic liquids has explored their fundamental properties in hopes that it would become apparent which cation-anion combinations give rise to specific and/or desired qualities. Thus far, this approach has met with only limited success.

Early work seemed to indicate that the anionic constituents of ionic liquids may have a greater influence on their physical and chemical properties. However, this notion may be due, in part, to the fact that the ionic liquids studied contained not only a variety of different anions, but closely related, structurally similar cations. Indeed, anions such as halides possess higher hydrogen bond basicity character (Cl>Br>I) and readily hydrogen bond to generally form viscous liquids. This is not to say that only coordinating anions produce viscous liquids; it is well known that the viscosity of 1-alkyl-3-methylimidazolium ionic liquids is found to increase with increasing alkyl chain length even when paired with non-coordinating anions such as hexafluorophosphate ($PF_6^-$) and bis (trifluoromethylsulfonyl)imide ($NTf_2^-$). While the cation and its structure can certainly influence the surface tension, melting point, viscosity, density, and thermal stability as well as interact via dipolar, π-π, and eta-π interactions with dissolved molecules, its range of effects has not been studied as extensively as it has for anions.

Despite their touted stability, many of the more common ionic liquids are susceptible to chemical and thermal degradation. Recently, it was reported that when 1-butyl-3-methylimidazolium chloride (BMIM-Cl) is exposed to the atmosphere and heated, it begins to turn from a pale yellow to amber color at 120° C. When heated further, the ionic liquid begins to show obvious signs of decomposition at and above 150° C. Most recently, a new class of "high stability ionic liquids" based on bulky cations and triflate anions was introduced and it was reported that the robustness of some of the more traditional ionic liquids appears to be less than previously thought (in terms of both lower thermal stability and higher volatility). MacFarlane and co-workers reached similar conclusions via use of the 'step tangent method' for thermogravimetric analysis (TGA) to more accurately determine degradation temperatures of imidazolium-based cations. They point out that significant evolution of volatile degradation products takes place well below previously reported degradation temperatures. A maximum operating temperature parameter was proposed to provide a more appropriate estimate of thermal stability using TGA.

Techniques of solid phase extraction and solid phase microextraction are known. Ionic liquids have been used in task-specific liquid-liquid extraction for use in extraction of $Hg^{2+}$ and $Cd^{2+}$ from water. U.S. Patent Publication No. 2006/0025598 reports the use of diionic liquid salts and immobilized ionic liquids for solid phase extraction. U.S. Pat. No. 6,531,241 reports cyclic delocalized cations joined together by spacer groups.

SUMMARY OF THE INVENTION

In one embodiment, a polyionic liquid salt is provided. The polyionic liquid salt comprises a polyionic species that corresponds in structure to Formula I:

$$Gc(A)_m \qquad (I)$$

and at least one counterion;

Gc is a non-charged substitutable central group selected from the group consisting of nitrogen atom, phosphorous atom, silicon atom, alkyl, carbocyclyl, and heterocyclyl; wherein the nitrogen atom optionally is substituted with one or more substituents selected from the group consisting of alkyl and alkylcarbonylaminoalkyl;

wherein Gc optionally is further substituted with one or more Rc substituents independently selected from the group consisting of alkyl, cycloalkyl, phenyl, halo, alkoxy and hydroxyl;

each A is an independently selected monoionic group, wherein:

the monoionic group is selected from the group consisting of alkylene, alkenylene, alkynylene, (—$CH_2$-carbocyclyl-$CH_2$—)$_n$, and polysiloxyl; wherein alkylene, alkenylene, and alkynylene optionally contain one or more heteroatoms selected from the group consisting of O, N, S and Si;

wherein the monoionic group is substituted with a cationic group selected from the group consisting of heterocyclyl, ammonium and phosphonium; wherein the cationic group optionally is substituted with one or more substituents independently selected from the group consisting of alkyl, cycloalkyl, phenyl, halo, alkoxy and hydroxyl; wherein the alkyl optionally is substituted with one or more substituents selected from the group consisting of hydroxy and phenyl; or the monoionic group is an anionic group selected from the group of substituents consisting of carboxylate, sulfonate and sulfate; wherein each such substituent is optionally substituted with one or more substituents independently selected from the group consisting of alkyl, carbocyclyl and heterocyclyl;

n is selected from the group consisting of 1 to 20, inclusive; and m is selected from the group consisting of 3, 4, 5 and 6.

In another embodiment, a further polyionic liquid salt is provided. The polyionic liquid salt comprises a polyionic species having Formula (III), (IV) or (V):

A-B-A-B-A,  Formula (III)

  Formula (IV)

A-B-A-B-A-B-A,  Formula (V)

and at least one counterion;
wherein each B is independently selected from the group consisting of alkylene, alkenylene, alkynylene, (—$CH_2$-carbocyclyl-$CH_2$—)$_n$, and polysiloxyl;
  wherein alkylene, alkenylene, and alkynylene optionally contain one or more heteroatoms selected from the group consisting of O, N, S or Si;
  wherein B is optionally substituted with one or more substituents selected from the group consisting of alkyl, alkenyl, alkynyl, and alkoxy;
  each A is an independently selected monoionic group, wherein:
    the monoionic group is a cationic group selected from the group consisting of heterocyclyl, ammonium and phosphonium; wherein the cationic group optionally is substituted with one or more substituents independently selected from the group consisting of alkyl, cycloalkyl, phenyl, halo, alkoxy and hydroxyl; wherein the alkyl optionally is substituted with one or more substituents selected from the group consisting of hydroxy and phenyl; or
    the monoionic group is an anionic group selected from the group of substituents consisting of carboxylate, sulfonate and sulfate; wherein each such substituent is optionally substituted with one or more substituents independently selected from the group consisting of alkyl, carbocyclyl and heterocyclyl;
  n is selected from the group consisting of 1 to 20, inclusive.

In a further embodiment, a solvent is provided comprising one or more polyionic liquid salts as defined herein.

In a further embodiment, a device is provided for chemical separation or analysis comprising a solid support and one or more polyionic liquid salts as defined herein, wherein the one or more polyionic liquid salts is adsorbed, absorbed or immobilized on the solid support.

In a further embodiment, a method for separating one chemical from a mixture of chemicals is provided. The method comprises:
  providing a mixture of at least one first and at least one second chemical;
  exposing the mixture to a solid support containing one or more polyionic liquid salts as defined herein; wherein the one or more polyionic liquid salts is adsorbed, absorbed or immobilized on the support, and retaining at least a portion of the first chemical on the solid support.

In a further embodiment, a method of detecting an anion by ESI-MS is provided. The method comprises using one or more polycationic liquid salts as defined herein.

Other embodiments, including particular aspects of the embodiments summarized above, will be evident from the detailed description that follows.

DETAILED DESCRIPTION

Figure 1:
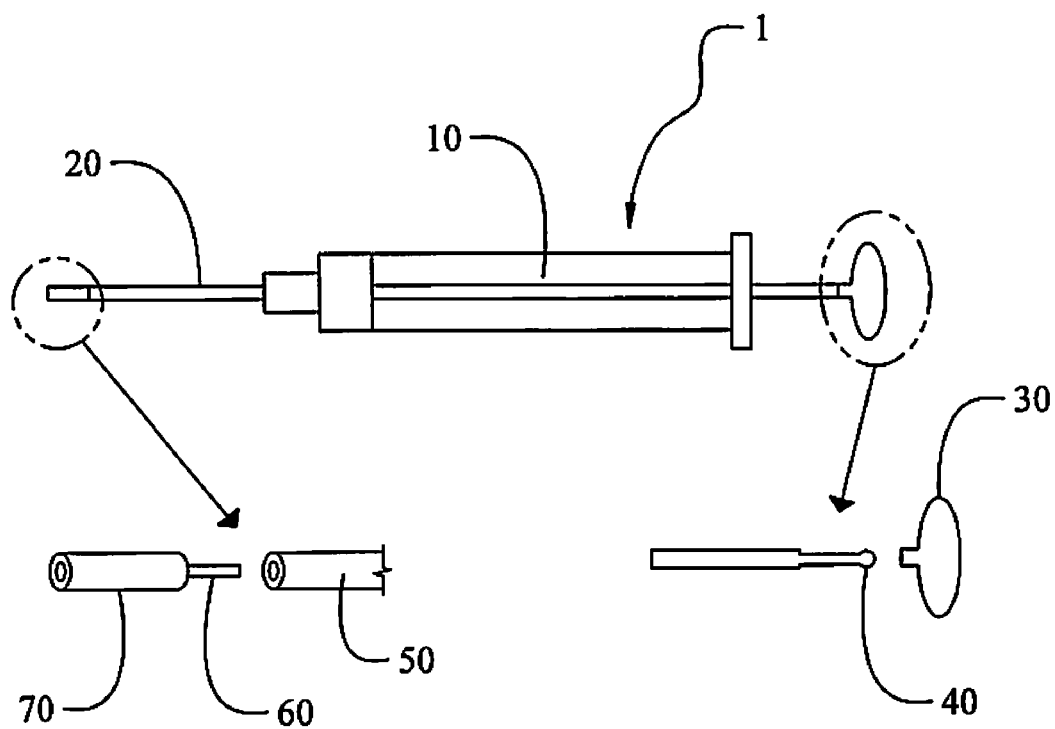
FIG. 1 is an embodiment of a syringe useful for SPME and SPME/MALDI mass spectrometry.

While the specification concludes with the claims particularly pointing out and distinctly claiming the invention, it is believed that the present invention will be better understood from the following description.

A. Definitions

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 7 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl.

A carbocyclyl may alternatively be polycyclic or contain more than one ring. Examples of polycyclic carbocyclyls include bridged, fused, spirocyclic, and isolated carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, multiple rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl. In an isolated carbocyclyl, the rings are separate and independent, as they do not share any common atoms, but a linker exists between the rings.

The term "carbocyclyl" encompasses protonated carbocyclyls, such as

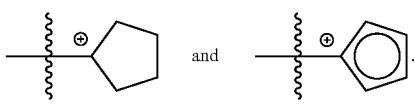

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., N, P, As, O, S and Si), with the remaining ring atoms being independently selected from the group consisting of carbon, oxygen, nitrogen, and sulfur. A heterocyclyl may be a single-ring (monocyclic) or polycyclic ring structure.

The term heterocyclyl encompasses protonated heterocyclyls such as pyridinium, pyridazinium, pyrimidinium, pyrazinium, imidazolium, pyrazolium, thazolium, oxazolium and triazolium.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic or contain more than one ring. Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, multiple rings may be fused together, such that two rings share one common bond. Examples of fused ring heterocyclyls containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

As used herein, the term "alkyl" (alone or in combination with another term(s)) refers to an alkane-derived radical containing from 1 to 20, carbon atoms. Alkyl includes straight chain alkyl, branched alkyl and cycloalkyl. Straight chain or branched alkyl groups contain from 1-15 carbon atoms, such as methyl, ethyl, propyl, isopropyl, butyl, t-butyl, and the like. Alkyl also includes straight chain or branched alkyl groups that contain or are interrupted by one or more cycloalkyl portions. Examples of this include, but are not limited to, 4-(isopropyl)-cyclohexylethyl or 2-methyl-cyclopropylpentyl. The alkyl group is attached at any available point to produce a stable compound. The term alkyl is also meant to encompass a fully substituted carbon.

The term "alkylene" (alone or in combination with another term(s)) refers to a divalent alkane-derived radical containing 1-20, preferably 1-15, carbon atoms, from which two hydrogen atoms are taken from the same carbon atom or from different carbon atoms. Examples of alkylene include, but are not limited to, methylene —CH$_2$—, ethylene —CH$_2$CH$_2$—, and the like.

The term "polysiloxyl" (alone or in combination with another term(s)) refers to a divalent radical composed of oxygen and silicon containing 1-20 atoms. Examples include (—Si—O—Si—)$_n$; wherein n is from 1-20.

The term "amino" (alone or in combination with another term(s)) means —NH$_2$. The term amino is meant to encompass a "monosubstituted amino" (alone or in combination with another term(s)) wherein one of the hydrogen radicals is replaced by a non-hydrogen substituent; and a "disubstituted amino" (alone or in combination with another term(s)) wherein both of the hydrogen atoms are replaced by non-hydrogen substituents, which may be identical or different.

The term "alkoxy" (alone or in combination with another term(s)) means an alkylether, i.e., —O-alkyl. Examples of such a substituent include methoxy (—O—CH$_3$), ethoxy, n-propoxy, isopropoxy, n-butoxy, iso-butoxy, sec-butoxy, tert-butoxy, and the like.

The term "aralkyl" (alone or in combination with another term(s)) refers to the group —R— Ar where Ar is an aryl group and R is lower alkylene or substituted lower alkylene group. The aryl functionality of aralkyl can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido, and the like.

The term "ammonium" refers to a positively charged polyatomic cation of the chemical formula NH$_4^+$. Ammonium also embraces positively charged or protonated substituted amines (such as protonated tertiary amine) and quaternary ammonium cations, N$^+$R$_4$, where one or more hydrogen atoms are replaced by organic radical groups (which is symbolized as R above).

Similarly, the term "phosphonium" refers to a positively charged polyatomic ion with the chemical formula PH$_4^+$. Phosphonium may also be substituted where one or more hydrogen atoms are replaced by organic radical groups.

All percentages and ratios used herein are by weight of the total composition and all measurements made are at 25° C. and normal pressure unless otherwise designated. All temperatures are in Degrees Celsius unless specified otherwise. The present invention can comprise (open ended) or consist essentially of the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise. As used herein "consisting essentially of" means that the invention may include ingredients in addition to those recited in the claim, but only if the additional ingredients do not materially alter the basic and novel characteristics of the claimed invention. Preferably, such additives will not be present at all or only in trace amounts. However, it may be possible to include up to about 10% by weight of materials that could materially alter the basic and novel characteristics of the invention as long as the utility of the compounds (as opposed to the degree of utility) is maintained. All ranges recited herein include the endpoints, including those that recite a range "between" two values. Terms such as "about", "generally", "substantially", and the like are to be construed as modifying a term or value such that is not an absolute, but does not read on the prior art. Such terms will be defined by the circumstances and the terms that they modify as those terms are understood by those of skill in the art. This includes, at the very least, the degree of expected experimental error, technique error, and instrument error for a given technique used to measure a value.

In its broadest sense, a "polyionic salt" or "PSI" is a salt formed between a polyionic species or "polyon" as described herein and one of more counterions of equal total charge. If a polyon has three cationic groups then one or more counterions would be necessary to provide a charge balance, e.g., −3. This could be achieved by using three monoanionic species, one monoanionic species and one dianionic species, or one trianionic species. The resulting salt in accordance with the invention is preferably a liquid at a temperature at about 100° C. or lower, more preferably at 25° C. or lower. A polyon, as used herein, refers to an ion, either a cation or an anion, which has n charges, where n is at least 3, i.e., n is 3, 4, 5 or an integer greater than 5. As used herein, this term is not meant to embrace a single charged species that has the specific total charge, e.g., a +3 ion such as $Al^{+3}$ or a −3 ion such as $PO_3^{-3}$. Rather it contemplates a single molecule with at least three discrete monoionic groups, each individually covalently bound to a central group. As used herein, the term "covalently bound" is meant that the two molecular moieties, e.g., a monoionic group and the central group, are linked via a covalent bond. Preferably, the monoionic groups do not form a covalent bond directly with each other. Preferably, the central group is not charged.

The monoionic groups in a polyon should be of the same charge. They may be different types of groups or the polyionic liquid salts may be "geminal" which means all ionic groups are not only the same charge, but also the same structure. The counterions need not be identical either. In one embodiment, either the polyon or the salt forming species is chiral, having at least one stereogenic center. The monoionic groups may also contain substituents which are themselves chiral. The central group may also be chiral or contain one or more chiral substituents. In such instances, the polyionic liquid salts, may be racemic (or in the case of diastereomers, each pair of enantiomers is present in equal amounts) or they may be optically enhanced. "Optically enhanced" in the case of enantiomers means that one enantiomer is present in an amount which is greater than the other. In the case of diastereomers, at least one pair of enantiomers is present in a ratio of other that 1:1. Indeed, the polyionic liquid salts may be "substantially optically pure" which one enantiomer or, if more than one stereogenic center is present, at least one of the pairs or enantiomers, is present in an amount of at least about 90% relative to the other enantiomer. The polyionic liquid of the salts of the invention may also be optically pure, i.e., at least about 98% of one enantiomer relative to the other.

Usually, the term polyionic salt is used to describe a salt molecule, although, as the context suggests, is may be used synonymously with "polyionic liquid" (PIL") and "polyionic liquid salt" ("PILS"). A "polyionic liquid" or "PIL" in accordance with the present invention is a liquid comprised of polyionic salts. Thus, sufficient PIS molecules are present such that they exist in liquid form at the temperatures indicated herein. This presumes that a single PIS molecule is not a liquid. A PIL is either a polycationic ionic liquid or a polyanionic ionic liquid (a liquid comprising either polycationic salts or polyanionic salts as described herein) or a mixture thereof. PILS may also be mixed with other solvents that are not PILS. Any polycationic ionic liquid which is stable and has a solid/liquid transformation temperature of about 500° C. or lower, more preferably about 400° C. or lower is contemplated. The same is true for "polyanionic ionic liquids" also known as "liquid salts of a polyanion", except the charges are reversed. Polycationic liquids and polyanionic liquids can also be referred to herein as polyionic liquid salts ("PILS" or "PCLS" and "PALS" depending upon charge). A polyon which contains three mono-ionic groups is also termed a triion.

B. Polyionic Liquid Salts

This invention is directed, in part, to polyionic liquid salts comprising a polyionic species and at least one counterion.

In some embodiments, the polyionic liquid species comprise at least one polyanionic or polycationic liquid salt molecule.

In some embodiments, the polyionic liquid salt comprising a polyionic species having at least three discrete monoionic groups and an appropriate number of counterions. The polyionic liquid salt does not substantially decompose nor substantially volatilize at a temperature of about 200° C. or lower and have a solid/liquid transformation temperature of about 100° C. or lower and/or a liquid range of at least about 200° C. In a particular embodiment, the polyionic liquid salt has a solid/liquid transformation temperature of about 25° C. or lower.

B1. Central Group Polyionic & Non-Central Group Polyionic Salts

In one embodiment, the monoionic groups in the polyionic species are individually covalently bound to a non-charged central group. Such polyionic liquid salts are termed central group polyionic liquid salts (CGPs). The polyionic species can be polyanionic or polycationic.

In some embodiments, central group polyionic salts are of the structure of Formula $Gc(A)_m$, wherein Gc is the central group, each A is a monoionic group and m, which is at least three, is the number of such groups in the polyionic species.

In some embodiments, the polyionic species corresponds in structure to Formula I:

$$Gc(A)_m \qquad (I)$$

wherein Gc, m and each A can be as defined hereinafter.

In some embodiments, the polyionic species corresponds in structure to Formula II:

$$Gc(A)_3 \qquad (II)$$

wherein Gc and each A can be as defined hereinafter.

In some embodiments, the polyionic species corresponds in structure to Formula VI:

$$Gc(A)_4 \qquad (IV)$$

wherein Gc and each A can be as defined hereinafter.

In another embodiment, the polyionic species does not include a central group. These are termed as Non-Central Group Polyons or "NCGPs." These polyons can have generally linear, branched or even cyclic structures. The monoionic A groups are separated by bridging groups, B. Each NCGP will include at least three monoionic groups as previously defined in connection with CGPs and each group may be as previously defined for $(A)_m$.

Each A and B may, where present, be the same or different.

In some embodiments, the polyionic species corresponds in structure to Formula III:

A-B-A-B-A            (III)

wherein each A and B can be the same or different and as defined hereinafter.

In some embodiments, the polyionic species corresponds in structure to Formula IV:

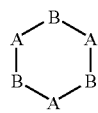

(IV)

wherein each A and B can be the same or different and as defined hereinafter.

In some embodiments, the polyionic species corresponds in structure to Formula V:

A-B-A-B-A-B-A         (V)

wherein each A and B can be the same or different and as defined hereinafter.

B2. Polyionic Liquid Salt Stability & Volatility

In some embodiments, the polyionic liquid salts are stable and will neither substantially decompose nor substantially volatilize, as measured as described herein, at a temperature of about 200° C. or lower and will have a temperature of solid/liquid transformation temperature of about 100° C. or lower or a liquid range of at least about 200° C.

In another embodiment, the polyionic liquid salt has both a solid/liquid transformation temperature of about 100° C. or lower and a liquid range of at least about 200° C. In a particular embodiment, the polyionic liquid salt containing the polyionic species of Formula (I) has a solid/liquid transformation temperature of about 100° C. or lower and/or a liquid range of 200° C. or higher and/or are substantially non-volatile and non-decomposable at temperatures below 200° C.

In a particular embodiment, a polycationic ionic liquid or polyanionic liquid will not substantially decompose or volatilize (or remain substantially non-volatile) as measured by being immobilized as a thin film in a fused silica capillary or on a silica solid support as described herein, at a temperature of about 200° C. or lower. Other types of solid supports, such as diatomaceous earth (commonly used in packed GC) carbons (e.g. Carbopack and Carboxen), metal particles (e.g. zirconia, titania, etc.), polymeric particles (e.g. styrene-divinylbenzene or SDVB) can be used in place of silica. This is in addition to the particles as described herein. Indeed, any media useful in chromatography can be used. "Substantially" in this context means less than about 10% by weight will decompose or volatilize at about 200° C. inside a capillary over the course of about one hour. Moreover, the polycationic ionic liquid in accordance with this embodiment will preferably have either a solid/liquid transformation temperature at about 100° C. or lower or a liquid range (the range of temperatures over which it is in a liquid form without burning or decomposing) of at least about 200° C.

In another particular embodiment, a polycationic ionic liquid will have both a solid/liquid transformation temperature at about 100° C. or lower and a liquid range of at least 200° C.

In another particular embodiment, a polycationic ionic liquid will not substantially volatilize or decompose, as discussed herein, at a temperature of less than about 300° C. "Substantially" in this context means that less than about 10% by weight will decompose or volatilize at about 300° C. inside a capillary over the course of about one hour. Moreover, the polyvcationic ionic liquids in accordance with this embodiment will preferably either have a solid/liquid transformation temperature at 25° C. or lower.

In another particular embodiment, the polycationic ionic liquids will also have a liquid range of at least about 200° C. In a further particular embodiment, the liquid range will be about 300° C. or above.

In a particular embodiment, a polyanionic ionic liquid will not substantially decompose or volatilize as measured by being immobilized as a this film in a fused silica capillary as described herein, at a temperature of about 200° C. or lower. Moreover, the polyanionic ionic liquid in accordance with this embodiment will have either a solid/liquid transformation temperature at about 100° C. or lower or a liquid range of at least about 200° C.

In another embodiment, these polyanionic ionic liquids will have both a solid/liquid transformation temperature at about 100° C. or lower and a liquid range (polyionic molecule is stable over the entire temperature range) or at least about 200° C.

In another embodiment, the invention provides a polyionic liquid salt having a melting point of between about −10 and about −20° C.

In another aspect of the invention, a polyanionic ionic liquid will not substantially volatilize or decompose, as discussed herein, at a temperature of less than about 300° C. Moreover, the polyanionic ionic liquids in accordance with this embodiment will preferably have either a solid/liquid transformation temperature at about 25° C. or lower. In another embodiment, the polyanionic liquids will also have a liquid range of at least 200° C. In an even more preferred aspect of the invention, the liquid range will be about 300° C. or above.

Therefore, in one embodiment, a polyionic liquid salt is provided which is either a polycationic ionic liquid salt or a polyanionic ionic liquid salt which will neither substantially decompose nor volatilize, as measured as described herein, at a temperature of about 200° C. or lower and will have a temperature of solid/liquid transformation temperature of about 100° C. or lower or a liquid range of at least about 200° C.

In other aspects of the invention, these polyionic liquid salts will have both a solid/liquid transformation temperature at about 100° C. or lower and a liquid range of at least about 200° C.

In other embodiments in accordance with the present invention, the polyionic liquid salts, either polycationic or polyanionic will be stable, that is not substantially volatilized or decomposed, as discussed herein, at a temperature of less than about 300° C. and will have a solid/liquid transformation temperature at about 25° C. or lower. In a particular embodiment of this aspect of the present invention, the polyionic liquid salt has a liquid range of at least about 200° C. and even more preferably at least about 300° C. Any polyionic compound which can form a stable liquid salt that meets the broadest parameters is contemplated.

B3. Polyionic Species Symmetry

Polyionic species of the present invention can be classified as symmetric or unsymmetric.

In some embodiments, the polyionic species are symmetric.

By "symmetric," it is meant that the polyionic species possess a symmetric central group and identical ionic groups $(A)_m$. For example, a symmetric triionic species may contain three identical mono-ionic groups attached to a central phenyl group at carbon 1, 3 and 5. Such a triionic species possesses $C_3$ symmetry with respect to the 3 mono-ionic groups. This would still be considered symmetric even if the counterions are different. If Gc is cycloheptane, the three monoionic groups could not be completely symmetrically attached and thus it is not symmetrical.

The polyionic species can also be center-symmetric. By "center-symmetric," it is meant that the polyionic species possess a symmetric central group regardless whether the ionic groups, $(A)_m$, are identical. For example, a center-symmetric triionic species may contain three different monoionic groups attached to a central phenyl group.

In other embodiments, the polyionic species are unsymmetric.

By "unsymmetric," it is meant that the monoionic groups, $A_m$, are structurally different, or that the central group is unsymmetric, or that the monoionic groups conjugate to the central group in such a manner that the polyionic species is not symmetric. The invention encompasses unsymmetric polyionic species due to any compositional and/or structural arrangement.

In some embodiments, an unsymmetric polyionic species of the invention contains different monoionic groups For example, $(A)_m$ can be different cations such as substituted or unsubstituted, saturated or unsaturated, straight or branched aliphatic chain, cyclic group, aromatic group, ammonium such as quaternary ammonium and protonated tertiary amine, phosphonium or arsonium group; or different anions such as substituted or unsubstituted, saturated or unsaturated, straight or branched aliphatic chain, cyclic group, aromatic group, carboxylate, sulfonate, and sulfate. In some other embodiments, the central group is unsymmetric. For example, the central group can be a 4-membered ring. In still some other embodiments, the monoionic groups conjugate to the central group in such a manner that the polyionic species is not symmetric. For example, the triionic species can contain 3 identical monoionic groups conjugated to carbon 1, 2 and 4 of a benzene ring.

Although each individual types of unsymmetric features described above is sufficient for the polyionic species to be unsymmetric, a combination of two or more types of unsymmetric features are also contemplated.

The unsymmetric polyionic salts of the invention can be used in a substantially pure form in any of the applications, e.g., the applications disclosed in this application. As compared to corresponding symmetric polyionic salts, polyionic salts which do not have identical monoionic groups or which include an unsymmetric central group generally have lower melting temperatures, and advantage for "liquid" salts. In addition, the higher the degree of internal structural dissimilarity as compared to corresponding symmetric polyionic salts, generally the lower the melting temperatures will result as compared to those of the corresponding symmetric polyionic salts. The trend can be thought of as a continuum from a symmetric molecule on the one end and a group with all different counterions, all different ions, different substituents, and an unsymmetric central group on the other. The former would be expected to have the highest melting point and the latter the relatively lowest. Of course, there can be variations to this trend. For example, a specific counterion might have a greater effect on decreasing melting point than the use of other different ions.

The unsymmetric polyionic salts of the invention may also be advantageous for uses as solvents. For example, a triionic species having three different A groups offers three sets of possible interactions with other molecules in the solution as compared to only one set in the case of a symmetric triionic species. Indeed, the more unsymmetric, the more the variety of interactions that can result. Thus, the invention provides a use of a polyionic liquid of a substantially pure "unsymmetric" polyionic salt as described above as a solvent.

The unsymmetric polyionic liquid salts of the invention can be used in a substantially pure form in any of the applications, e.g., the applications disclosed in this application. The unsymmetric polyionic salts of the invention can also be used in combination with any of the symmetric polyionic salts as a mixture. Thus, in one embodiment, the invention provides a polyionic liquid of a substantially pure unsymmetric polyionic salt as described above. In another embodiment, the invention provides a polyionic liquid comprising at least one of the unsymmetric polyionic salts as described above and at least one of the symmetric polyionic salts of the invention. A person skilled in the art would be able to determine the proportion of the symmetric and unsymmetric polyionic liquid salts when used as a mixture according to the particular application.

B4. $(A)_m$ Substituent

In $(A)_m$, each A is a monoionic group and m is the number of such groups in the polyionic liquid salt of the invention. $A_3$ therefore means that there are three monoionic groups just as $A_5$ means that there are five monoionic groups. Each A may be the same or different so long as they are all anions or all cations as appropriate.

In some embodiments, m is selected from the group consisting of 3, 4, 5, and 6.

In some embodiments, A is chiral and therefore contains at least one stereogenic center.

In some embodiments, each A is a cationic or anionic group.

In some embodiments, each A is a cationic group.

In some such embodiments, each A is cationic and is, without limitation, carbocyclyl, heterocyclyl, quaternary ammonium, protonated tertiary amine, phosphonium or arsonium groups.

In some embodiments, each A is a monoionic group selected from the group consisting of alkylene, alkenylene, alkynylene, $(-CH_2\text{-carbocyclyl-}CH_2-)_n$, and polysiloxyl; wherein alkylene, alkenylene, and alkynylene optionally contain one or more heteroatoms selected from the group consisting of O, N, S and Si;

wherein the monoionic group is substituted with a cationic group selected from the group consisting of heterocyclyl, quaternary ammonium, protonated tertiary amine and phosphonium; wherein the cationic group optionally is substituted with one or more substituents independently selected from the group consisting of alkyl, cycloalkyl, phenyl, halo, alkoxy and hydroxyl; wherein the alkyl optionally is substituted with one or more substituents selected from the group consisting of hydroxy and phenyl; and n is selected from the group consisting of 1 to 20, inclusive.

In some such embodiments, each A is independently selected from the group consisting of:

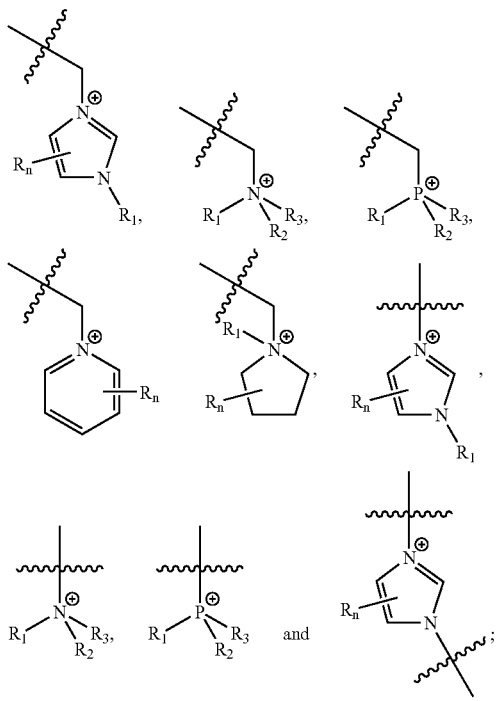

wherein $R_1$, $R_2$, $R_3$ and $R_n$ can be the same or different, and each of $R_1$, $R_2$, $R_3$ and $R_n$ can be hydrogen, substituted or unsubstituted, saturated or unsaturated, straight or branched aliphatic chain (such as alkyl), carbocyclyl (such as cycloalkyl or phenyl), heterocyclyl, halo, alkoxy, hydroxyl, hydroxyalkyl or aralkyl.

In other embodiments, each A is an anionic group.

In other such embodiments, each A is anionic and is, without limitation, substituted or unsubstituted, saturated or unsaturated, straight or branched aliphatic, cyclic or aromatic group, carboxylate, sulfonate, and sulfate; wherein each such substituent is optionally substituted with one or more substituents independently selected from the group consisting of alkyl, carbocyclyl and heterocyclyl;

Typically, the structural considerations for polyionic liquids are the same whether they are polyanionic ionic liquids or polycationic ionic liquids. First, the polyionic liquids will include a polyionic species, either a polyanionic or a polycationic molecule. The polyionic species contains three or more monoionic groups shown as $(A)_m$ in Formula (I), and $(A)_3$ in Formula (II) separated by a center or central moiety as discussed herein. Any anion or cation that can be bound to a central group to provide a polyanionic ionic liquid salt or polycationic ionic liquid salt is contemplated. These include those that are identified above. Possible cations include, without limitation, quaternary ammonium $(-NI_3)^+$, protonated tertiary amine $(-NI_2H)^+$, a phosphonium and/or an arsonium group. These groups can be aliphatic, cyclic or aromatic. Anions may include, for example, carboxylates, sulfonates or sulfates. Examples of a dicarboxylic acid polyanion include, without limitation, succinic acid, nonanedioic acid and dodecanedioic acid.

In addition, hybrid polyanions and polycations are contemplated. Thus, for illustration only, a polycation can be composed of a combination of three different quaternary ammonium groups, or one quaternary ammonium group, one phosphonium group, and one arsonium group. A polyanion can be composed of three different carboxylate groups or a combination of carboxylate groups and sulfonate groups.

B5. Counterions

The polyionic liquids of the present invention are generally salts, although they may exist as ions (+3, −3, +4, −4 etc.) in certain circumstances. Thus, in most instances, each ion has a counterion, one for each anion or cation. Charge should be preserved in most cases. In the case of a polyanionic ionic liquid, cations are required and in the case of a polycationic ionic liquid, anions are required. The choice of anion can have an effect of the properties of the resulting compound and its utility as a solvent. And, while anions and cations will be described in the context of a single species used, it is possible to use a mixture of cations to form salts with a polyanionic species to form a polyanionic ionic liquid. The reverse is true for polycations. For clarity sake, the salt-forming ions will be referred to as counterions herein.

The polyon of Formulas I-V form a polyionic salt with counterions having a charge which is opposite to that of the A substituent.

In some embodiments, the counterions are cationic.

Cationic counterions can include any of the polycationic compounds previously identified for use in the production of polycationic ionic liquids. In addition, monoionic counterparts of these may be used. Thus, for example, quaternary ammonium, protonated tertiary amine, phosphonium, and arsonium groups are useful as cationic counterions for polyanionic molecules to form polyanionic ionic liquids in accordance with the present invention.

When A is anionic, the counterions are cationic which, without limitation, include a quaternary ammonium, a protonated tertiary amine, a phosphonium or an arsonium group.

In other embodiments, the counterions are anionic.

Anionic counterions can be selected from any of the polyanionic molecules discussed herein useful in the creation of polyanionic ionic liquids. These would include dicarboxylates, disulfonates and disulfates. The corresponding monoionic compounds may also be used including carboxylates, sulfonates, sulfates and phosphonates. Halogen and halogen-containing compounds that may be used include, without limitation, triflate, $NTf_2^-$, $PF_6^-$, $BF_4^-$ and the like. The counterions should be selected such that the polyionic liquids have good thermal and/or chemical stability and have a solid/liquid transformation temperature and/or a liquid range as described herein. Finally, the ionic groups of the present invention can be substituted or unsubstituted. They may be substituted with halogens, with alkoxy groups, with aliphatic, aromatic or cyclic groups, with nitrogen-containing species, with silicon-containing species, with oxygen-containing species, and with sulphur-containing species. The degree of substitution and the selection of substituents can influence the properties of the resulting material as previously described in discussing the nature of the bridge or chain. Thus, care should be taken to ensure that excessive steric hindrance and excessive molecular weight are avoided, that resulting materials do not lose their overall flexibility and that nothing will interfere with the ionic nature of the two ionic species.

When A is cationic, the counterions are anions which, without limitation, include halogens, mono-carboxylates mono-sulfonates, mono-sulfates, $NTf_2^-$, $BF_4^-$, triflates or $PF_6^-$ as well as molecules having anionic groups each selected from, without limitation, carboxylate, sulfate or sulfonate groups. Other counterions include, without limitation:

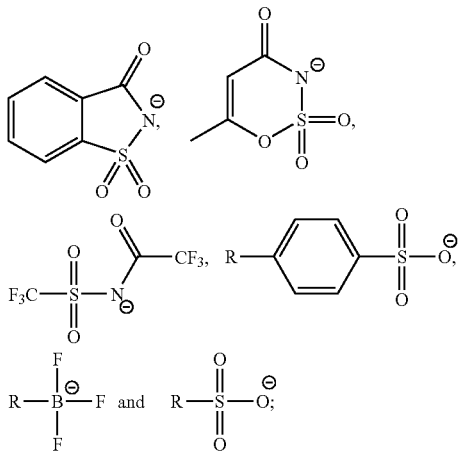

wherein R is selected from the group consisting of hydrogen, alkyl, hydroxyalkyl, carbocyclyl, heterocyclyl, halo, alkoxy, hydroxyl, alkylcarbonyl, alkylcarbonylalkylene, hydroxycarbonyl,

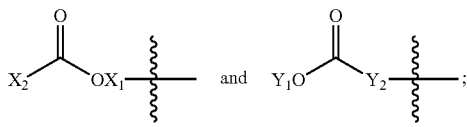

wherein
$X_1$ is $C_1$-$C_{10}$-alkylene;
$X_2$ is selected from the group consisting of hydrogen, alkyl, alkoxy, amino and hydroxy;
$Y_1$ is selected from the group consisting of hydrogen and alkyl; and
$Y_2$ is $C_1$-$C_{10}$-alkylene.

Counterions can be monoionic, diionic or polyionic ions, or a mixture thereof. They can be the same or different so long as they all have the same type of charge (positive or negative) and the total charge is m. For example, a polyionic liquid can be a mixture of a polycationic liquid and a polyaninoic liquid.

The counterions useful for each monoionic group of NCGPs are the same as those which may be used in connection with CGPs as previously defined.

B6. Gc Central Groups

Gc is a central group (also referred to as a center or central moiety) that may be substituted or unsubstituted, saturated or unsaturated, aliphatic, including straight or branched chains, cyclic or aromatic, and which may contain, in addition to, or even instead, of carbon atoms and hydrogen, N, P, As, O, S and Si atoms. In CGPs, the central group is not a charged (ionic) group.
In some embodiments, Gc is phenyl.
In some embodiments, Gc is cycloalkyl.
In some embodiments, Gc is C.
In some embodiments, Gc is Si.
In some embodiments, Gc is N.
In some embodiments, Gc is P.

The central group (Gc in Formula (I) and (II)) or center interposed among the ionic species can be of any length or any composition which affords a polyionic liquid salt of suitable properties. These include the groups identified as Gc above. There are certain factors that should be considered in selecting such a central moiety. First, the larger the polyionic molecule in general, the greater the chance that the melting point or temperature of solid/liquid transformation will be elevated. This may be less of a concern where the liquid range need not be extensive and/or where the temperature of solid/liquid transformation need not be very low. If, however, as is often the case, one desires a liquid range of about 200° C. or higher and/or a solid/liquid transformation temperature at 100° C. or lower, the size of the overall molecule can become a larger and larger factor. On the other hand, a larger mass might be good for certain mass spectrometry applications. Second, in some embodiments, it is preferable that the central group have some flexibility. In such embodiments, a linear molecule, usually saturated, or a cyclic or polycyclic group of limited unsaturation can be used as the central group. In some other embodiments, a more rigid polyionic molecule may be desirable. In such embodiments, a high degree of unsaturated groups, very rigid and/or sterically bulky groups, such as those found in, for example, cholesterol, and polyunsaturated aliphatic groups with extensive unsaturation, acryl groups, and cyclic groups including multiple fused ring structures, can be used as the center group. In still another embodiment, the central group can be a single atom such as C, Si, N and P.

The central group may be aliphatic, cyclic, or aromatic, or a mixture thereof. It may contain saturated or unsaturated carbon atoms or a mixture of same with, for example, alkoxy groups (ethoxy, propoxy, isopropoxy, butoxy, and the like). It may also include or be made completely from alkoxy groups, glycerides, glycerols and glycols. The central group may contain hetero-atoms such as O, N, S or Si and derivatives such as siloxanes, non-protonated tertiary amines and the like. The central group may be made from one or more cyclic or aromatic groups such as a cyclohexane, an immidazole, a benzene, a diphenol, a toluene, or a xylene group or from more complex ring-containing groups such as a bisphenol or a benzidine. These are merely representative and are not meant to be limiting. Generally, however, the central group will not contain an ionically charged species, other than the polyanions or polycations. And, it is possible to make mixtures of PILS each having, for example, the same cationic species, and each having the same counterions, but differing in the central groups alone. Other variations are also contemplated.

In some embodiments, the invention provides a polyionic liquid salt in which the central group is a linear central group having lengths ranging from a length equivalent to that of a saturated aliphatic carbon chain of between about 2 and about 40 carbon atoms (e.g., n=$C_2$-$C_{40}$ when central group is composed of carbon). Such a polyionic liquid salt is termed a linear-Gc-based polyionic liquid salt. More preferably, the length should be approximately that resulting from a saturated aliphatic carbon chain of about 3 to about 30 carbon atoms in length.

In some other embodiments, the invention provides a polyionic liquid salt in which the central group is a cyclic central group having at least a three member ring. Such a polyionic liquid salt is termed a cyclic-Gc-based polyionic liquid salt. In embodiments involving a cyclic central group, the number of carbons and/or any heteroatoms in the central group can be between 3 and about 40 (e.g., n=$C_3$-$C_{40}$ when central group is composed of carbon). More preferably, the number of carbons and/or any heteroatoms in the central group can be between 5 to about 30. The cyclic central group can have, but are not limited to a 3, 4, 5, 6 or 7-membered ring. The cyclic central group can also have a fused multiple ring.

The cyclic central group can be an alicyclic group containing one or more all-carbon rings which may be either saturated or unsaturated, either substituted or unsubstituted. Exemplary alicyclic groups include, but are not limited to, cycloalkanes, such as cyclopropane, cyclobutane and cyclohexane, cycloheptane, bicyclic alkanes, such as norbornene and norbornadiene, and polycyclic cycloalkane, such as Decalin, Spiro groups, which have bicyclic connected through one carbon atom, cycloalkenes are cyclobutene, cyclopropene and cyclohexene.

The cyclic central group can be an aromatic group containing one or more all-carbon rings which may be either substituted or unsubstituted. Exemplary aromatic groups include, but are not limited to, benzene, naphthalene, anthracene, benzo[a]pyrene, benzo[ghi]pyrene, chrysene, coronene, fluoranthene, tetracene, pentacene, phenanthrene, pyrene and triphenylene.

The cyclic central group can be a heterocyclic group that contains atoms in addition to carbon, such as sulfur, oxygen or nitrogen, as part of the ring. The heterocyclic groups can be either saturated or unsaturated, either substituted or unsubstituted, either aromatic or non-aromatic, single or fused. The heterocyclic groups can have, but are not limited to, 3, 4, 5, 6 or 7 membered rings.

The cyclic groups can also have fused multiple rings. Examples of fused multiple rings include, but are not limited to, benzocyclobutene, pentalene, benzofuran, isobenzofuran, indole, isoindole, benzothiophene, benzo[c]thiophene, benzimidazole, purine, indazole, benzoxazole, benzisoxazole, benzothiazole, naphthalene, anthracene, quinoline, isoquinoline, quinoxaline, acridine, quinazoline and cinnoline.

In embodiments in which the central group comprises a mixture of a linear and a cyclic group, the mono-onic groups can be distributed across the central group in any manner. For example, some of the monoionic groups, A, are conjugated to the cyclic portion while other monoionic groups are conjugated to the linear portion of the central group.

Gc can be optionally substituted with one or more Rc substituents independently selected from the group consisting of a proton, substituted or unsubstituted, saturated or unsaturated, straight or branched aliphatic chain (such as alkyl), cyclic group (such as cycloalkyl), aromatic group (such of phenyl or substituted phenyl), halo, alkoxy or hydroxyl.

B7. B Substituents

Each B is a bridging group.

Each B may, where present, be the same or different.

In some embodiments, each B is selected from the group consisting of alkylene, alkenylene, alkynylene, (—CH$_2$—O—CH$_2$—), (—CH$_2$-carbocyclyl-CH$_2$—)$_n$, and polysiloxyl; wherein alkylene, alkenylene, and alkynylene optionally contain one or more heteroatoms selected from the group consisting of O, N, S or Si;

In other such embodiments, B is optionally substituted with one or more substituents selected from the group consisting of alkyl, alkenyl, alkyl, and alkoxy.

C. Embodiments of Polyionic Species of Formulas I-VI

Various embodiments of substituents A, Gc, Rc, R$_A$, R$_1$, R$_2$, R$_3$, and R$_n$, have been discussed above. These substituent embodiments can be combined to form various embodiments of species of Formulas I-V. All embodiments of species of Formulas I-V formed by combining the substituents embodiments discussed above are within the scope of the invention.

Examples of such embodiments are shown below as non-limiting formulas.

C1. Triionic Species (Gc=Phenyl)

In some embodiments, Gc is phenyl, substituted with three Rc groups and m is 3. In these embodiments, the species of Formula II correspond in structure to Formulas IIA-IIC.

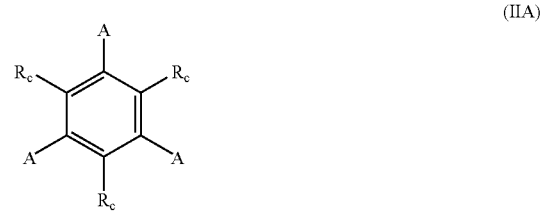

(IIA)

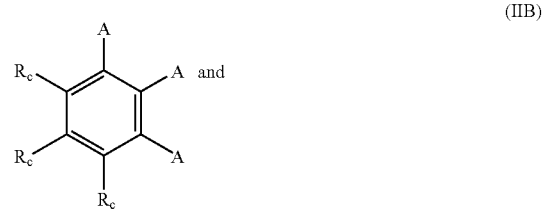

(IIB)

and

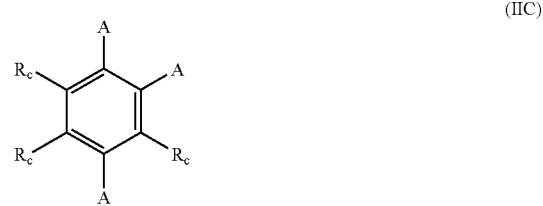

(IIC)

wherein each A and R$_c$ can be the same or different and are as defined above.

In some such embodiments, at least one R$_c$ is alkyl. In some such embodiments, at least two R$_c$ are alkyl. In some such embodiments, all three R$_c$ are alkyl. Examples of alkyl groups include methyl, ethyl, propyl, butyl and pentyl.

In some such embodiments, R$_c$ is alkyl and A is imidazolium. Examples of such triionic liquid salts are provided, without limitation in Table 1. Each of the above tricationic liquid salts has a melting point at about −10 to −20° C.

In some embodiments, all three Rc groups are hydrogen. In some such embodiments, A is imidazolium. Examples of such unsubstituted phenyl-based triionic liquid salts having imidazoliums are provided, without limitation in Table 2.

Formula IIA

In some embodiments, the species of Formula II correspond in structure to Formula IIA:

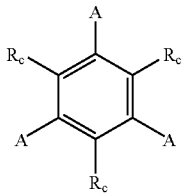

(IIA)

wherein each A is identical and as defined above.

In some such embodiments, all A groups are identical.

In some such embodiments, the A groups are selected from the group consisting of imidazolium, ammonium, phosphonium, pyridinium and pyrrolidinium.

In some such embodiments, A is imidazolium. In some such embodiments, the species of Formula IIA correspond in structure to the following formula:

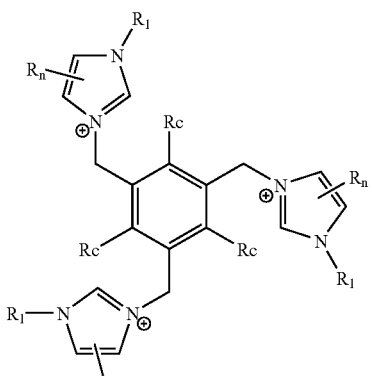

wherein each Rc, $R_1$, $R_n$ and the anion are as defined previously.

In some such embodiments, A is ammonium. In some such embodiments, the species of Formula IIA correspond in structure to the following formula:

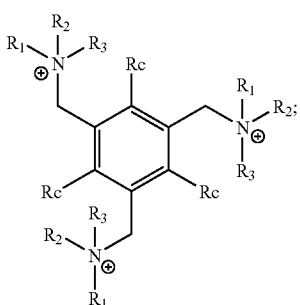

wherein each Rc, $R_1$, $R_2$, $R_3$, $R_n$ and the anion are as defined previously.

In another embodiment, a polyionic liquid salt comprises an optically active tricationic species having ammoniums substituted with at least one alkyl group having one or more chiral centers. In some such embodiments, the species of Formula IIA correspond in structure to the following formula:

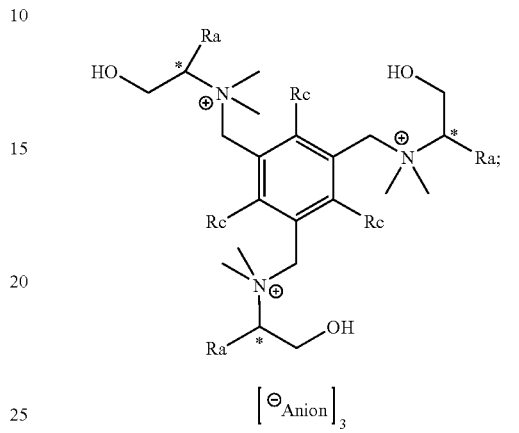

wherein each Ra and Rc and the anion are as defined previously. The above described chiral triionic species can be synthesized by procedures described in Example 10.

In another embodiment, a polyionic liquid salt comprises an optically active tricationic species having ammoniums substituted with aryl containing groups having one or more chiral centers. In some such embodiments, the species of Formula IIA correspond in structure to the following formula:

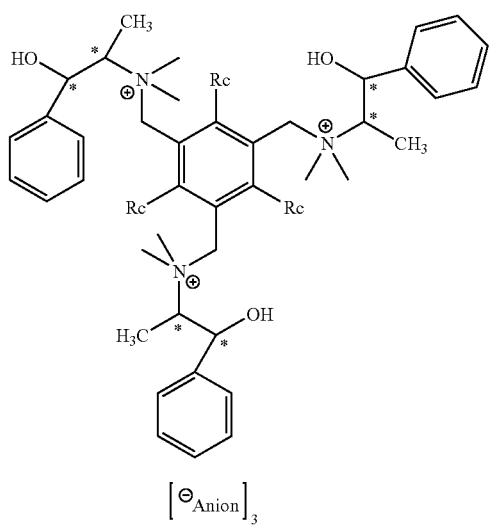

wherein each Rc and the anion are as defined previously. The above described chiral triionic species can be synthesized by procedures described in Example 11.

In some such embodiments, A is phosphonium. In some such embodiments, the species of Formula IIA correspond in structure to the following formula:

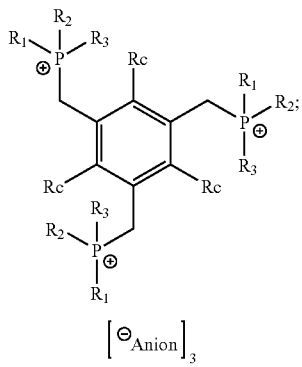

wherein each Rc, $R_1$, $R_2$, $R_3$ and the anion are as defined previously.

In some such embodiments, at least one A is phosphonium. In some such embodiments, the species of Formula IIA correspond in structure to the following formula:

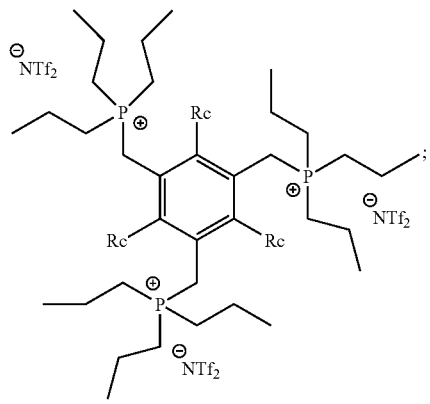

wherein each $R_c$ is as defined previously.

The above described central phenyl group-based triionic species can be synthesized by procedures described in Examples 1 and 2. Note that it is also possible to bond one or more additional groups to one or more of the ring carbons illustrated above as being substituted with hydrogen only.

Examples of phenyl-based triionic species containing phosphoniums are provided, without limitation in Table 4.

In some such embodiments, A is pyridinium. In some such embodiments, the species of Formula IIA correspond in structure to the following formula:

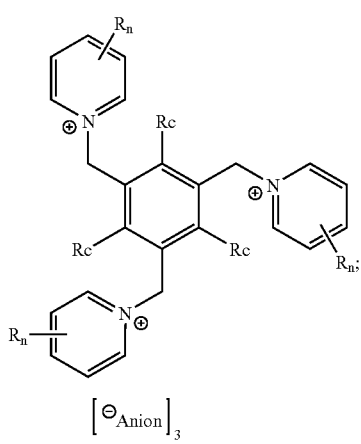

wherein each Rc, and $R_n$, and the anion are as defined previously.

In all of the Formula II embodiments listed herein, if any $R_1$, $R_2$, $R_3$, $R_n$, or Rc groups are different, for example, $R_n$ is Br in one group and Cl in two groups in the above molecule, it would no longer be symmetric. If one of the three Rc groups in the figure immediately above are different from the others, but all of the $R_n$ groups are the same, the triion would be neither symmetric nor center-symmetric, but it would still be an embodiment of the invention.

In some such embodiments, A is pyrrolidinium. In some such embodiments, the species of Formula IIA correspond in structure to the following formula:

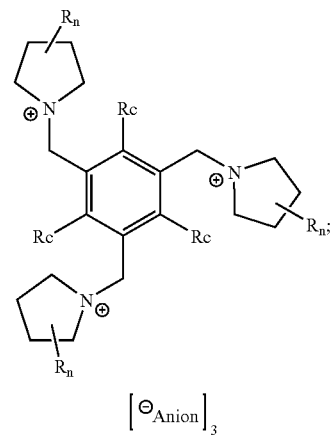

wherein each Rc and $R_n$ and the anion are as defined previously.

In some such embodiments, at least one A is pyrrolidinium. In some such embodiments, all three A groups are pyrrolidium. In some such embodiments, the species of Formula IIA correspond in structure to the following formula:

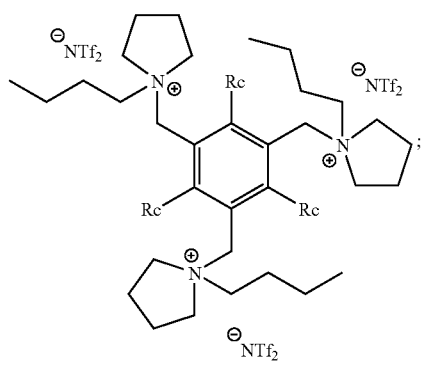

wherein each Rc is as defined above.

An example of such a triionic liquid salt is provided, without limitation in Table 3.

In some embodiments, a polyionic liquid salt comprises an optically active tricationic species having pyrrolidiniums with one or more chiral centers. In some such embodiments, the species of Formula IIA correspond in structure to the following formula:

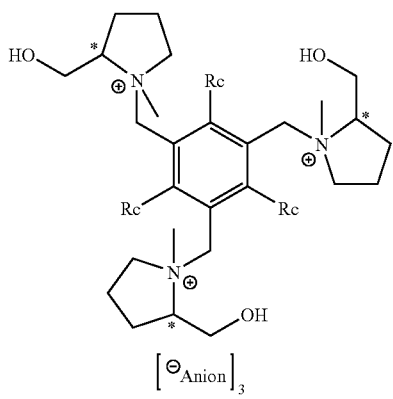

[⊖Anion]₃ wherein each Rc and the counteranion are as defined previously. (R)- or (S)- is marked by an asterisk (*). The above described chiral triionic species can be synthesized by procedures described in Example 9.

An appropriate counteranion can be selected from those defined above.

In some embodiments, the triionic species comprises three different A groups.

In some embodiments, a first A is a quaternary ammonium or a protonated tertiary amine, while a second A is an imidazolium (IM) or a substituted IM, and a third A is a pyridinium or a substituted pyridinium.

In some embodiments, the A groups are selected from imidazolium, ammonium and phosphonium. In some such embodiments, the species of Formula IIA correspond in structure to the following formula:

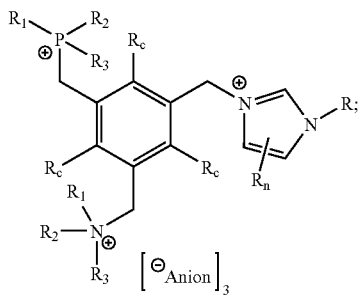

[⊖Anion]₃ wherein each Rc, R, $R_1$, $R_2$, $R_3$, and $R_n$, and the anion are as defined previously.

In some such embodiments, the species of Formula IIA correspond in structure to the following formula:

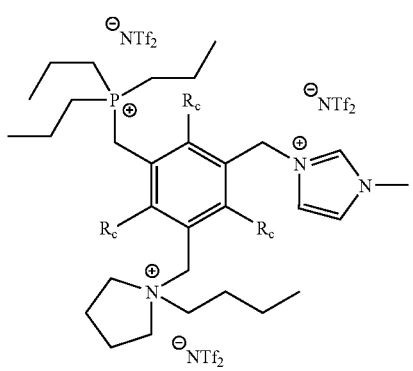

wherein each Rc is as defined previously.

Formula IIB

In some embodiments, the polyionic liquid salt comprises a symmetric triionic species of the formula IIB:

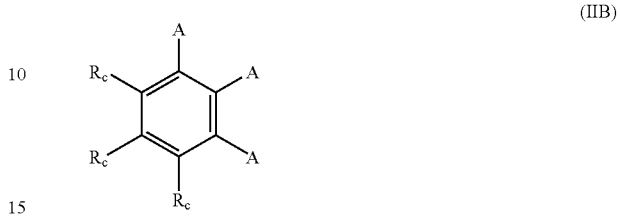

(IIB)

wherein each A is identical and as defined above.

In some such embodiments, the A groups are identical.

In some such embodiments, the A groups are selected from the group consisting of imidazolium, ammonium, phosphonium, pyridinium and pyrrolidinium.

In some such embodiments, A is imidazolium. In some such embodiments, the species of Formula IIB correspond in structure to the following formula:

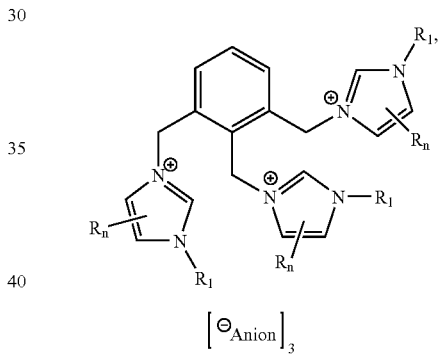

[⊖Anion]₃ wherein $R_1$, $R_n$ and the anion are as defined previously.

In some such embodiments, A is ammonium. In some such embodiments, the species of Formula IIB correspond in structure to the following formula:

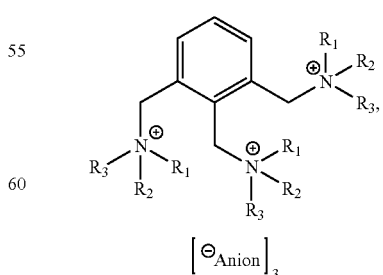

[⊖Anion]₃ wherein $R_1$, $R_2$, $R_3$, and the anion are as defined previously.

In some such embodiments, A is phosphonium. In some such embodiments, the species of Formula IIB correspond in structure to the following formula:

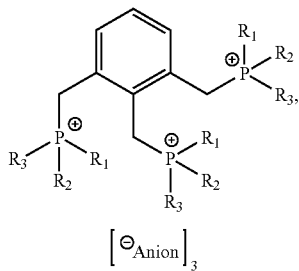

wherein $R_1$, $R_2$, $R_3$, and the anion are as defined previously.

In some such embodiments, A is pyridinium. In some such embodiments, the species of Formula IIB correspond in structure to the following formula:

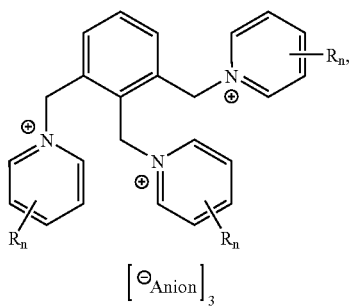

wherein $R_n$, and the anion are as defined previously.

In some such embodiments, A is pyrrolidinium. In some such embodiments, the species of Formula IIB correspond in structure to the following formula:

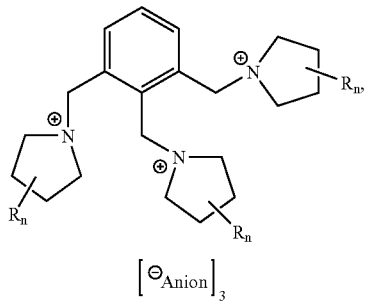

wherein $R_n$, and the anion are as defined previously.

The above described C2 symmetric central phenyl-based triionic species can be synthesized by procedures described in Example 12. Note that it is also possible to bond one or more additional groups to one or more of the ring carbons illustrated above as being substituted with hydrogen only.

Formula IIC

In some embodiments, the Gc is unsymmetric such that the polyionic species does not possess symmetry along the ionic groups.

For example, in some embodiments, the A groups are conjugated to Gc in such a manner that the species do not possess symmetry among the ionic groups. In some such embodiments, the A groups are conjugated to the carbon 1, 2, and 4 of the ring.

In some such embodiments, the polyionic liquid salt comprises a symmetric triionic species of the formula:

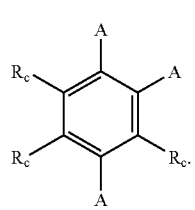

(IIC)

wherein each A is identical and as defined above.

In some such embodiments, the A groups are not all the same.

In other such embodiments, each A is the same monoionic group. Examples of such species of Formula IIC correspond in structure to the following formulas:

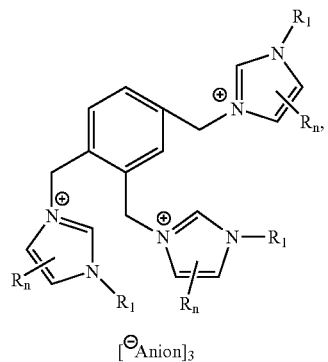

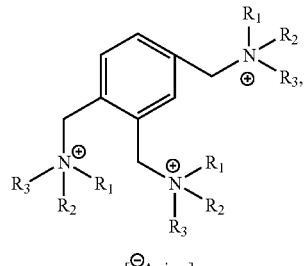

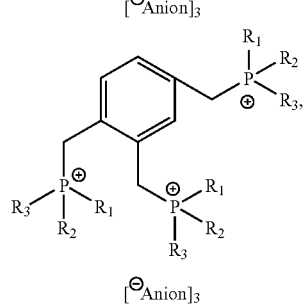

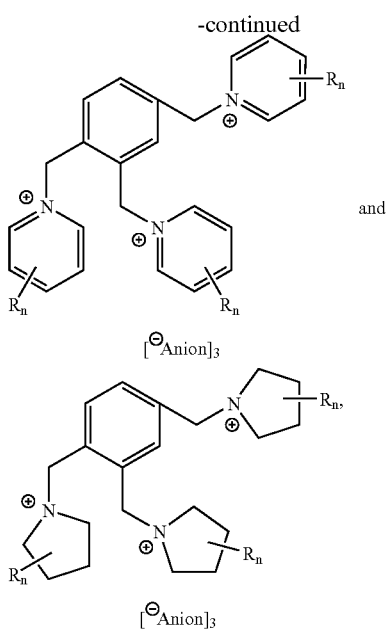

[⊖Anion]₃ and

[⊖Anion]₃ wherein $R_1$, $R_2$, $R_3$ and $R_n$ and the anion are as defined previously. The above described unsymmetric central phenyl-based triionic species can be synthesized by procedures described in Example 13.

C2. Tetraionic Species (Gc=Phenyl)

In some embodiments, the polyionic liquid salt comprises a tetraionic species wherein m is 4.

In some embodiments, the polyionic liquid salt comprises a tetraionic species wherein Gc is phenyl optionally substituted with one or more Rc substituents and m is 4.

In some such embodiments, the tetraionic species corresponds in structure to Formulas VIA-VIC:

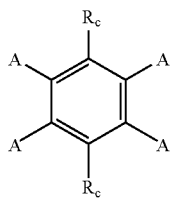

(VIA)

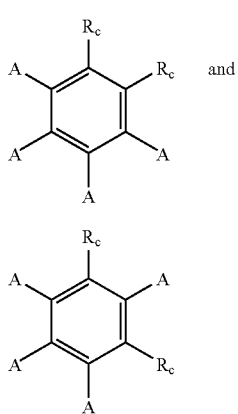

(VIB) and (VIC)

wherein each A is as defined above.

An example of a polyionic liquid salt is provided, without limitation in Table 5.

The above described central phenyl-based tetraionic species can be synthesized by procedures described in Example 14.

In some embodiments, the tetraionic species corresponds in structure to Formula VID:

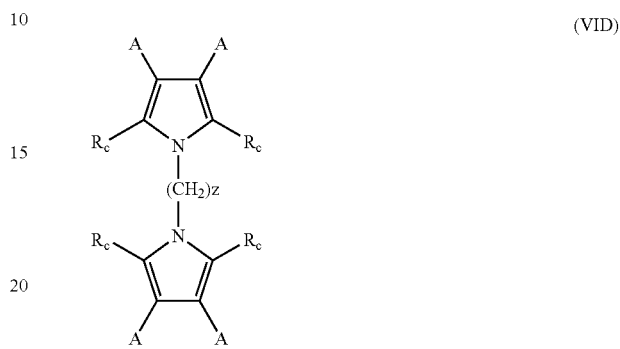

(VID)

wherein each A is as defined previously.

In some such embodiments, z is selected from the group consisting of 1 to 20, inclusive.

In some embodiments, at least one $R_c$ is alkyl. In some such embodiments, at two $R_c$ groups are alkyl. In other such embodiments, three $R_c$ groups are alkyl. In yet other such embodiments, all four $R_c$ groups are alkyl.

In some such embodiments, the species of Formula VID correspond in structure to the formula:

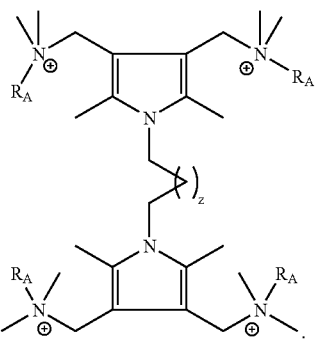

The above described central pyrrole-based tetraionic species can be synthesized by procedures described in Example 15.

C2. Triionic Species (Gc=Cycloalkyl)

In some embodiments, the polyionic liquid salt comprises a triionic species, wherein Gc is cycloalkyl substituted with one or more Rc substituents, which are as defined previously.

In some such embodiments, the three A monoionic groups are identical.

In some such embodiments, Gc is cyclohexane optionally substituted with one more Rc substituents.

In some embodiments, the monoionic A group is an imidazolium, ammonium, phosphonium, pyridinium or pyrrolidinium, and Gc is a cyclohexane or substituted cyclohexane.

In some such embodiments, the central cyclohexane-based triactionic salt is constructed using 1,3,5-trisubstituted cyclohexanes which have been proven useful as scaffolds for molecular architectures.

In some embodiments, the polyionic species corresponds in structure to:

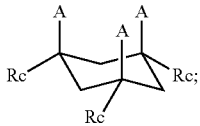

wherein each Rc, can be any of the Rc groups defined previously, and A is a monoionic group as defined previously. In addition, cyclohexane containing substitutions at 2, 4, and 6 carbon with any of the groups defined previously are also contemplated.

In some embodiments, the species of Formula II corresponds in structure to Formula IID:

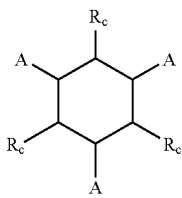

(IID)

wherein each $R_c$ and A are as defined above.

In some embodiments, the species of Formula II corresponds in structure to Formula IIE:

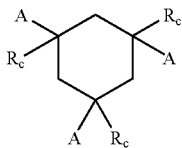

(IIE)

wherein each $R_c$ and A are as defined above.

In some embodiments, the species of Formula IIE correspond in structure to the following:

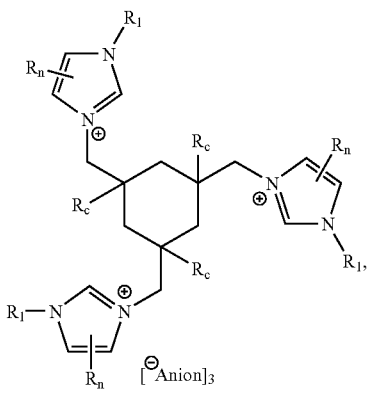

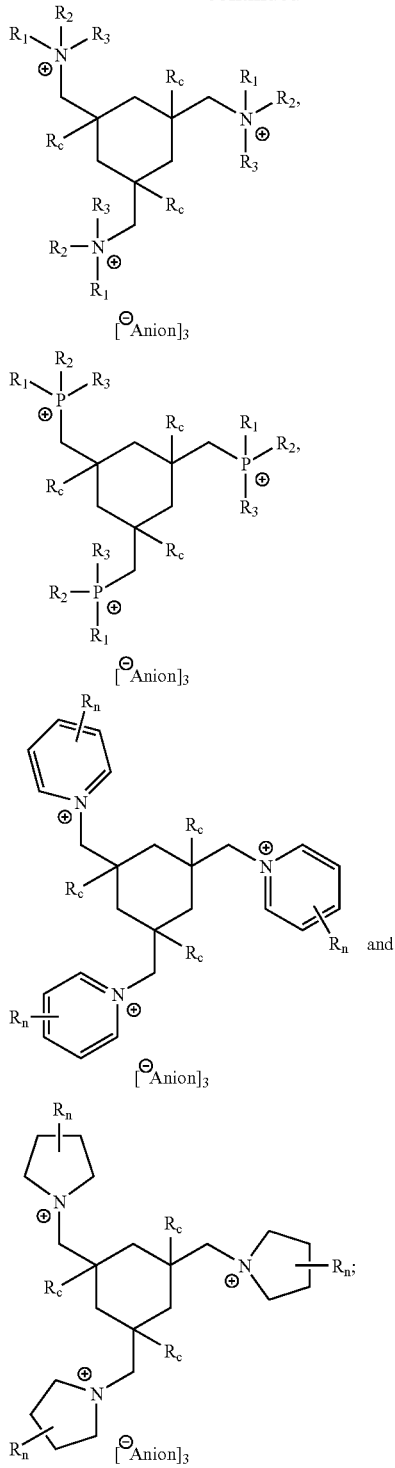

wherein Rc, $R_1$, $R_2$, $R_3$, $R_n$ and the anion are as defined previously. The above described central cyclohexane-based triionic species can be synthesized by procedures described in Examples 3 and 4. Note that it is also possible to bond one or more additional groups to one or more of the ring carbons illustrated above as being substituted with H only. Examples of a triionic liquid salt comprising such central cyclohexane-based tricationic species are provided, without limitation in Table 6.

C3. Triionic Species (Gc=C or Si)

In some embodiments, the polyionic liquid comprises a triionic species, wherein Gc is selected from the group consisting of C and Si. Such species are termed C-Gc-based or Si-Gc-based triionic species.

In some such embodiments, the three A groups are identical and as previously defined.

In some embodiments, the species of Formula II corresponds in structure to the C-Gc-based triionic species of Formula IIF:

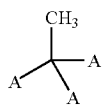
(IIF)

wherein each A is as defined above.

In some such embodiments, A is selected from the group consisting of imidazolium, ammonium, phosphonium, pyridinium and pyrrolidinium. In some such embodiments, the species of Formula IIF correspond in structure to:

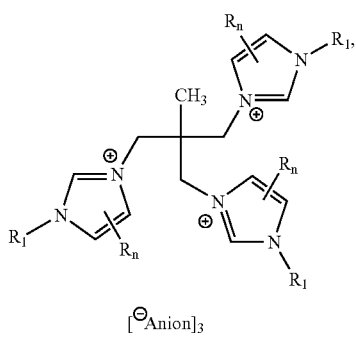

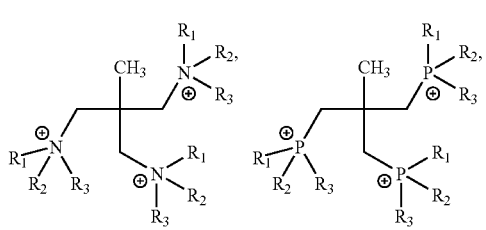

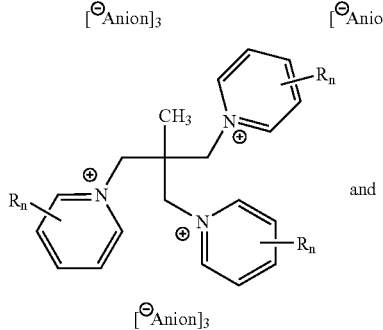

and

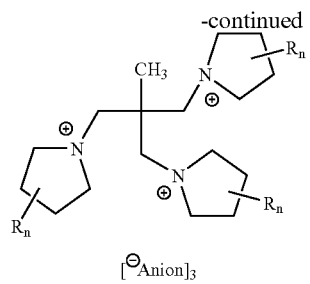

wherein $R_1$, $R_2$, $R_3$, $R_n$, and the anion are as defined previously. The above described central carbon-based triionic species can be synthesized by procedures described in Examples 5 and 6. Note that the presence of the methyl group (—$CH_3$) means that the above triions are neither symmetric nor centersymmetric. Examples of a polyionic liquid salt comprising such C-Gc-based triionic species are provided, without limitation in Table 7.

C4. Triionic Species (Gc=N or P)

In some embodiments, the polyionic liquid comprises a triionic species, wherein Gc is selected from the group consisting of N and P. Such species are termed N-Gc-based or P-Gc-based triionic species.

In some embodiments, Gc is P.
In some embodiments, Gc is N.

In some such embodiments, all three A groups are identical and can be any monoionic group previously defined.

In some embodiments, the species of Formula II corresponds in structure to the N-Gc-based triionic species of Formula IIG:

In some embodiments, the species of Formula II correspond in structure to Formula IIG:

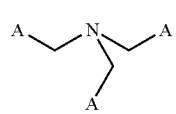
(IIG)

wherein each A is as defined above.

In some such embodiments, the A groups are identical.

In some such embodiments, the monoionic A group selected from the group consisting of imidazolium, ammonium, phosphonium and pyridinium.

In some such embodiments, the species of Formula IIG correspond in structure to:

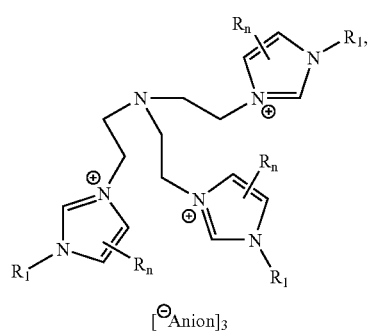

-continued

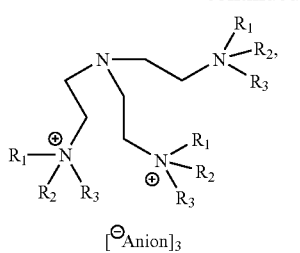

[⊖Anion]₃

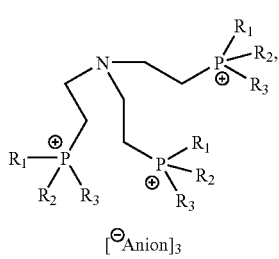

[⊖Anion]₃

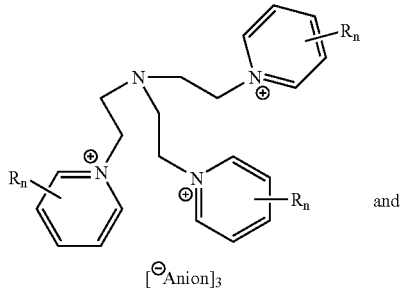 and

[⊖Anion]₃

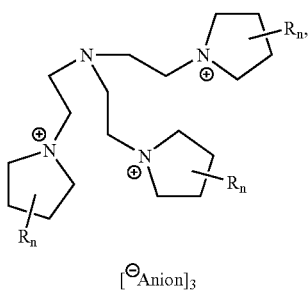

[⊖Anion]₃ wherein $R_1$, $R_2$, $R_3$, $R_n$ and the anion are as defined previously. The above described central carbon-based triionic species can be synthesized by procedures described in Examples 7 and 8. Assuming that all of the substitutions on each ion are the same, then these triions would be both symmetric and central-symmetric. Examples of such N-Gc-based species are provided, without limitation in Table 8.

In some embodiments, the species of Formula II correspond in structure to Formula IIIH:

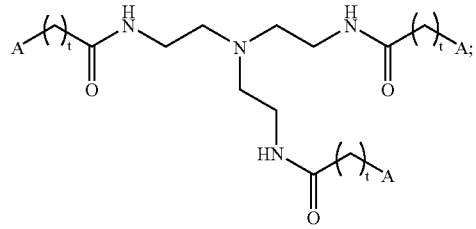

wherein each t is independently selected from the group consisting of 1 to 20, inclusive; and each A is as defined previously. Examples of such triionic species are provided, without limitation in Table 9.

C5. Triionic Species (Gc=Alkyl)

In some embodiments, the species of Formula II correspond in structure to Formula IIJ:

(IIJ)

wherein each A is as defined above.

In some such embodiments, A is an anionic group.

In some such embodiments, each A is independently selected from the group consisting of carboxylate, sulfonate and sulfate; wherein each such substituent is optionally substituted with one or more substituents independently selected from the group consisting of alkyl, carbocyclyl and heterocyclyl. Non-limiting examples of such a trianionic species is provided in Table 10. This trianionic species can be synthesized by procedures described in Example 16.

In other such embodiments, A is a cationic group. In these embodiments, the cationic group can be any previously defined.

C6. Non-Central Group Species

Exemplary species of Formula III can be synthesized by procedures described in Examples 17 and 18. Non-limiting examples of such triionic NCGP species are provided in Table 11.

In some embodiments, the species of Formula V correspond in structure to one of the following formulas:

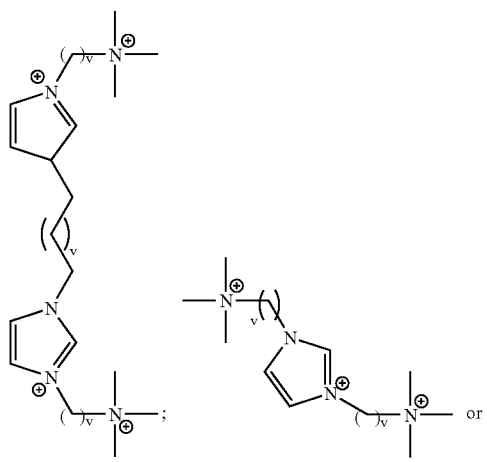

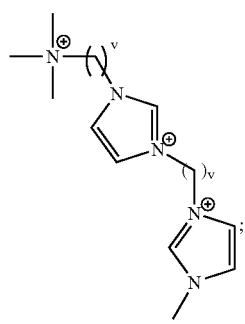

wherein each v is independently selected from the group consisting of 1-20, inclusive.

The species of Formula V can be synthesized by procedures described in Example 19. A cyclized version is also possible where the two free quaternary groups are joined to complete a ring.

C7. Species Examples

Examples of species of Formulas I-VI are shown in Tables 1-11 below. The synthesis examples below provide step-by-step preparation instructions for some of these species.

TABLE 1

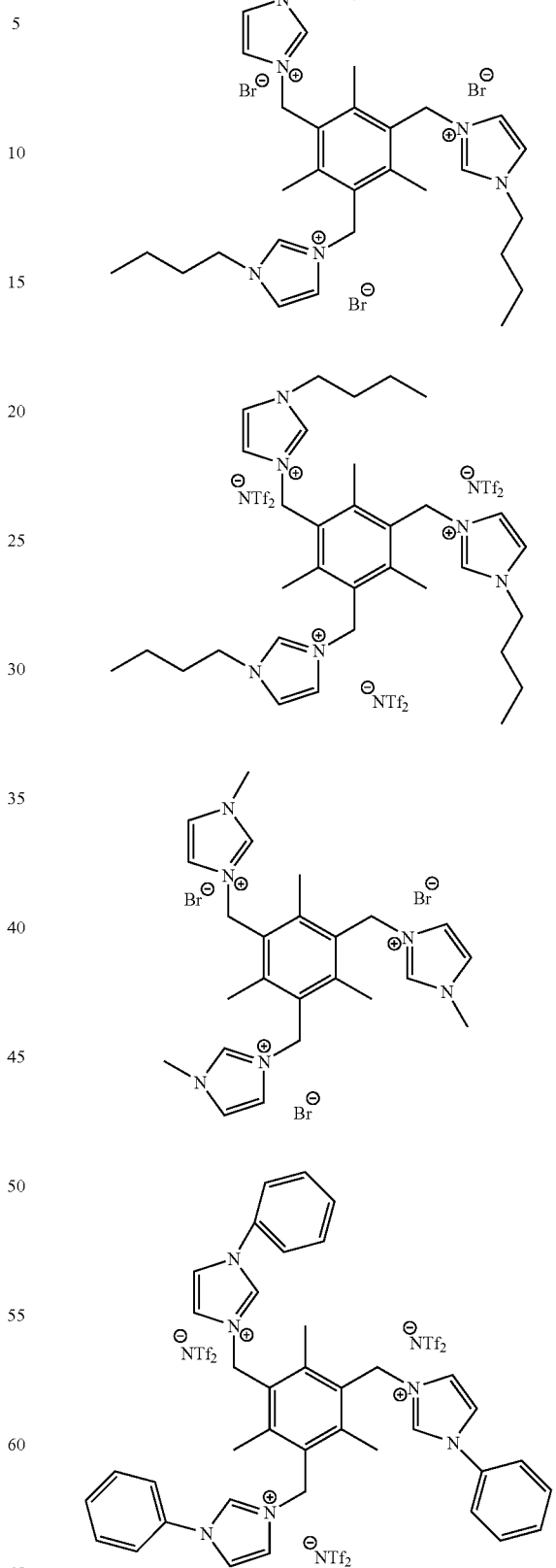

TABLE 2
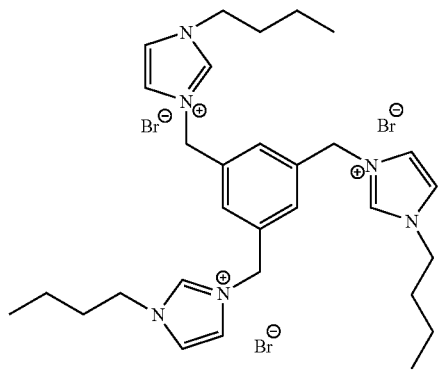
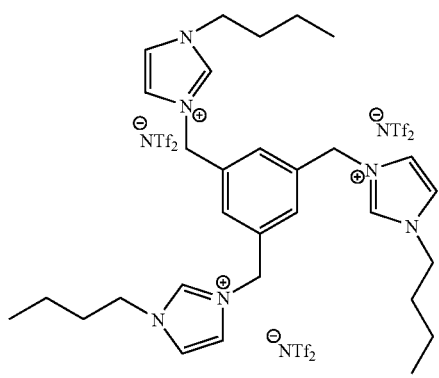
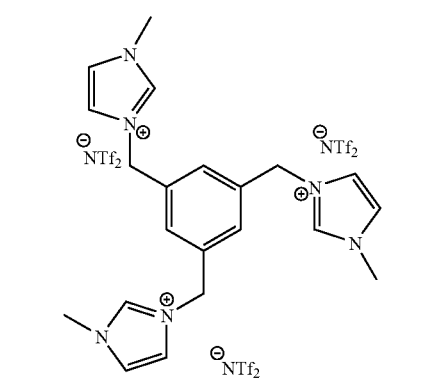
TABLE 3
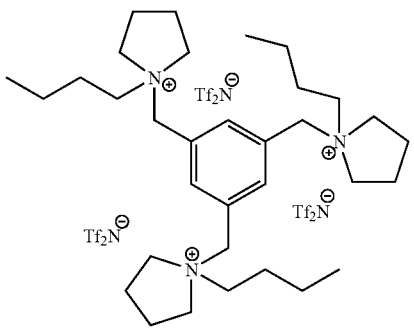
TABLE 4
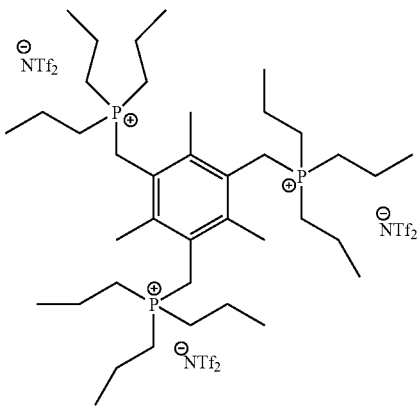
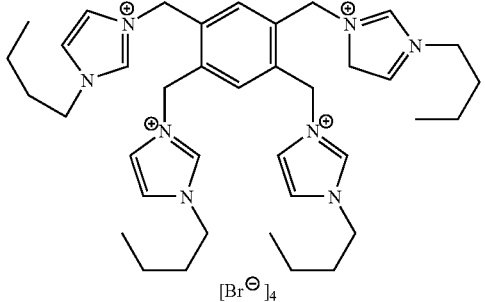
TABLE 5

TABLE 6
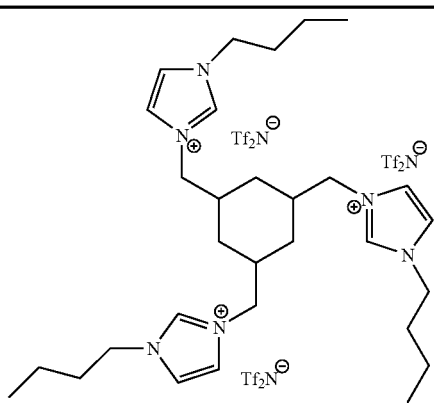
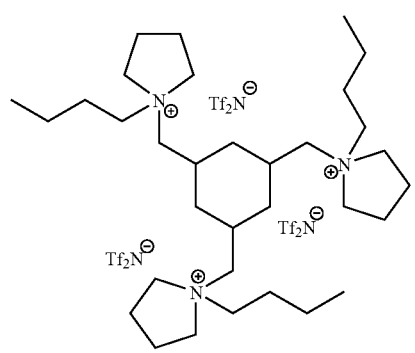
TABLE 7
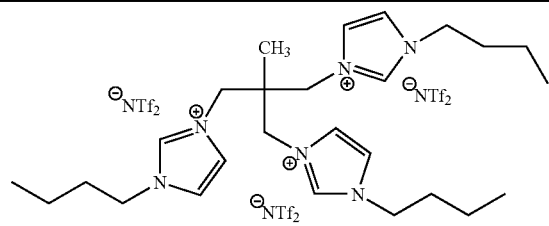
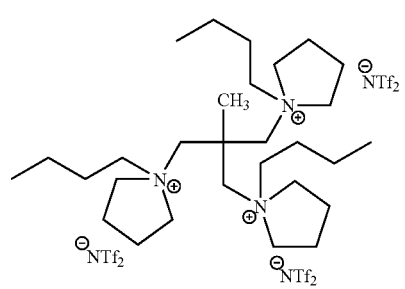
TABLE 8
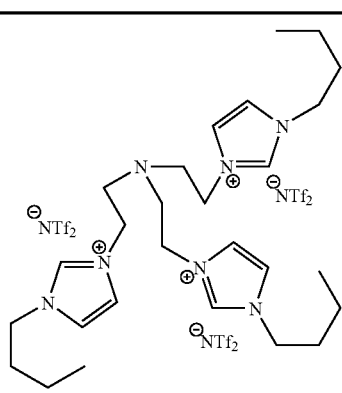
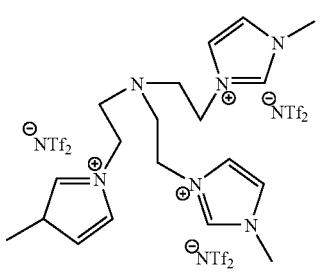
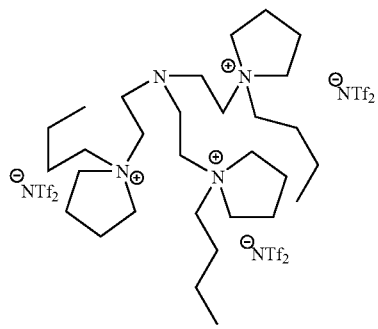

TABLE 8-continued
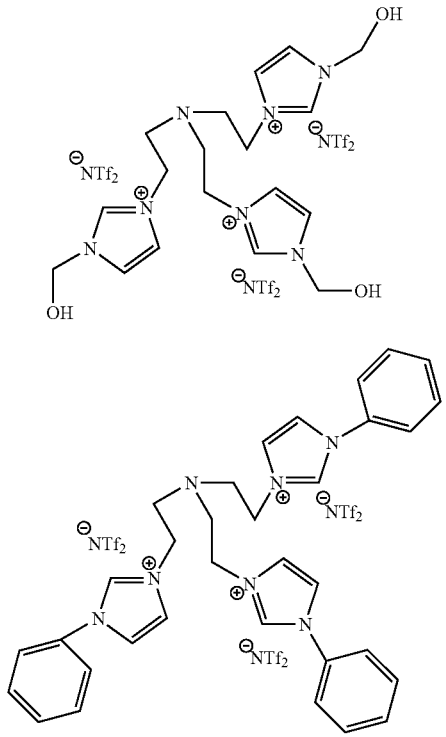
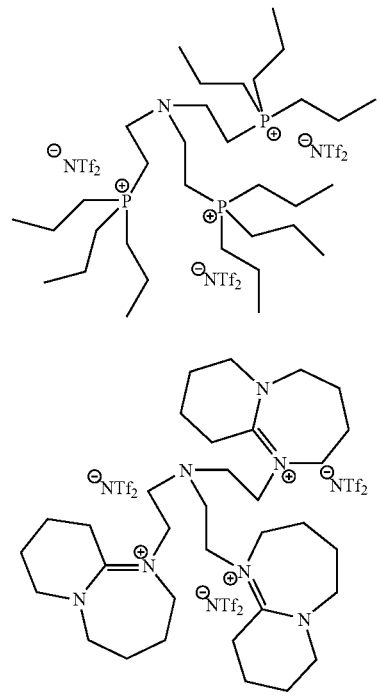
TABLE 9
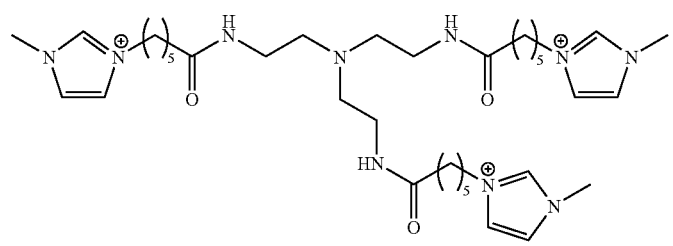
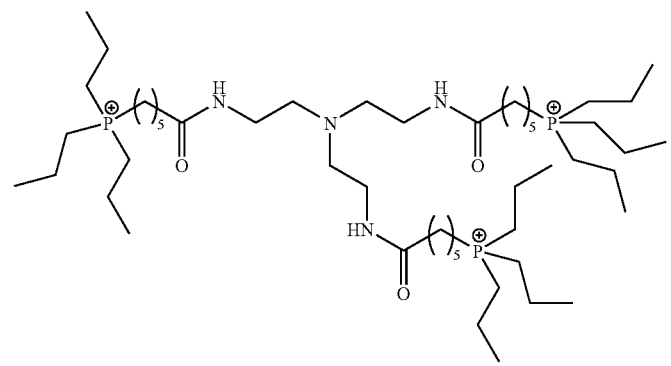

TABLE 10

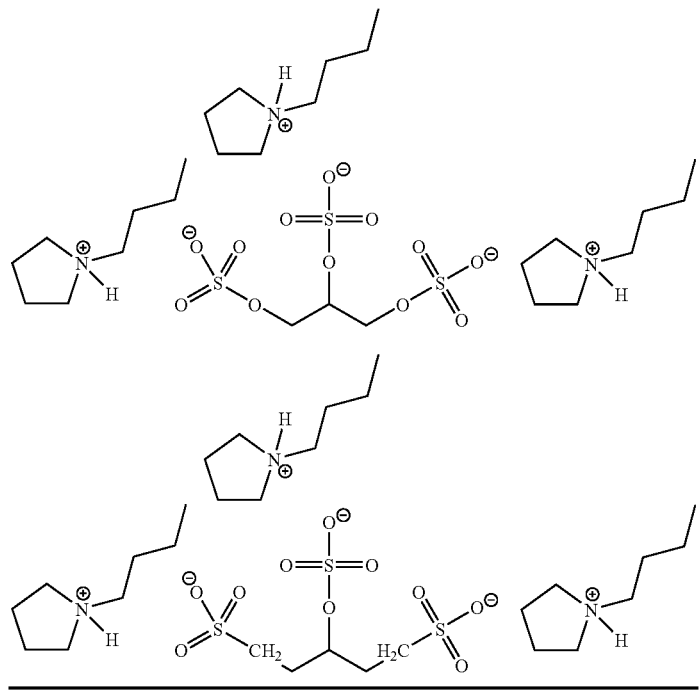

TABLE 11

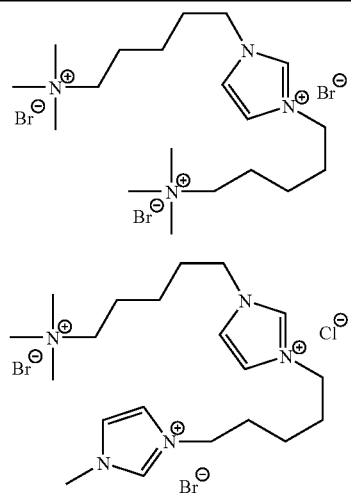

C. Polyionic Liquid Salts as Solvents

This invention is also directed to solvents comprising one or more polyionic liquid salts in accordance with the invention.

In some embodiments, the solvent comprises one polyionic liquid salt.

In other embodiments, the solvent comprises more than one polyionic liquid salt.

The polyionic liquid salts of the present invention can be used in pure or in substantially pure form as carriers or as solvents. "Substantially" in this context means no more than about 10% of undesirable impurities. Such impurities can be other undesired polyionic salts, reaction by-products, contaminants or the like as the context suggests. In an intended mixture of two or more PILS, neither would be considered an impurity. Because they are non-volatile and stable, they can be recovered and recycled and pose few of the disadvantages of volatile organic solvents. Because of their stability over a wide liquid range, in some instances over 400° C., they can be used in chemical synthesis that requires both heating and cooling. Indeed, these solvents may accommodate all of the multiple reaction steps of certain chemical syntheses. Of course, these polyionic liquids may be used in solvent systems with co-solvents and gradient solvents and these solvents can include, without limitation, chiral ionic liquids, chiral non-ionic liquids, volatile organic solvents, non-volatile organic solvents, inorganic solvents, water, oils, etc. It is also possible to prepare solutions, suspensions, emulsions, colloids, gels and dispersions using the polyionic liquids. Polyionic salts in accordance with the invention may be used in any mixture, including different polycations, different polyanions and mixtures of polycations and polyanions. In addition, one or more of the polyionic liquid salts of the invention may be mixed with diionic liquid salts as described in U.S. Patent Publication No. 2006/0025598, the text of which is hereby incorporated by reference.

In addition to discrete polyionic liquid salts, it is also possible to produce polymers of these materials. Polymers may include the polyionic liquid salts within the backbone or as pendant groups and they may be cross-linked or non-cross-linked.

In addition to being useful as solvents and reaction solvents, the polyionic liquid salts of the present invention can be used to perform separations as, for example, the stationary phase for gas-liquid chromatography. Polyionic liquid salts having unsaturated groups can be cross-linked and/or immobilized. For example, polyionic liquid salts can be coated on a capillary (or solid support) and optionally, subsequently polymerized and/or cross-linked.

Indeed, in one aspect of the present invention, there are provided immobilized ionic liquids including one or more high stability polyionic liquid salts (with or without monoionic materials) as stationary phases, particularly in gas chromatography. These stationary phases are highly selective, highly stable, and highly resistant to temperature degradation. These materials can be non-cross-linked (which often means that they are absorbed or adsorbed on a solid support or column), can be "partially" cross-linked or "more highly" cross-linked (which often means that they are "immobilized" on a solid support or column) and can be composed of a mixture of polyionic liquid salts and diionic material and/or monoionic materials or can be made completely of polyionic liquid salts in accordance with the present invention. In the case of non-cross-linked stationary phases, the polyionic salts used may be saturated, unsaturated or a mixture of both. It should be understood, however, particularly if some amount of unsaturated polyionic liquid salts are used, and especially where heat is used to fix the stationary phase, or the stationary phase is heated during use, as in GC, some degree of cross-linking is possible. "Partially" cross-linked stationary phases in accordance with the present invention permit production of a more stable, highly selective stationary phase, allowing for high efficiency separations at temperatures up to approximately 280° C. In "partially cross-linked" stationary phases, there can be a mixture of mono and polyionic species and the amount of polyionic liquid salts used will be equal to or less than the amount of monoionic species used. "More highly" cross-linked stationary phases in accordance with the present invention can provide superior efficiency and stability even at temperatures up to 35° C. and higher. In "more highly cross-linked" stationary phases, the amount of polyionic species (polyionic liquids/salts) will surpass that of any monoionic species. Indeed, preferably, more highly cross-linked stationary phases will be composed substantially exclusively (90% or more) of immobilized polyionic liquid salts in accordance with the invention. Indeed, they are preferably purely polyionic liquid salts. In either case, the monoionic species, diionic species and the polyionic species used preferably include unsaturation. The monoionic species will generally have a single multiple bond, the diionic liquid salts will generally have two or more multiple bonds (double bonds/triple bonds), while the polyionic liquid salts will generally have three or more multiple bonds (double bonds/triple bonds). Of course, the polyionic or diionic species can have but a single unsaturated bond as well. These unsaturated bonds not only allow cross-linking, but also facilitate immobilization. Mixtures of saturated and unsaturated species may also be used, particularly in the case of non-cross-linked stationary phases.

In a particular embodiment, the stationary phases are made from a polyionic species which is chiral and optically enhanced. Moreover, cross-linking and/or immobilization of the ionic liquids in a column as a stationary phase, or to a solid support for SPE, SPME, task-specific SPE or SPME, SPME/MALDI, ion exchange and headspace analysis or other analytical or separation technique, does not appear to affect the selectivity of the stationary phase, thereby preserving its dual nature retention behavior.

And while stationary phases for gas chromatography and in particular capillary GC are one particular aspect of the present invention, the polyionic liquid salts, either alone or in combination with monoionic liquid salts and/or diionic liquid salts, can be used as a stationary phase in other forms of chromatography including, for example, liquid chromatography ("LC") and high performance liquid chromatography ("HPLC"). Not only are the methods of creating stationary phases, solid supports and/or columns containing same contemplated, the stationary phases, solid supports and columns themselves and the use of columns and solid supports containing these stationary phases in chromatography, another analytical or separation techniques are contemplated as specific aspects of the invention.

Thus, one or more polyionic liquid salts in accordance with the present invention can be used in analytical and separation technologies other than chromatography, all of which are considered as part of the present application. For example, polyionic liquid salts in accordance with the present invention can be used in, without limitation, solid phase extraction ("SPE"), solid phase microextraction ("SPME"), task-specific SPME ("TSSPME"), and certain types of mass spectrometry known as solid phase microextraction/MALDI, as well as ion exchange and headspace analysis. The invention includes not only the use of ionic liquid salts and, in particular, polyionic liquid salts in these techniques, but also solid supports to which ionic liquid salts, and in particular, polyionic liquid salts, are absorbed, adsorbed or immobilized as well as sampling devices such as, for example, pipettes, automatic pipettes, syringes, microsyringes and the like incorporating ionic liquid salts, such as polyionic liquid salts, which can be used in such analytical and separation techniques. Solid supports include, without limitation, mixed beds of particles coated with ionic liquid salts. These may be used as chromatographic media or for SPE, SPME, SPME/MALDI and ion exchange analysis. Particles may be composed of, for example, silica, carbons, composite particles, metal particles (zirconia, titania, etc.), as well as functionalized particles, etc. contained in, for example, tubes, pipettes tips, needles, vials, and other common containers.

In yet another embodiment, the present invention provides a polyionic liquid salt ("liquid" meaning liquid salts at either room temperature (25° C.) or at a temperature above the solid/liquid transformation temperature, which may be 400° C. or lower, unless otherwise indicated) having a solid/liquid transformation temperature which is about 40° C. or lower, said polyionic liquid salt including two monoionic groups separated by a bridging group and either two monoionic counterions or at least one polyionic counterion. In one embodiment, the two monoionic groups are both cationic or anionic and in another embodiment, they are germinal (the same). When cationic, it is preferred that the groups are quaternary ammonium, protonated tertiary amine, thionium, phosphonium or arsonium groups which may be substituted or unsubstituted, saturated or unsaturated, linear, branched, cyclic or aromatic. When anionic, the groups are preferably carboxylate, sulfate or sulfonate groups which may be substituted or unsubstituted, saturated or unsaturated, linear, branched, cyclic or aromatic. In a particular embodiment, these polyionic liquid salts include at least one unsaturated bond which can facilitate cross-linking and/or immobilization.

In another embodiment, one or more polyionic liquid salts can be used as a solvent for dissolution, suspension or dispersion of solids or liquid mixed therewith or as a reaction solvent for chemical reactions. Both are intended by the term solvent. In a particular embodiment, a solvent comprises: one or more polyionic liquid salts as noted above having a solid/liquid transition temperature of about 50° C. or lower, more preferably about 40° C. or lower and having a liquid range of about 20° C. or higher; and, in another embodiment, stability is measured by being substantially non-volatile at a temperature of about 20° C. or below. Both polyionic liquid salts and the solvents made therefrom may be chiral and optically enhanced.

D. Devices

This invention is also directed, in part, to a device for chemical separation or analysis comprising a solid support and one or more polyionic liquid salts of the invention which is adsorbed, absorbed or immobilized on the solid support. In a particular embodiment, a device of the invention comprises a syringe, a hollow needle, a plunger, and the solid support being attached to the syringe.

Another embodiment of the present invention is a device useful in chemical separation or analysis comprising: a solid support and one or more polyionic liquid salts as described above adsorbed, absorbed or immobilized thereon. The device may be a column used in HPLC, GC or supercritical fluid chromatography (SFC) wherein the solid support is packed in a chromatographic column or wherein the solid support is a capillary column useful in gas chromatography.

The device may also be a syringe having a hollow needle defining an inner space, the needle being disposed at an end of a barrel and a plunger disposed within the barrel, the solid support being attached, mounted or affixed, irremovable or removable, (collectively "attached") to the syringe such that it may be retracted into the inner space of the needle when the plunger is retracted from the barrel and exposed from within the needle when the plunger is inserted into the barrel. In one embodiment, the syringe is a microsyringe. In some embodiments, the one or more polyionic liquid salts used in these devices also include monoionic materials and/or diionic materials which may be simply mixed therewith or which may be cross-liked to the polyionic liquid salts of the invention. These may be absorbed, adsorbed or immobilized on the solid support. When immobilized, it is preferred that these ionic species include unsaturated groups.

E. Methods of Use

This invention also is directed, in part, to a method of using one or more polyionic liquid salts of the invention in analytical and separation technologies such as, but not limited too, liquid chromatography ("LC"), high performance liquid chromatography ("HPLC"), solid phase extraction ("SPE"), solid phase microextraction ("SPME"), task-specific SPME ("TSSPME"), and mass spectrometry known as solid phase microextraction/MALDI, as well as ion exchange and headspace analysis.

In one other embodiment, there is provided a method of separating one chemical from a mixture of chemicals comprising the steps of providing a mixture of at least one first and at least one second chemical, exposing that mixture to at least one solid support including one or more polyionic liquid salts as described above using a device as described above and retaining at least a portion of the first chemical on the solid support for some period of time. "Retaining" in this context does not mean permanently. Separation can occur in a syringe device by removal of the device from the sample or ejection of the second chemical. In the case of a chromatography column, the first chemical will be absorbed or adsorbed at a different rate than the second chemical, which may be at a greater rate or a lower rate, thus resulting in separation. Both are moved through the column by a mobile phase, which can be a liquid or a gas and their interaction with the stationary phase (the ionic liquid materials on the solid support) at different rates causes separation. This is what is meant by "retention" in the context of chromatography. However, in certain types of chromatography, it is also possible that the first chemical is bound to the stationary phase while the second chemical is not and is carried through the column by the mobile phase until it elutes. The first chemical can be eluted or removed separately and this is also embraced by the word "retained."

The ionic liquid can be coated via the static coating method at 40° C. using coating solution concentrations ranging from 0.15-0.45% (w/w) using solutions of methylene chloride, acetone, ethyl acetate, pentane, chloroform, methanol or mixtures thereof. After coating of the ionic liquid is complete, the column is purged with helium and baked up to 100° C. The efficiency of naphthalene (other molecules such as n-hydrocarbons or Grob Test Mixture can also be used for this purpose) is then evaluated to examine the coating efficiency of the monomer ionic liquid stationary phase. If efficiency is deemed sufficient, the column is then flushed with vapors of azo-tert-butane, a free radical initiator, at room temperature. After flushing with the vapors, the column is then fused at both ends and heated in an oven using a temperature gradient up to 200° C. for 5 hours. The column is gradually cooled and then re-opened at both ends, and purged with helium gas. After purging with helium gas overnight, the column is then heated and conditioned up to 200° C. After conditioning, the column efficiency is then examined using naphthalene at 100° C. and the stationary phase coated layer examined under a microscope. Note that the cross linking process can, and often does, also cause immobilization. "Immobilized" in the context of the invention means covalently or ionically bound to a support or to another ionic liquid (including polyionic liquid salts) or both. This is to be compared with ionic liquids which may be absorbed or adsorbed on a solid support. Solid support in these particular instances was intended to include columns (e.g., the walls of the columns).

It is not necessary, however, to cross-link these materials prior to their use in GC. They may be adsorbed or absorbed in a column, or indeed on any solid support. However, at higher temperatures, their viscosity may decrease and they can, in some instances, flow and collect as droplets which can change the characteristics of the column. Immobilization or partial cross-linking also reduces the vapor pressure of the stationary phase film which translates into lower column bleed thereby increasing the useful upper temperature limit of the phase and column.

Another method involves adding up to 2% of the monomer weight of 2,2'-azobisisobutyronitrile ("AIBN") free radical initiator to the coating solution of the monomer. The capillary column is then filled with this solution and coated via the static coating method. After coating, the capillary column is then sealed at both ends and placed in an oven and conditioned up to 200° C. for 5 hours. The column is gradually cooled and then reopened at both ends, and purged with helium gas. After purging with helium gas overnight, the column is then heated and conditioned up to 200° C. After conditioning, the column efficiency is then examined using naphthalene at 100° C. and the stationary phase coated layer examined under a microscope.

In addition to the free radical polymerization of an alkene, other polymerization reactions involving other functional groups either attached to the aromatic ring of the cation, the linkage chain connecting two cations (to form a dication), or the anion can be achieved. Examples of such reactions may include cationic and anionic chain growth polymerization reactions, Ziegler-Natta catalytic polymerization, and step-reaction polymerization. The use of two different monomers to form copolymers through addition and block copolymerization can also be achieved. Additionally, condensation polymerization can be used to connect through functional groups such as amines and alcohols. All polymerization and cross-linking reactions discussed in the following 2 references can be used: "Comprehensive Polymer Science—The Synthesis, Characterization, Reactions and Applications of Polymers" by Sir Geoffrey Allen, F R S; and "Comprehensive Organic Transformations: a guide to functional group preparations" by Richard C. Larock. 2nd Edition. Wiley-VCH, New York. Copyright, 1999.

In accordance with another aspect of the present invention, there is provided a process which includes the free radical reaction of ionic liquid monomers to provide a more durable and robust stationary phase, as well as the cross-linked and/or immobilized stationary phases and the columns that include same. By partially cross-linking the ionic liquid stationary phase using a small percentage of free radical initiator, high efficiency capillary columns are produced that are able to endure high temperatures with little column bleed. It was found that low to moderate temperature separations (30° C.-280° C.) can be carried out with high selectivity and efficiency using special partially cross-linked ionic liquid stationary phase mixtures. These stationary phases retain their "gelatinous," "semi liquid," amorphous state. For separations conducted at higher temperatures (300° C.-400° C.), more highly cross-linked/immobilized stationary phases are well-suited to provide high selectivity and efficient separations with low column bleed. The effect of different functionalized ionic liquid salt mixtures and initiator concentrations is studied for these two types of stationary phases. The accomplished goal is to maximize their separation efficiency, thermal stability, and column lifetime, without sacrificing the unique selectivity of the stationary phase.

The following materials can be used to prepare cross-linked stationary phases comprising polyionic liquid salts in accordance with the present invention: 1-vinylimidazole, 1-bromohexane, 1-bromononane, 1-bromododecane, 1,9-dibromononane, 1,12-dibromododecane, 1-bromo-6-chlorohexane, 1-methylimidazole, N-Lithiotrifluoromethanesulfonimide, 2,2'-Azobisisobutyronitrile (AIBN), dichloromethane and ethyl acetate.

It has been demonstrated previously that room temperature ionic liquids act as broadly applicable, superb gas chromatographic stationary phases in that they exhibit a dual nature retention behavior. Consequently, ionic liquid stationary phases have been shown to separate, with high efficiency, both polar and nonpolar molecules on a single column. By producing stationary phases that are either partially or highly cross-linked, it is of interest to ensure that the solvation thermodynamics and solvation interactions inherent to ionic liquids are still retained by their immobilized analogues.

Of course, ionic liquids and in particular the polyionic liquid salts of the present invention can be used in other separation and analytical techniques. Their range of applicability is in no way limited to chromatography. One technique in which these materials can be used is Solid Phase Extraction ("SPE"). In SPE, a sample contains an impurity or some other compound or analyte to be separated, identified and/or quantified. This sample can be placed into a container in which polyionic liquid salts of the present invention can be present in, and more broadly, ionic liquids in an immobilized form. Ionic liquid materials can be bound (immobilized) to the walls of the container, adsorbed, or absorbed onto a bead or other structure so as to form a bead or other structure which may rest at the bottom of the container or be packed throughout the container much as a liquid chromatography column can be packed with stationary phase. Alternatively, the ionic liquids and in particular polyionic liquid salts of the present invention can be immobilized by cross-linking or an analogous immobilization reaction as described herein on some sort of other solid support such as a bead, particles and/or other chromatographic media used in chromatography as described previously. These beads can also be placed at the bottom of, or can fill a container, much as a packed column used for liquid chromatography. Of course, the solid support can be any structure placed anywhere within the container.

In a particular embodiment, the container is actually a syringe where the ionic liquid and/or polyionic liquid salts are affixed or disposed in one fashion or another at the base of the syringe, much as a filter. When the needle of the syringe is placed in a sample and the plunger is withdrawn, vacuum is formed drawing the sample up into the barrel of the syringe. This material would pass through at least one layer of ionic liquid and, in particular, polyionic liquid salts in accordance with the present invention, which would bind at least one of the components of the liquid. The sample liquid could then be spilled out or the plunger depressed to eject it, the latter forcing the sample back through the ionic liquid or polyionic liquid salts positioned at the bottom of the barrel.

The liquid can be analyzed either for the presence of certain materials or the absence of the material retained by the ionic liquid or polyionic liquid salts of the present invention. Alternatively, the retained materials can be removed (such as by placing the materials in a different solvent) or not and analyzed analytically by other means. The same technique may be used in a preparative fashion and/or as a means of bulk purification as well.

Another technique in which immobilized ionic liquids and polyionic liquid salts of the present invention may be used is solid phase microextraction or SPME. Broadly speaking, in these techniques, a separation material (in this case an ionic liquid or in particular a polyionic liquid salt in accordance with the present invention or ionic liquids mixed with adsorbents, particles and other chromatographic media) is absorbed, adsorbed or immobilized in one way or another on a fiber (e.g., polydimethylsiloxane/divinylbenzene (PDMS/DVB) fiber) or some other solid support which is applied to the plunger as a coating or as a sheet generally attached to a plunger in a microsyringe such as usually used in gas chromatography. The diionic liquid salts of the invention can also be immobilized and attached directly without any separate solid support other than the plunger. This can be done using, for example, a film directly. In the case of the invention, immobilized ionic liquids and absorbed, adsorbed and immobilized polyionic liquid salts are contemplated. The plunger is depressed, exposing the fiber and the fiber is then dipped into the sample of interest. The plunger can then be withdrawn to pull the fiber back into the barrel of the syringe, or at least the barrel of the needle for protection and transport. The syringe can then be injected through the septum of a gas chromatograph or some other device and the fiber thereby inserted into the column by redepressing the plunger of the microsyringe. The heat used in GC then volatilizes or otherwise drives the bound sample off where it is carried by the mobile phase through the GC column, allowing for separation and/or identification. It can also be eluted by a liquid mobile phase in an HPLC injector or unbuffer capillary electrophoresis. Immobilized ionic liquids and diionic liquid salts of the present invention may also be used in conjunction with the coated stir bar technology, which is a higher capacity version of SPME. Some embodiments of this coated stir bar technology are sold under the trademark TWISTER.

More specifically, solid phase microextraction is a technique in which a small amount of extracting phase (in this case an ionic liquid and preferably a polyionic liquid salt in accordance with the present invention) is disposed on a solid support, which was then exposed to a sample for a period of time. In situations where the sample is not stirred, a partitioning equilibrium between a sample matrix and the extraction phase is reached. In cases where convection is constant, a short time pre-equilibrium extraction is realized and the amount of analyte extracted is related to time. Quantification can then be performed based on the timed accumulation of analysis in the coating. These techniques are usually performed using open bed extraction concepts such as by using coated fibers (e.g., fused silica similar to that used in capillary GC or capillary electrophoresis, glass fibers, wires, metal or alloy fibers, beads, etc.), vessels, agitation mechanism discs and the like. However, in-tube approaches have also been demonstrated. In-tube approaches require the extracting phase to be coated on the inner wall of the capillary and the sample containing the analyte of interest is subject to the capillary and the analytes undergo partitioning to the extracting phase. Thus, material can be coated on the inner wall of a needle, for example, and the needle injected without the need for a separate solid support.

FIG. 1 shows an example of an SPME device 1. A stainless steel microtube 40 having an inside diameter slightly larger than the outside diameter of, for example, a fuse silica rod 60 is used. Other inert metals, such as Nitinol (nickel/titanium alloy) can be also employed in SPME instead of stainless steel. Typically, the first 5 mm is removed from a 1.5 cm long fiber, which is then inserted into the microtubing. High temperature epoxy glue is used to permanently mount the fiber. Fibers can also be crimped to the syringe plunger without using adhesives. Sample injection is then very much like standard syringe injection. Movement of the plunger 30 allows exposure of the fiber 60 during extraction and desorption and its protection in the needle 20 during storage and penetration of the septum. 10 shows the barrel of the microsyringe, 50 shows the extreme end of the stainless steel microtube in which the silicon fiber is mounted.

Figure 2:
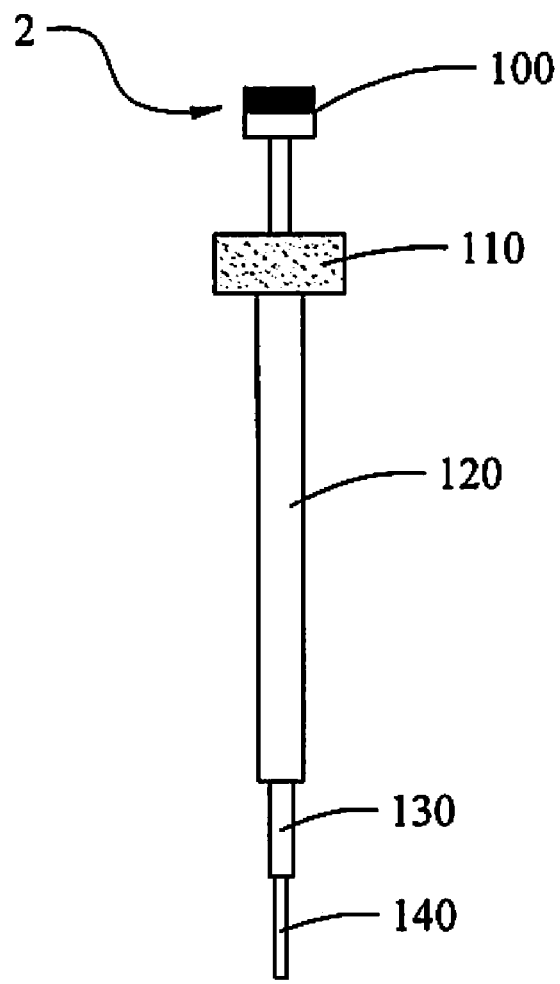
FIG. 2 is another embodiment of a syringe useful for SPME and SPME/MALDI mass spectrometry.

Another embodiment of a syringe useful for SPME in accordance with the present invention is illustrated in FIG. 2. Syringe 2 can be built from a short piece of stainless steel microtubing 130 to hold the fiber. Another piece of larger tubing 120 works as the needle. A septum 110 is used to seal the connection between the microtubing 130 and the needle 120. The silica fiber 140 is exposed through one end of the microtubing 130 and the other end is blocked by a plunger 100. Withdrawing plunger 100 retracts microtubing 130 and the fiber 140 into the barrel of the device, the needle 120. Depressing plunger 100 reverses this process. These are but exemplary structures and any syringe device, including those containing a needle or tube with the ionic liquid immobilized on the inner surface thereof, are also contemplated.

In addition, one or more polyionic liquid salts in accordance with the present invention can be immobilized by being bound or cross-linked to themselves and/or to a solid support as previously discussed in connection with manufacturing capillary GC columns. To do so, however, the species used should have at least one unsaturated group disposed to allow reaction resulting in immobilization.

Another type of SPME technique is known as task specific SPME or TSSPME. Task specific SPME allows for the separation or removal, and therefore the detection of particular species. These can include, for example, mercury and cadmium, although the technique is equally applicable to other materials. The concept is exactly the same as previously described with regard to SPME. However, in this instance, the ionic liquids or polyionic liquids used are further modified such that they will specifically interact with a particular species. Those shown below, for example, may be used in the detection of cadmium ($Cd^{2+}$) and/or mercury ($Hg^{2+}$). The first monocationic material can be coated, absorbed or adsorbed onto a fiber as previously discussed. A polyionic liquid salt can also be absorbed or adsorbed in known fashion.

Finally, a particular sample can be suspended in a matrix that includes ionic liquids and preferably polyionic liquid salts in accordance with the present invention. This matrix can be loaded or immobilized on the fiber of an SPME syringe as described above and then injected into a mass spectrometer to practice a technique known as SPME/MALDI mass spectrometry.[55] The matrix is exposed to a UV laser. This causes the volatilization or release of the sample much as heat does in a GC. This allows the sample to enter mass spectrometer where it can be analyzed.

Polyanionic anions can also be used with either monocations or polycations to form a variety of different ionic liquid combinations. When a polycation is used, anyone is used as charge balance must be preserved. The polyanionic anions can be of the dicarboxylic acid type (i.e., succinic acid, nonanedioic acid, dodecanedioic acid, etc).

In a further embodiment, the invention provides a method of detecting a charged molecule using electrospray ionization-mass spectrometry (ESI-MS). The one or more polyionic liquid salts may be used as a reagent to detect charged anions in the positive mode by ESI-MS. In the method, a suitable amount of the polyionic species of the invention having the opposite charges is added to the sample. The charged species in the sample to be detected may be, but need not be polyionic as well, e.g., having +2 or −2 charges. The polyionic species and the charged molecule form a salt complex. The salt complex is generally a solid. The polyionic species contains at least one more opposite charge than the charged molecule to be detected such that the complex has a net charge. Preferably, the polyionic species contains no more than one opposite charge than the charged molecule to be detected such that the complex has a net charge of +1 or −1. However, +2 or −2 or even higher charge difference can also be used. The complex is then detected using ESI-MS. The formation of the complex converts the charged molecule into an ion having a higher mass to charge ratio m/z, which can be transferred by ESI more efficiently due to mass discrimination. Benefits of using the polyionic liquid salts as such reagent include, without limitation, (a) moving anions to a higher mass range out of the low mass regions dominated by chemical noise, (b) increasing sensitivity for anions with masses near the low mass cutoff of quadrupole instruments (e.g. traps), and (c) help discriminate against interferences with the same mass to charge ratio. ESI-MS may be used alone or in combination with a separation method, such as those discussed above.

In another particular embodiment, the method includes selecting a polyionic species that has a desired composition and structure, e.g., a desired number of charged groups, a desired charged group structure and a desired mass, or a combination thereof. The charged groups in the polyionic species can be selected based on the composition and structure of the charged molecule to be detected. Preferably, the polyionic species is specific for the charged molecule to be detected. Thus, it is preferable that the charged group of the polyionic species is such that it binds strongly with the charged molecule to be detected. More preferably, the charged group of the polyionic species is such that it does not bind strongly with other charged molecules, in the sample. Using a polyionic species that is specific for a charged molecule of interest allows high selectivity in detecting the charged molecule. Use of polyionic species having two or more different ionic groups may offer particular advantages in tailoring the affinities for different molecules for detection.

The mass of the polyionic species can be selected to achieve optimal detection by the mass spectrometer. In general, a polyionic species having a large mass is used. In a particular embodiment, the polyionic species is selected such that the complex has a m/z at least 50. Most commercial single quadruple mass spectrometers are designed to have their optimum performance at m/z values significantly higher than 100. Thus, in another particular embodiment, the polyionic species is selected such that the complex has a m/z significantly higher than 100, e.g., at least about 200, at least about 300, or at least about 400. A person skilled in the art will understand that the mass of the polyionic species depends on the sizes of the charged groups as well as the bridging group. One or more of these can be varied to obtain a polyionic species of desired mass. More preferably, the polyionic species has no more than one opposite charge than the charged molecule to be detected such that the complex has a net charge of +1 or −1, i.e., z=1. The lower is the value of z; the higher is m/z, which leads to optimum detection performance. For example, to detect a −2 charged molecule, a tricationic species that forms with the charged molecule a complex having a net charge of +1 is preferably used.

In a further embodiment, the method includes selecting a polyionic liquid salt that dissociates with high yield. This can be achieved by selecting a polyionic liquid salt containing suitable counterions. In cases where a polyionic liquid salt having desired ionic groups but less desirable counterions, it can be converted to a polyionic liquid salt containing the desired counterions by ion exchange. In a specific embodiment, a fluoride salt of a cationic species is used as a reagent for ESI-MS, which, if not available, can be converted from a dihalide, a bromide or an iodide salt by anion exchange.

In another embodiment, the method further includes a step of performing ion chromatography prior to the addition of the polyionic species.

In a particular embodiment, the invention provides a method of detecting a charged molecule of −2 charge by mass spectrometry, particularly ESI-MS, using a tricationic species of the invention. Any one of the tricationic species described above can be used.

In another particular embodiment, the invention provides a method of detecting a charged molecule of +2 charge by mass spectrometry, particularly ESI-MS, using a trianionic species of the invention. Any one of the trianionic species described above can be used.

In another particular embodiment, the invention provides a method of detecting a plurality of different charged molecules by mass spectrometry using a plurality of different diionic species of the invention. Each of the diionic species is selected to specifically bind one of the different charged molecules. Preferably, the different diionic species have different masses such that the complexes formed with their respective charged molecules can be detected separately. In one embodiment, the plurality of different charged molecules are different charged molecules of +2 or −2, and the plurality of different polyionic species are trianionic species or tricationic species, respectively.

Mass spectrometry can be carried out using standard procedures known in the art.

In another aspect of the present invention, a mixture is provided comprising at least one polyionic liquid salt of the invention and traditional stationary phase material such as but not limited to polysiloxanes, PEGs, methylpolysiloxances, phenyl substituted methylpolysiloxane, nitrile substituted methylpolysiloxane and carbowax. Such mixture (mixed stationary phase or "MSP") can be used as a stationary phase in chromatography such as gas chromatography, liquid chromatography and high performance liquid chromatography as well as in SPE and SPME. Both polycationic liquid salt and polyanionic liquid salt can be used for this purpose. The MSPs can be non-cross-linked (e.g., absorbed or adsorbed on a solid support or column), can be "partially" cross-linked or "more highly" cross-linked (i.e., immobilized on a solid support or column). The polyionic liquid salt may also be cross-linked or otherwise reacted with the traditional stationary phase material or merely mixed therewith.

Thus, in one embodiment, the invention provides MSPs comprising at least one of the polyionic liquid salts of the invention and at least one traditional stationary phase material at a suitable proportion. Appropriate combinations of the polyionic liquid salt(s) and the traditional stationary phase material(s) for producing the MSP is based on the particular application as are the proportions of the polyionic liquid salt(s) and the traditional stationary phase material(s) in the MSP. In a particular embodiment, the ratio of the polyionic liquid salt and the traditional stationary phase material in the MSP is from about 1:9 (i.e., about 10% of polyionic liquid salt and 90% of traditional stationary phase material) to about 9:1 (i.e., about 90% of polyionic liquid salt and about 10% of traditional stationary phase material), about 1:3 (i.e., about 25% of polyionic liquid salt and about 75% of traditional stationary phase material) to about 3:1 (i.e., about 75% of polyionic liquid salt and about 25% of traditional stationary phase material), about 1:2 (i.e., about 33% of polyionic liquid salt and about 67% of traditional stationary phase material) to about 2:1 (i.e., about 67% of polyionic liquid salt and about 33% of traditional stationary phase material), or about 1:1 (i.e., about 50% of polyionic liquid salt and about 50% of traditional stationary phase material) (w/w). Chromatography employing MSP may perform better, e.g., having higher selectivity, than chromatography employing polyionic liquid salts or the traditional stationary phase alone. As an example, an MSP comprising a simple mixture of about 67% (dibutyl imidazolium)$_2$(CH$_2$)$_9$ and about 33% of methylpolysiloxance with about 5% phenyl substitution was prepared and used to coat a column. This MSP was shown to exhibit better separation of an essential oil. Cross-linked version of the MSP can also be used.

In addition, the invention also provides methods of preparing MSPs, solid supports and/or columns containing same, the MSPs, solid supports, syringes, tubes, pipettes tips, needles, vials, and columns themselves, and the use of columns and solid supports containing such MSPs in chromatography and other analytical or separation techniques such as those described elsewhere herein.

EXAMPLES

The following examples are merely illustrative, and not limiting to this disclosure in any way. The production of polyionic liquid salts is described in Examples 1-19 below.

Example 1

Synthesis of C3 Symmetric Phenyl and Imidazolium Based-Tricationic Liquid Salt

The ionic compound with bromide was obtained by refluxing 1,3,5-tris(bromomethyl)benzene and 1-butylimidazole in 1,4-dioxane. The compound with the anion of Tf$_2$N is a room temperature ionic liquid, which was synthesized by the metathesis reaction of the bromide compound with LiNTf$_2$ (Lithium trifluoromethanesulfonimide) in water.

Scheme 1

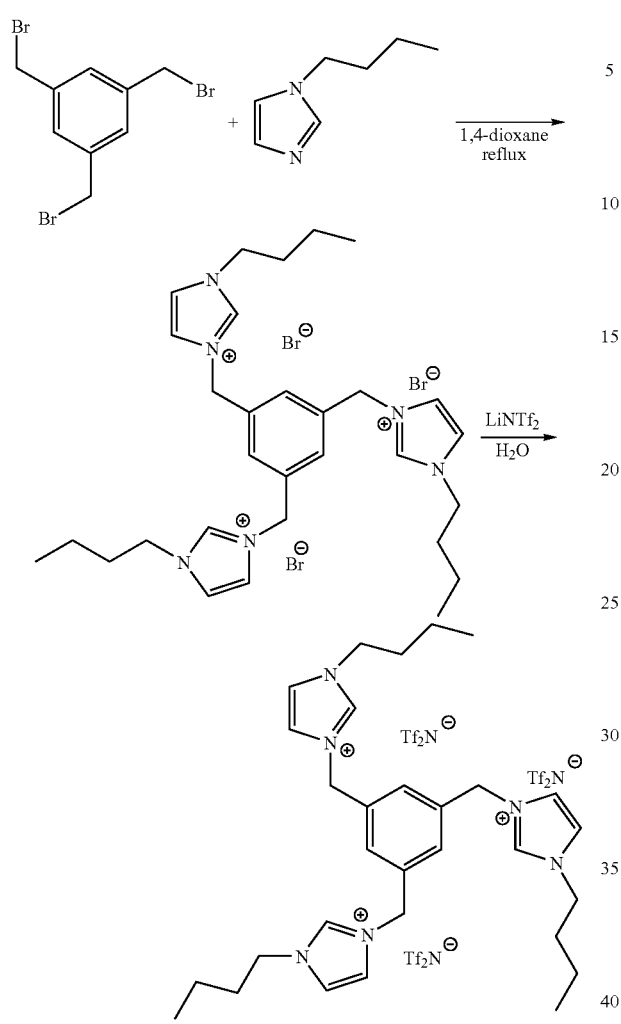

Example 2

Synthesis of C3 Symmetric Phenyl and Pyrrolidinium-Based Tricationic Liquid Salt The ionic compound with bromide was obtained by refluxing 1,3,5-tris(bromomethyl)benzene and 1-butylpyrrolidine in 1,4-dioxane. The compound with the anion of $Tf_2N$ is a room temperature ionic liquid, which was synthesized by the metathesis reaction of the bromide compound with $LiNTf_2$ (Lithium trifluoromethanesulfonimide) in water.

Scheme 2

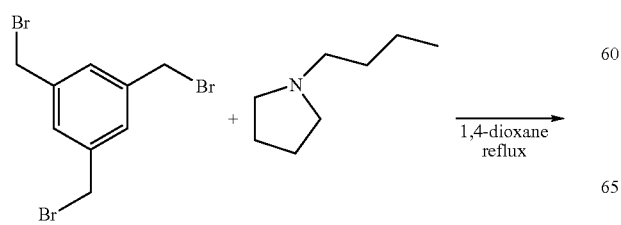

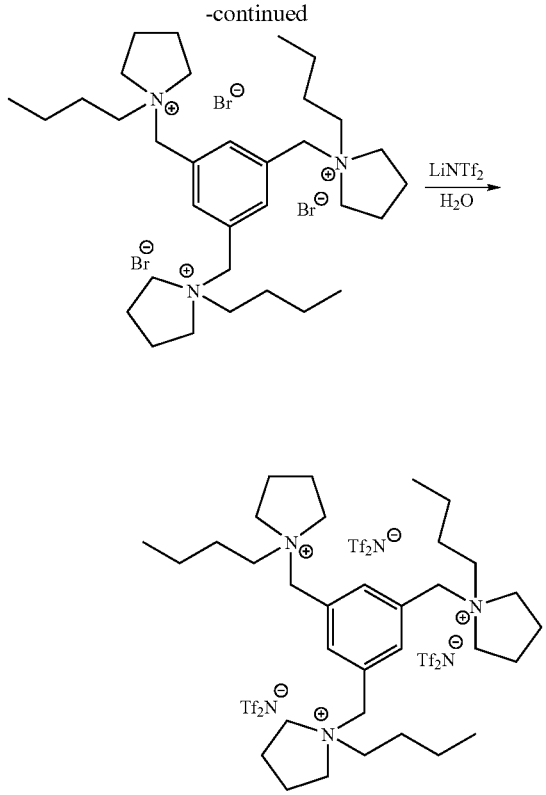

Following similar synthetic procedures, the phosphonium or pyridium-based ionic liquids of the invention can be obtained.

Example 3

Synthesis of Cyclohexane and Imidazolium-Based Tricationic Liquid Salt

The intermediate of 1,3,5-tris(bromomethyl)cyclohexane is synthesized as shown in Scheme 3. Then, the ionic compound with bromide is obtained by refluxing 1,3,5-tris(bromomethyl)-cyclohexane and 1-butylimidazole in 1,4-dioxane. The synthesis of the compound with the anion of $NTf_2$ involves the metathesis reaction of the bromide compound with $LiNTf_2$.

Scheme 3

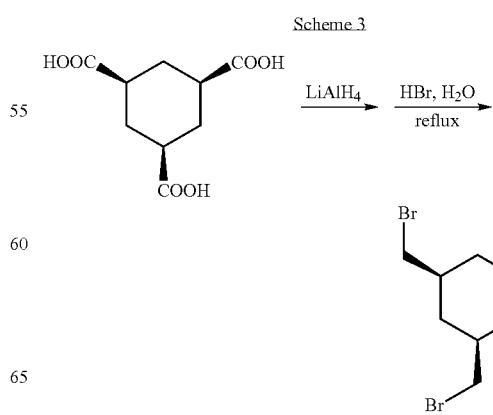

-continued

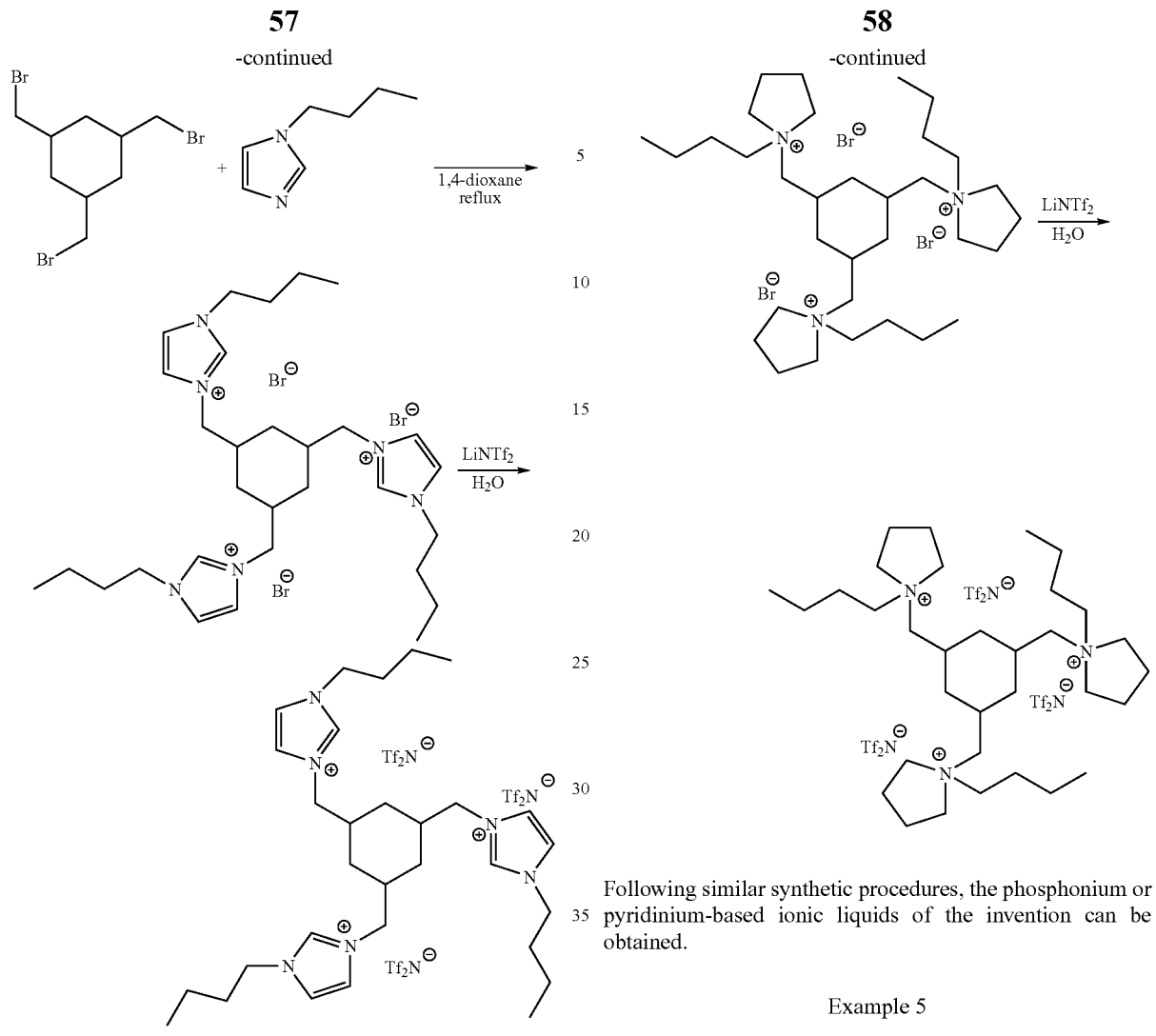

Example 4

Synthesis of Cyclohexane and Pyrrolidinium-Based Tricationic Liquid Salt

For an example, as shown in Scheme 4, the ionic compound with bromide is obtained by refluxing 1,3,5-tris(bromomethyl)cyclohexane and 1-butylpyrrolidine in 1,4-dioxane. The compound with the anion of NTf$_2$ is synthesized by the metathesis reaction of the bromide compound with LiNTf$_2$ in water.

Following similar synthetic procedures, the phosphonium or pyridinium-based ionic liquids of the invention can be obtained.

Example 5

Synthesis of Central Carbon Based-Tricationic Liquid Salt

The ionic compound with chloride is obtained by refluxing the commercially available 1,3-dichloro-2-(chloromethyl)-2-methylpropane and 1-butylimidazole in 1,4-dioxane. The compound with the anion of NTf$_2$ is synthesized by the metathesis reaction of the chloride compound with LiNTf$_2$.

Scheme 5

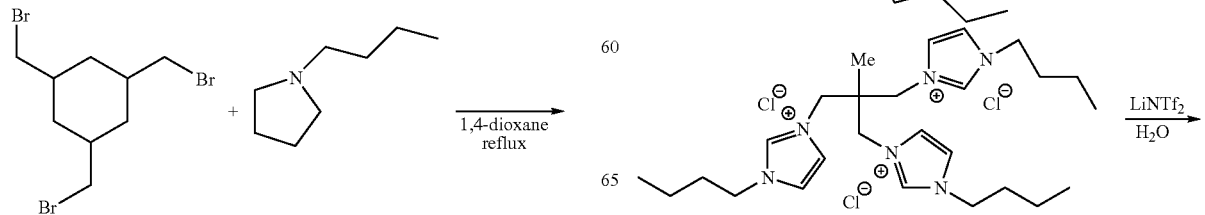

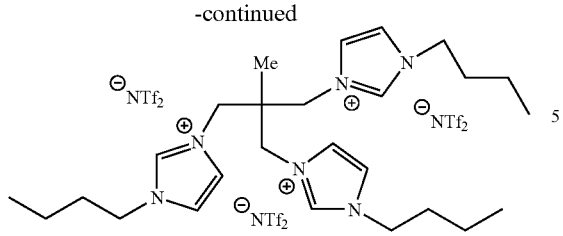

Example 6

Synthesis of Central Carbon Based-Tricationic Liquid Salt

The ionic compound with chloride is obtained by refluxing 1,3-dichloro-2-(chloromethyl)-2-methylpropane and 1-butylpyrrolidine in 1,4-dioxane. The compound with the anion of $NTf_2$ is synthesized by the metathesis reaction of the chloride compound with $LiNTf_2$.

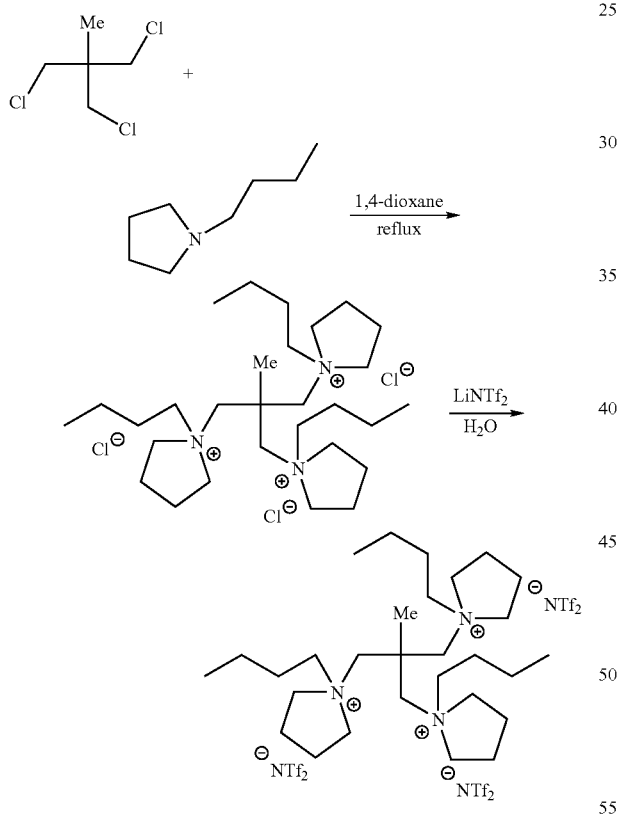

Following similar synthetic procedures, the phosphonium or pyrrolidinium-based ionic liquids of the invention can be obtained.

Example 7

Synthesis of Central Nitrogen Based-Tricationic Liquid Salt

The ionic compound with chloride is obtained by refluxing the commercially available tris(2-chloroethyl)amine hydrochloride and 1-butylimidazole in 2-propanol. The tricationic compound with the anion of $NTf_2$ is synthesized by the metathesis reaction of the chloride compound with $LiNTf_2$ in NaOH water solution.

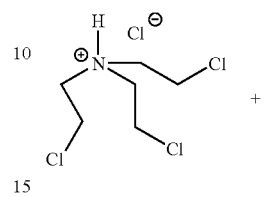

Example 8

Synthesis of Central Nitrogen Based-Tricationic Liquid Salt

For an example, as shown in Scheme 8, the ionic compound with chloride is obtained by refluxing tris(2-chloroethyl) amine hydrochloride and 1-butylpyrrolidine in 2-propanol. The tricationic compound with the anion of $NTf_2$ is synthesized by the metathesis reaction of the chloride compound with $LiNTf_2$ in NaOH water solution.

Scheme 8

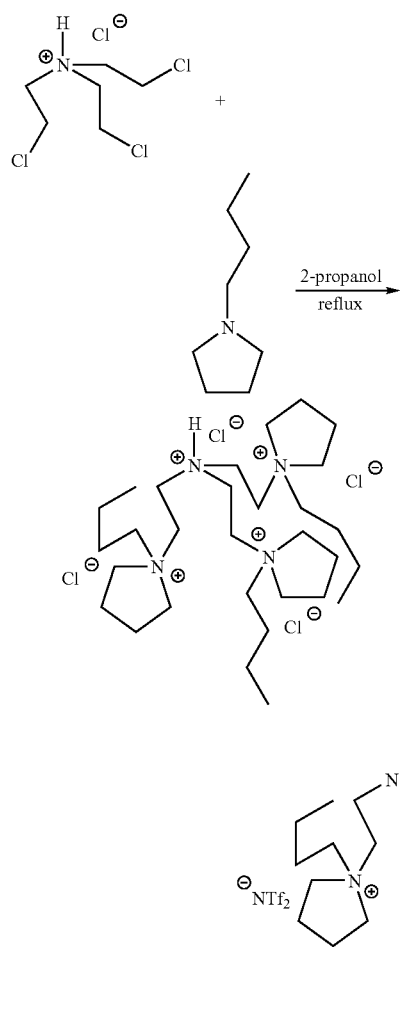

Following similar synthetic procedures, the phosphonium or pyrrolidinium-based ionic liquids of the invention can be obtained.

Example 9

Synthesis of Tricationic Chiral Liquid Salt

The ionic compound with bromide is obtained by refluxing 1,3,5-tris(bromomethyl)benzene and (S)-(1-methylpyrrolidin-2-yl)-methanol in 1,4-dioxane. Then, the ionic compound with the desired anion is synthesized by the metathesis reaction.

Scheme 9

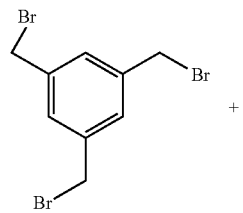

+

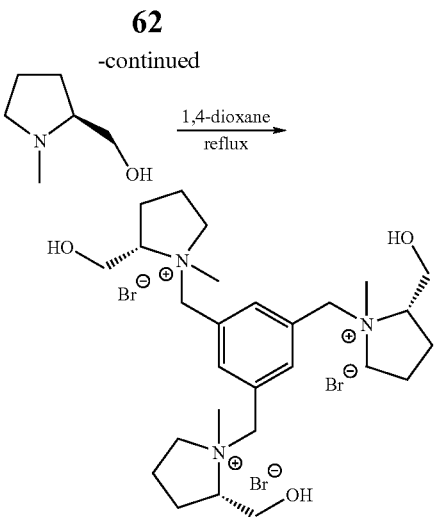

Example 10

Synthesis of Tricationic Chiral Liquid Salt

The ionic compound with bromide is obtained by refluxing 1,3,5-tris(bromomethyl)benzene and (S)-2-dimethylamino-3-methyl-butan-1-ol in 1,4-dioxane. Then, the ionic compound with the desired anion is synthesized by the metathesis reaction.

Scheme 10

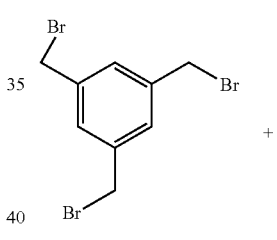

+

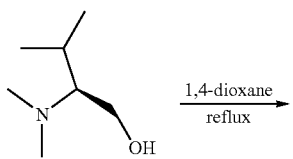

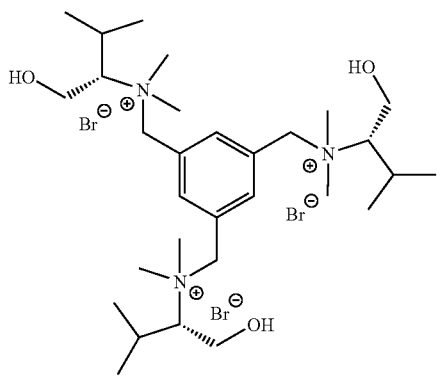

Example 11

Synthesis of Tricationic Chiral Liquid Salt

The ionic compound with bromide is obtained by refluxing 1,3,5-tris(bromomethyl)benzene and (R,R)-2-dimethylamino-1-phenyl-propan-1-ol in 1,4-dioxane. Then, the ionic compound with the desired anion is synthesized by the metathesis reaction.

Scheme 11

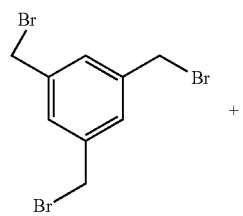

Example 12

Synthesis of C2 Symmetric Central Phenyl-Based Liquid Salt 1,2,3-Tris-bromomethyl-benzene is synthesized as shown in Scheme 12. Then, the C2 symmetric trigeminal tricationic liquids are obtained by the similar synthetic procedures as described in Example 1.

Scheme 12

Example 13

Synthesis of Unsymmetric Central Phenyl-Based Liquid Salt 1,2,4-Tris-bromomethyl-benzene is synthesized as shown in Scheme 13. Then, the unsymmetrical trigeminal tricationic liquids 6a-d are obtained by the similar synthetic procedures as described in Example 1.

Scheme 13

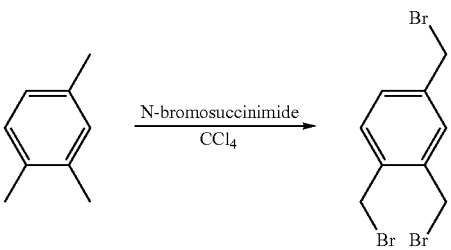

Example 14

Synthesis of a Branched Tetrageminal Tetracationic Liquid Salt

As shown in Scheme 14, the tetracationic compound with bromide is obtained by refluxing butylimidazole and 1,2,4,5-tetrakis(bromomethyl)benzene in 1,4-dioxane. Then, the ionic liquid compound with the desired anion is synthesized by the metathesis reaction.

Scheme 14

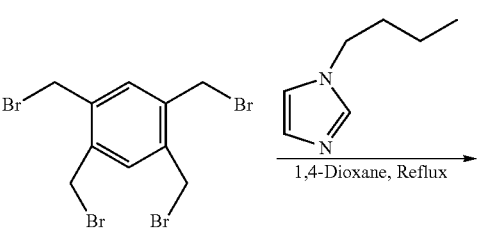

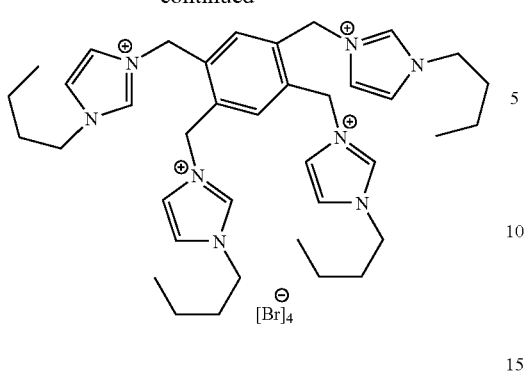

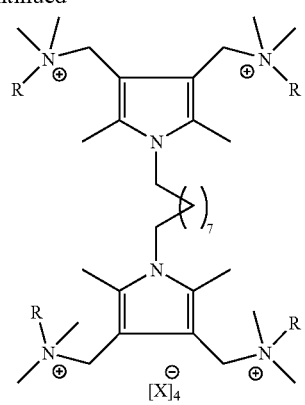

Example 15

Synthesis of a Tetracationic Liquid Salt Based on Ammonium

As shown in Scheme 15, the tetracationic compound based on ammonium is synthesized by the quaternisation reaction of haloalkane and Mannich base of 2,5-dimethylpyrrole. Then, the ionic liquid compound with the desired anion is synthesized by the metathesis reaction.

Scheme 15

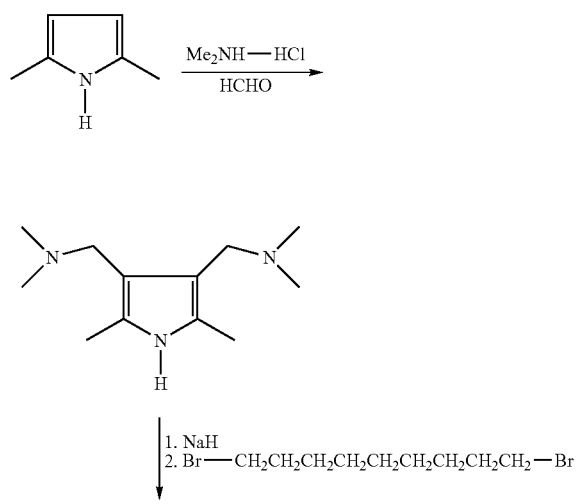

Example 16

Synthesis of a Trianionic Liquid Salt

As shown in Scheme 16, the triol compound is sulfated by chlorosulfonic acid. Then, the sulfate-based trianionic ionic liquid is obtained by an acid-base neutralization reaction with tertiary anime.

Scheme 16

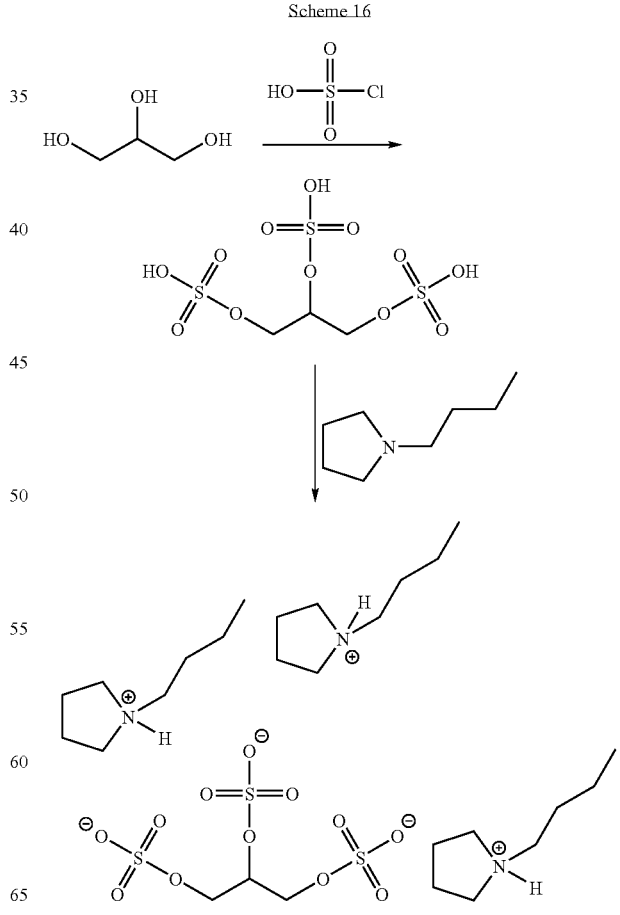

Example 17

Synthesis of a Linear Trigeminal Tricationic Liquid Salt

As shown in Scheme 7, the tricationic compound with bromide is obtained by reactions of sodium imidazole and (5-bromopentyl)-trimethylammonium bromide. Then, the ionic liquid compound with the desired anion is synthesized by the metathesis reaction.

Scheme 17

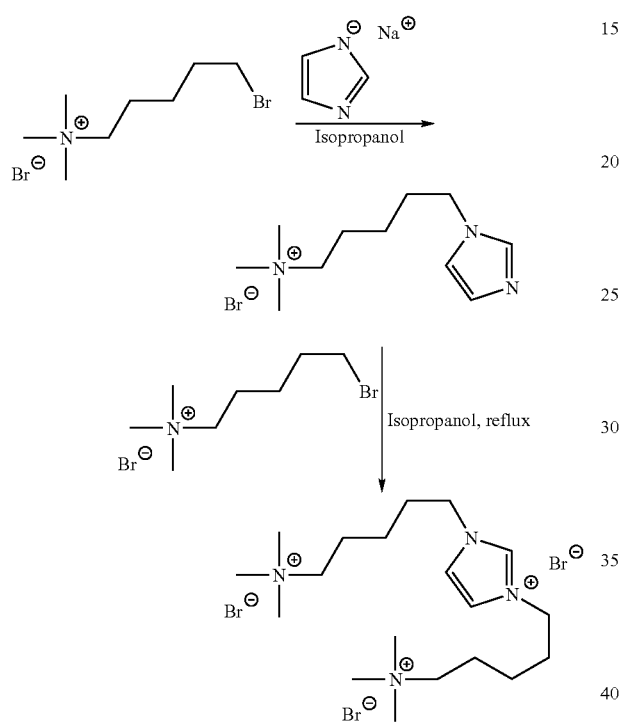

Example 18

Synthesis of a Linear Unsymmetrical Trigeminal Tricationic Liquid Salt

As shown in Scheme 8, an unsymmetrical tricationic compound is synthesized by similar synthetic procedures as described above.

Scheme 18

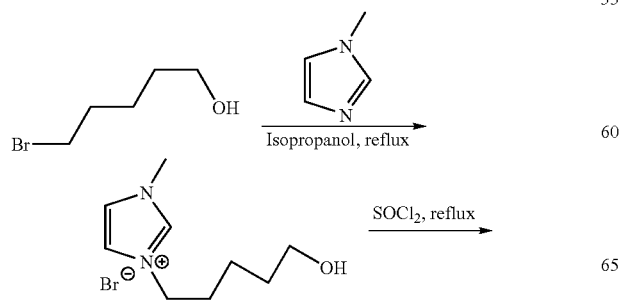

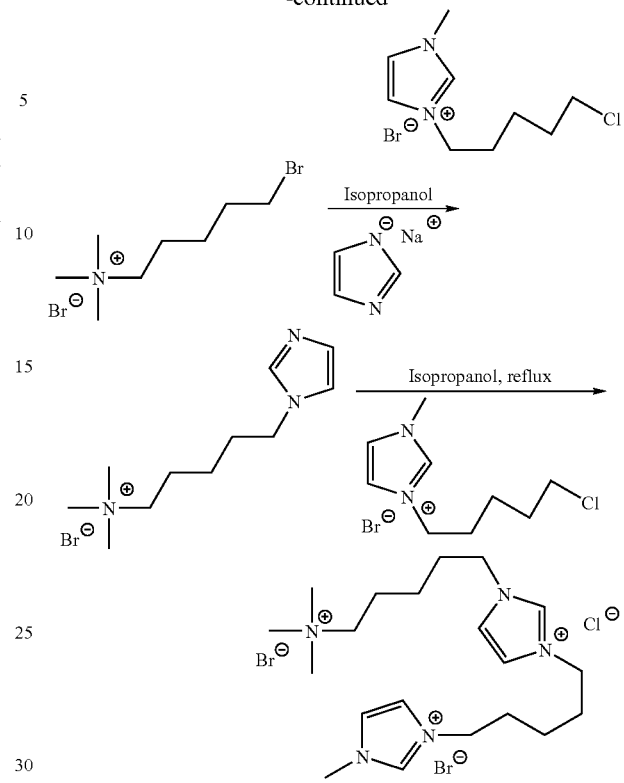

Example 19

Synthesis of a Linear Tetrageminal Tetracationic Liquid Salt

As shown in Scheme 19, the linear tetracationic compound with bromide is obtained by refluxing alkyldiimidazole and (5-bromopentyl)-trimethylammonium bromide in isopropanol. Then, the ionic liquid compound with the desired anion is synthesized by the metathesis reaction.

Scheme 19

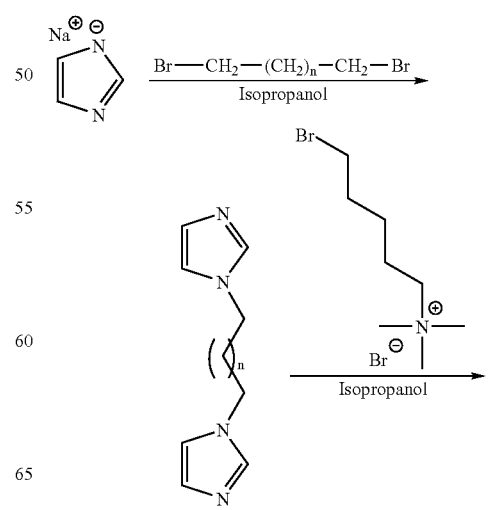

-continued

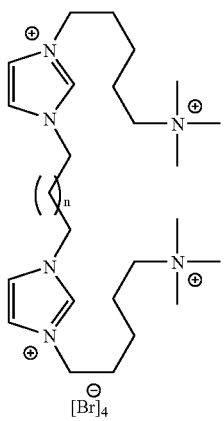

Example 20

Use of Polycationic Liquid Salts as Reagents in ESI-MS for the Detection of Anionic Molecules Tricationic Reagent:

Table 1 gives the structure of the seventeen cationic reagents used in this study.

After purification, the tricationic salts were exchanged to the fluoride form using the procedure reported previously with some modifications. The same amount (4 mL) of anion exchange resin was packed into a disposable 10 mL syringe and put into the fluoride form by washing the column with ten column volumes of 1 M NaOH followed by ten column volumes of water, seven volumes of 0.5 M NaF, and ten volumes of water. The tricationic reagents were dissolved in either water or methanol at a concentration of 0.05M and one milliliter of this solution was passed through the resin and eluted by water into a volumetric flask. This stock solution was diluted with water to make the working tricationic reagent solution at concentration such that when it was mixed with the carrier solvent the concentration of the reagent was 10 µM.

ESI-MS:

ESI-MS analysis was carried out on a LXQ (Thermo Fisher Scientific San Jose, Calif., USA) linear ion trap. A Surveyor MS pump (Thermo Fisher Scientific) with a vacuum degasser provided the carrier flow (67% MeOH/33% Water) at 300 µL/min. The tricationic reagent was introduced to carrier flow using a Y-type tee and a Shimadzu 6A LC pump operated at 100 µL/min was used for this purpose. For analysis in negative mode water replaced the aqueous tricationic reagent solution. The test anions were introduced into the carrier solvent using a six-port injection valve located between the Surveyor MS pump and the Y-type tee. ESI ionization conditions for

TABLE 1

| Trications | Core | Charged Groups |
|---|---|---|
| A1<br>A2<br>A5<br>A6<br>B1<br>B2<br>B4<br>B6<br>C1<br>C2<br>C3<br>C4<br>C5<br>C6<br>C7<br>D2<br>D6 | A, B, C, D structures | 1) R = imidazolium-butyl<br>2) R = imidazolium-methyl<br>3) R = imidazolium-CH2OH<br>4) R = imidazolium-phenyl<br>5) R = pyrrolidinium-propyl<br>6) R = tributylphosphonium<br>7) R = quinolizidine | positive and negative ion modes along with the optimized parameters for fluorophosphates are listed in Table 2.

TABLE 2

| | MS parameters | | |
|---|---|---|---|
| MS Parameters | General Positive Mode | General Negative Mode | Optimized for FPO$_3$ |
| Spray Voltage (kV) | 3 | −5 | 4.7 |
| Capillary temp (° C.) | 350 | 250 | 350 |
| Capillary Voltage (V) | 11 | 28 | −21 |
| Tube lens (V) | 105 | 95 | −96 |
| Sheath gas (AU) | 37 | 37 | 37 |
| Auxiliary gas (AU) | 6 | 6 | 6 |

(AU): arbitrary units

Detection limits (defined as S/N=3) for the eleven anions were determined by five replicate injections. The mass spectrometer was operated in single ion monitoring mode for the determination of all limits of detection (LODs). Data analysis was performed in Xcalibur 3.1 software.

prusside, and hexachloroplatinate were among the inorganic anions included. Some of the anions were chosen based on the behavior of singly charged anions with dicationic reagents. Singly charged anions with halogen atoms paired very well with dicationic reagents and so representative divalent anions with bromine or fluorine atoms (bromosuccinate, dibromosuccinate, fluorophosphates) also were included in this study.

The trications synthesized for this study had one of four different "core" structures (Table 1). A and B have a benzene core while the nitrogen at the middle of core C is less hydrophobic. D is by far the most flexible of the four core structures. Seven different charge carrying groups were used to create the seventeen tricationic reagents. Trications are named by the core used (A, B, or C) and the type of charged group (1-7). For example, trication A1 has the benzene core and butyl imidazolium charged groups.

The detection limits for the anions in the positive mode by ESI-MS are in Table 2.

TABLE 2

| Detection limits of doubly charged anions with tricationic reagents | | | | | | | |
|---|---|---|---|---|---|---|---|
| Sulfate | | Dichromate | | Oxalate | | Thiosulfate | |
| Trication | LOD (ng) | Trication | LOD (ng) | Trication | LOD (ng) | Trication | LOD (ng) |
| B1 | 1.00E−01 | B1 | 4.58E−01 | C6 | 1.50E−02 | A6 | 1.25E−01 |
| B4 | 1.00E−01 | B4 | 2.00E+00 | A1 | 4.00E−02 | C1 | 1.25E−01 |
| A5 | 1.00E−01 | A6 | 1.00E+01 | B1 | 4.00E−02 | B2 | 1.50E−01 |
| C3 | 1.25E−01 | C4 | 1.00E+01 | B6 | 2.34E−01 | C5 | 1.53E−01 |
| D6 | 1.50E−01 | B2 | 1.00E+01 | A6 | 2.50E−01 | B4 | 1.61E−01 |
| C4 | 2.50E−01 | A1 | 1.02E+01 | C1 | 3.43E−01 | C4 | 2.00E−01 |
| B2 | 2.50E−01 | A2 | 1.25E+01 | C3 | 3.75E−01 | B1 | 2.41E−01 |
| A1 | 5.00E−01 | B6 | 1.49E+01 | C4 | 4.35E−01 | B6 | 2.60E−01 |
| A6 | 5.00E−01 | C2 | 1.73E+01 | A2 | 4.99E−01 | C6 | 4.50E−01 |
| A2 | 6.25E−01 | C1 | 1.75E+01 | A5 | 5.00E−01 | C3 | 4.99E−01 |
| D2 | 7.00E−01 | C3 | 2.00E+01 | B2 | 5.00E−01 | A2 | 7.50E−01 |
| C2 | 7.50E−01 | C5 | 2.50E+01 | C2 | 7.18E−01 | C2 | 7.80E−01 |
| C1 | 8.75E−01 | C6 | 4.50E+01 | B4 | 7.50E−01 | A1 | 1.00E+00 |
| B6 | 1.50E+00 | D6 | 4.88E+01 | D6 | 8.75E−01 | D2 | 1.38E+00 |
| C5 | 1.88E+00 | C7 | 4.96E+01 | C5 | 1.00E+00 | A5 | 2.14E+00 |
| C6 | 2.38E+00 | A5 | 1.75E+02 | D2 | 1.50E+00 | C7 | 5.20E+00 |
| C7 | 2.75E+00 | D2 | 2.50E+02 | C7 | 4.28E+00 | D6 | 1.50E+01 |
| Nitroprusside | | Bromosuccinate | | o-benzenedisulfonate | | Hexachloroplatinate | |
| Trication | LOD (ng) | Trication | LOD (ng) | Trication | LOD (ng) | Trication | LOD (ng) |
| B4 | 3.22E−03 | A6 | 7.50E−02 | A6 | 1.50E−02 | B4 | 2.60E−02 |
| A6 | 7.50E−03 | B6 | 4.99E−01 | C1 | 2.25E−02 | B1 | 3.90E−02 |
| B1 | 8.55E−03 | C3 | 5.00E−01 | B1 | 2.50E−02 | A6 | 7.50E−02 |
| B6 | 1.38E−02 | D6 | 5.00E−01 | B4 | 2.50E−02 | C1 | 1.00E−01 |
| C4 | 2.00E−02 | C6 | 7.50E−01 | C4 | 3.00E−02 | A1 | 1.30E−01 |
| C1 | 2.73E−02 | A5 | 1.50E+00 | C6 | 3.75E−02 | B6 | 1.58E−01 |
| C5 | 2.73E−02 | C5 | 1.63E+00 | A1 | 5.00E−02 | B2 | 2.00E−01 |
| C3 | 4.25E−02 | A2 | 4.99E+00 | C2 | 5.00E−02 | C4 | 2.50E−01 |
| A1 | 4.29E−02 | C1 | 5.00E+00 | B6 | 5.00E−02 | D6 | 5.00E−01 |
| C2 | 4.42E−02 | B2 | 5.00E+00 | C5 | 5.00E−02 | C5 | 8.75E−01 |
| A2 | 4.86E−02 | C2 | 7.00E+00 | A2 | 7.50E−02 | C3 | 1.00E+00 |
| C7 | 6.00E−02 | A1 | 7.50E+00 | C3 | 1.25E−01 | C2 | 1.05E+00 |
| B2 | 1.00E−01 | C4 | 8.75E+00 | D6 | 1.50E−01 | A2 | 1.58E+00 |
| D6 | 1.25E−01 | B4 | 1.00E+01 | A5 | 2.00E−01 | C7 | 1.58E+00 |
| C6 | 2.00E−01 | D2 | 1.25E+01 | C7 | 3.75E−01 | C6 | 2.00E+00 |
| A5 | 3.15E−01 | B1 | 1.75E+01 | B2 | 1.13E+00 | D2 | 2.13E+00 |
| D2 | 8.75E−01 | C7 | 4.50E+01 | D2 | 1.75E+00 | A5 | 2.25E+00 |

Results and Discussion:

Eleven divalent anions were used to evaluate seventeen different tricationic reagents (see Table 1). The anions included both inorganic and organic types and were structurally diverse. Metal-based anions such as dichromate, nitro- Except for dichromate, detection limits for most of the anions were in the hundreds of picograms to nanogram range with the tricationic reagents. The trications are arranged from lowest to highest according to the determined LODs. Using this arrangement, there are a few trends that emerge. From Table 2 it becomes obvious that trications A6 and B1 provide good sensitivity for a broad range of the representative divalent anions. A6 (1,3,5-tris-(tripropylphosphonium) methylbenzene trifluoride) performs the best overall since it ranks as one of the top three tricationic reagents for all of the anions except sulfate and oxalate. Even then, it ranks as the fifth best tricationic reagent for detecting oxalate. Trication B1 (1,3,5-tris-(1-(3-butylimidazolium)) methyl-2,4,6-trimethylbenzene trifluoride) also does well, but is in the top three less consistently than A6. Table 2 also shows that trication C7 does not pair well with any anion, making it the most ineffective additive tested. A5 also ranked in the lower half of the trication list for many of the anions. These two tricationic reagents would be poor choices for developing a sensitive method for the detection of divalent anions by positive ion mode ESI-MS.

When the terminal cationic moieties of the trication are the same, it is possible to compare the effect of the core structure on the performance of the tricationic reagent. While there are exceptions, cores A and B tend to pair more effectively with the doubly charged anions than those based on core C. For these eleven anions, a tricationic reagent with a C core performs in the top three only four times. Thus, a tricationic reagent with a more rigid aromatic core seems to produce better results. However, the decision whether or not to include methyl groups as substituents on the benzene core is less straightforward. When the charged group is phosphorus-based, the plain benzene core (A1) provided lower detection limits compared to the mesitylene (1,3,5-trimethylbenzene) core (B6). However, the opposite trend was seen in comparing A1 and B1. A1 seemed to be more susceptible to the loss of one of the butyl imidazole groups under MS conditions (data not shown) than B1, which appears to be stabilized by the methyl groups on the mesitylene core. It should also be noted that these cores may have limited flexibility due to the repulsion among their identically charged moieties. Flexibility of the pairing agent was found to be an important factor in the pairing of singly charged anions with dicationic reagents. Trications D2 and D6 are more flexible due to their longer chains. However, these trications do not provide good sensitivity for any divalent anions except fluorophosphates. This core structure has several heteroatoms and carbonyl groups which could compromise its effectiveness as a gas phase ion pairing agent that can provide good detection limits. It seems that a more ideal tricationic core would use longer (perhaps solely) hydrocarbon chains to attach the charged groups to a hydrophobic core. This would reduce charge repulsion and increase flexibility.

The nature of the terminal charged groups also influenced the detection limits observed for the anions. For example, the phosphonium based tricationic reagents (A6, B6, and C6) generally paired well with all of the anions. Benzyl imidazolium groups provided the lowest detection limits for nitroprusside and hexachloroplatinate and decent detection limits for o-benzenedisulfonate. This seems to indicate that pi-pi and n-pi interactions play a role in the association of certain specific anions with tricationic reagents. Analogous trends were seen with dicationic reagents. However, two of the charged groups that did well with the dicationic reagents gave lower than expected sensitivities for the representative anions in this study. Reagents with methyl imidazolium and pyrrolidinium groups consistently placed in the middle to lower half of the trications tested regardless of the core structure. Instead, butyl imidazolium groups on the mesitylene core (B) performed better than expected.

It should be noted that the empirical data presented here are the result of several factors in addition to the binding affinity of the anions to the tricationic reagent. A single set of instrumental settings was used for the evaluation of the tricationic reagents. Some variance in instrumental performance between the different complexes is to be expected. The detection limit for oxalate was lowered from 250 pg to 75 pg when conditions were completely optimized (see experimental) for the oxalate/A6 complex. This increase in sensitivity is similar to that seen when optimizing dicationic reagents for detecting singly charged anions. Increasing the spray voltage and decreasing the capillary temperature had the biggest impact on the signal intensity.

Figure 3:
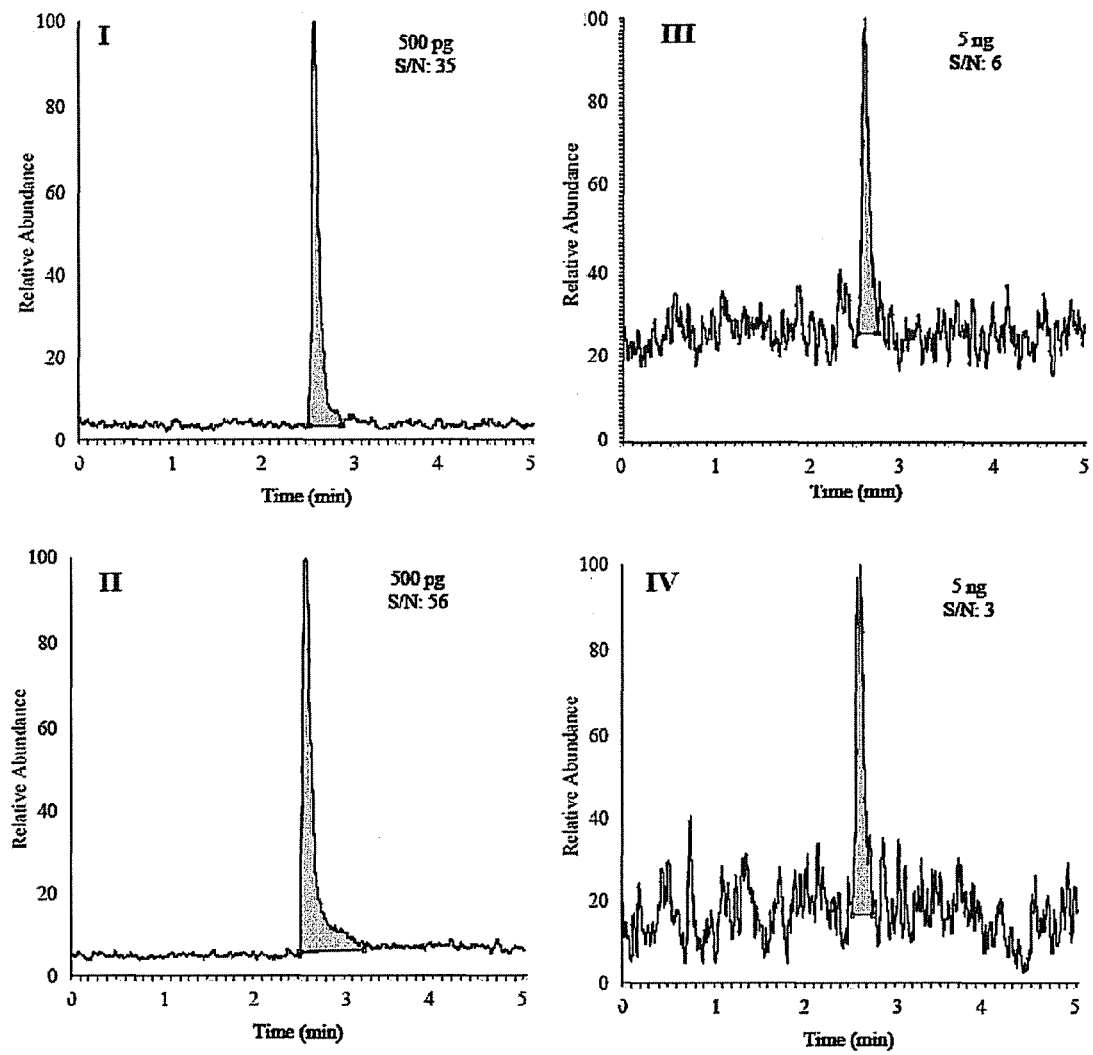
FIG. 3 is graphical representation comparing the signal to noise ratios in the positive (I, II) and negative (III, IV) ion modes for the two anions, hexachloroplatinate and o-benzenedisulfonate. Tricationic reagents A6 (I) and B1 (II) in water were introduced into the carrier flow after anion injection in positive ion mode while only water was used in negative ion mode (III, IV).

FIG. 3 shows a comparison of signal to noise ratios in the positive and negative ion modes for the two anions hexachloroplatinate and 0-benzenedisulfonate. In both cases, using a tricationic reagent in the positive mode produced superior signal to noise ratios even though ten times less sample was injected. By detecting divalent anions in the positive mode as a complex, the sensitivity for the two anions increases by almost two orders of magnitude. This demonstrates the ability of tricationic reagents to improve the sensitivity of mass spectrometry for divalent anions.

CONCLUSIONS

Seventeen tricationic reagents have been evaluated as pairing agents for detecting eleven doubly charged anions in the positive mode by ESI-MS. Structural features of the tricationic reagents including the terminal charged groups and the core structure influenced the detection limits for the doubly charged anions. The use of tricationic reagents in the positive ion mode increased the signal to noise ratios of hexachloroplatinate and O-benzenedisulfonate compared to negative mode even though ten times more sample was injected in the negative ion mode.

REFERENCES

1. Welton, T. *Chem. Rev.* 1999, 99, 2071-2083.
2. Cadena, C.; Anthony, J. L.; Shah, J. K.; Morrow, T. I.; Brennecke, J. F.; Maginn, E. J. *J. Am. Chem. Soc.* 2004, 126, 5300-5308.
3. Visser, A. E.; Swatioski, R. P.; Reichert, W. M.; Mayton, R Sheff, S.; Wierzbicki, A.; Davis, J. H.; Rogers, R. D. *Environ. Sci. Technol.* 2002, 36, 2523-2529.
4. Anderson, J. L.; Armstrong, D. W., *Anal. Chem.* 2003, 75, 4851-4858.
5. Anderson, J. L.; Pino, V.; Hagberg, E. C.; Sheares, V. V.; Armstrong, D. W., *Chem. Commun.* 2003, 2444-2445.
6. Fletcher, K. A.; Pandey, S. *Langmuir* 2004, 20, 33-36.
7. Zhou, Y.; Antonietti, M., *J. Am. Chem. Soc.* 2003, 125, 14960-14961.
8. Luo, H.; Dai, S.; Bonnesen, P. V.; Buchanan, A. C.; Holbrey, J. D.; Bridges; N. J.; Rogers, R. D. *Anal Chem.* In press.
9. Wu, J.; Zhang, J.; Zhang, H.; He, J.; Ren, Q.; Guo, M., *Biomacromolecules* 2004, 5, 266-268.
10. Vijayaraghavan, R.; MacFarlane, D. R., *Chem. Commun.* 2004, 700-701.
11. Boxall, D. L.; Osteryoung, R. A., *J. Electrochem. Soc.* 2004, 151, E41-E45
12. Earle, M. J.; Katdare, S. P.; Seddon, K. R., *Org. Lett.* 2004, 6, 707-710.
13. Carter, E. B.; Culver, S. L.; Fox, P. A.; Goode, R. D.; Ntai, I.; Tickell, M. D.; Traylor, R. K.; Hoffman, N. W.; Davis, J. H. *Chem. Commun.* 2004, 630-631.
14. Wasserscheid, P.; Hilgers, C.; Keim, W., *Journal of Molecular Catalysis A* 2004, 214, 83-90.

15. Gao, H.; Jiang, T.; Han, B.; Wang, Y.; Du, J.; Liu, Z.; Zhang, J., *Polymer* 2004, 45, 3017-3019.
16. Kaar, J. L.; Jesionowski, A. M.; Berberich, J. A.; Moulton, R.; Russell, A. J., *J. Am. Chem. Soc.* 2003, 125, 4125-4131.
17. Zhao, H.; Malhotra, S. V *Biotechnology Letters* 2002, 24, 1257-1260.
18. Lee, J. K.; Kim, M-J., *J. Org. Chem.* 2002, 67, 6845-6847.
19. Wilkes, J. S., *Journal of Molecular Catalysis A: Chemical* 2004, 214, 11-17.
20. Bonhote, P.; Dias, A.-P.; Papageorgiou, N.; Kalyanasundaram, K.; Gratzel, M. *Inorg Chem.* 1996, 35, 1168.
21. Wei, G-T.; Yang, Z.; Lee, C-Y.; Yang, H-Y.; Wang, C. R., *J. Am. Chem. Soc.* 2004, 126, 5036-5037.
22. Itoh, H.; Naka, K.; Chujo, Y., *J. Am. Chem. Soc.* 2004, 126, 3026-3027.
23. Katritzky, A. R.; Jain, R.; Lomaka, A.; Petrukhin, R.; Karelson, M.; Visser, A. E.; Rogers, R. D, *J. Chem. Inf Comput. Sci.* 2002, 42, 225-231.
24. Eike, D.; Brennecke, J. F.; Maginn, E. J., *Green Chem.* 2003, 5, 323.
25. Forsyth, S. A.; Pringle, J. M.; MacFarlane, D. R., *Aust. J. Chem.* 2004, 57, 113-119.
26. Dzyuba, S. V.; Bartsch, R. A., *Chem. Phys. Phys. Chem.* 2002, 3, 161-166.
27. Seddon, K. R.; Stark, A.; Torres, M-J., ACS Symposium Series 2002, 819 (Clean Solvents: Alternative Media for Chemical Reactions and Processing), 34-49.
28. Carda-Brach, S.; Berthod, A.; Armstrong, D. W., *Anal. Bioanal. Chem.* 2003, 375, 191.
29. Baranyai, K. J.; Deacon, G. B.; MacFarlane, D. R.; Pringle, J. M.; Scott, J. L., *Aust. J. Chem.* 2004, 57, 145-147.
30. Van Valkenburg, M. E.; Vaughn, R. L.; Williams, M.; Wilkes, J. S. Proceedings—Electrochemical Society 2002, 2002-19 (Molten Salts XIII), 112-123.
31. Anderson, J. L.; Ding, J.; Welton, T.; Armstrong, D. W., *J. Am. Chem. Soc.* 2002, 124, 14247-14254.
32. Blessing, R. H., *Acta Cryst.* 1995, AS1, 33-38.
33. All software and sources of the scattering factors are contained in the SHELXTL (version 5.1) program library (G. Sheldrick, Bruker Analytical X-Ray Systems, Madison, Wis.).
34. Law, G.; Watson, P. R., *Langmuir* 2001, 17, 6138-6141.
35. Ngo, H. L.; LeCompte, K.; Hargens, L.; McEwen, A. B., *Thermochimica Acta* 2000, 357-358, 97-102.
36. Hu, X.; Tang, Y.; Gantzel, P.; Meyer, K., *Organometallics* 2003, 22, 612-614.
37. Bryce, M. R., *Chem. Soc. Rev.* 1991, 20, 355-390.
38. Holbrey, J. D.; Reichert, W. M.; Nieuwenhuyzen, M.; Johnston, S.; Seddon, K. R.; Rogers, R. D., *Chem. Commun.* 2003, 1636-1637.
39. Dearden, J. C., *Sci. Total Environ.* 1991, 59, 109-110.
40. Bondi, A.-J., *J. Phys. Chem.* 1964, 68, 441-453.
41. Anderson, J. L.; Ding, R.; Ellem, A.; Armstrong, D. W. *J. Am. Chem. Sac.* 2005, 127, 593-604.
42. Terazima, M.; Nogami, Y.; Tominaga, T. *Chemical Physical Letters* 2000, 332, 503-507.
43. Van Hook, J. P.; Tobolsky, A V. *J. Am. Chem. Soc.* 1958, 80, 779-782.
44. Anderson, J. L.; Ding, J.; Welton, T.; Armstrong, D. W. J. Am. Chem. Soc. 2002, 124, 14247-14254.
45. Abraham, M. H. *Chem. Soc. Rev.* 1993, 22, 73.
46. Abraham, M. H.; Whiting, G. S.; Doherty, R. M.; Shuely, W. J. *J Chomatogr.* 1991, 587, 229-236.
47. Bouche, J.; Verzele, M. *J Gas Chromatogr.* 1968, 6, 501.
48. Muldoon, M. J.; Gordon, C. M. J *Polym. Sci. Part A: Polym. Chem.* 2004, 42, 3865-3869.
49. Marcilla, R.; Blazquez, J. A.; Rodriguez, J.; Pomposo, J. A.; Mecerreyes, D. J *Polym. Sci. Part A: Polym. Chem.* 2004, 42, 208-212.
50. Armstrong, D. W.; He, L.; Liu, L.-S. *Anal. Chem.* 1999, 71, 3873-3876
51. Anderson, J. L.; Armstrong, D. W. *Anal. Chem.* 2003, 75, 4851-4858.
52. Lord & Pawliszym, *J. Chromatogr.* A 885 (2000) 153-193.
53. Visser et al. "Task-Specific Ionic Liquids Incorporation Novel Cations for the Coordination and Extraction of $Hg^{2+}$ and $Cd^{2+}$: Synthesis, Characterization, and Extraction Studies," *Environ. Sci. Technol.* (2002) 36, 2523-29.
54. Liu et al. "Disposable ionic liquid coating for headspace solid-phase microextraction of benzene, toluene, ethyl benzene, and xylenes in plants followed by gas chromatography-flame ionization detection," *J. Chromatogr.* A (2005), 1066 (1-2), 27-32.
55. Vas, G.; Vekey, K., J. Mass Spectrometery (2004) 39, 233-254.
56. Han et al., 2005 "Using Geminal Dicationic Ionic Liquids as Solvents for High-Temperature Organic Reactions," *Org. Lett.* 7: 4205-4208.
57. Pemak et al., 2007, "Synthesis and Properties of Trigeminal Tricationic Ionic Liquids", *Chem. Eur. J.* 00:0-0.
58. Jin et al., 2006, "Polyethylene glycol functionalized dicationic ionic liquids with alkyl or polyfluoroalkyl substituents as high temperature 'Lubricants" *J. Mater. Chem.* 16:1529-1535.
59. Martinelango et al., 2005, "Gas-Phase Ion Association Provides Increased Selectivity and Sensitivity for Measuring Perchlorate by Mass Spectrometry" *Anal. Chem.* 2005, 77, 4829-4835.
60. K. Grob, G. Grob and K. Grob, *I. Chromatogr.* 156: 1 (1978).
61. K. Grob, G. Grob and K. Grob, *J. Chromatogr.* 219: 13 (1981).

What is claimed is:

1. A triionic liquid salt comprising a triionic species, wherein the triionic species corresponds in structure to:

and at least one counterion;

wherein each R, $R_1$, $R_2$, $R_3$ and $R_n$ are independently selected from the group consisting of hydrogen, alkyl, hydroxyalkyl, carbocyclyl, heterocyclyl, halo, alkoxy and hydroxy;

and each $R_c$ is independently selected from the group consisting of alkyl, cycloalkyl, phenyl, halo, alkoxy and hydroxyl.

2. The triionic liquid salt of claim 1, wherein the at least one counterion is selected from the group consisting of halogen, $BF_4^-$, $PF_6^-$, $NTf_2^-$, $TfO^-$,

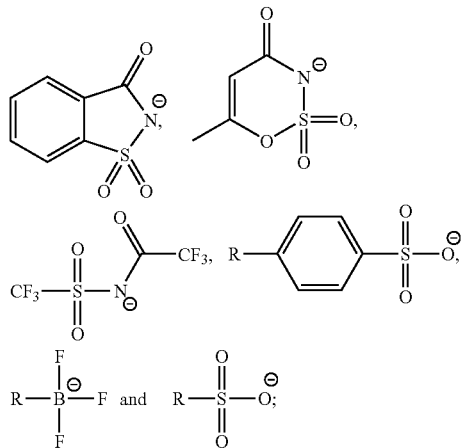

wherein R is selected from the group consisting of hydrogen, alkyl, hydroxyalkyl, carbocyclyl, heterocyclyl, halo, alkoxy, hydroxyl, alkylcarbonyl, alkylcarbonylalkylene, hydroxycarbonyl,

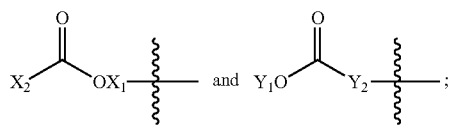

wherein
$X_1$ is $C_1$-$C_{10}$-alkylene;
$X_2$ is selected from the group consisting of hydrogen, alkyl, alkoxy, amino and hydroxy;
$Y_1$ is selected from the group consisting of hydrogen and alkyl; and
$Y_2$ is $C_1$-$C_{10}$-alkylene.

3. A tetraionic liquid salt comprising a tetraionic species that corresponds in structure to:

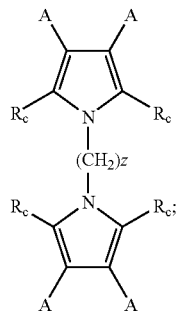

wherein Rc is a substituent independently selected from the group consisting of alkyl, cycloalkyl, phenyl, halo, alkoxy and hydroxyl;
each A is an independently selected monoionic group, wherein:
the monoionic group is selected from the group consisting of alkylene, alkenylene, alkynylene, (—$CH_2$-carbocyclyl-$CH_2$—)$_n$, and polysiloxyl; wherein alkylene, alkenylene, and alkynylene optionally contain one or more heteroatoms selected from the group consisting of O, N, S and Si;

wherein the monoionic group is substituted with a cationic group selected from the group consisting of heterocyclyl, ammonium and phosphonium; wherein the cationic group optionally is substituted with one or more substituents independently selected from the group consisting of alkyl, cycloalkyl, phenyl, halo, alkoxy and hydroxyl; wherein the alkyl optionally is substituted with one or more substituents selected from the group consisting of hydroxy and phenyl; or the monoionic group is an anionic group selected from the group of substituents consisting of carboxylate, sulfonate and sulfate; wherein each such substituent is optionally substituted with one or more substituents independently selected from the group consisting of alkyl, carbocyclyl and heterocyclyl;

n is selected from the group consisting of 1 to 20, inclusive; and wherein z is selected from the group consisting of 1 to 20, inclusive.

4. The tetraionic liquid salt of claim 3, wherein the polyionic species corresponds in structure to:

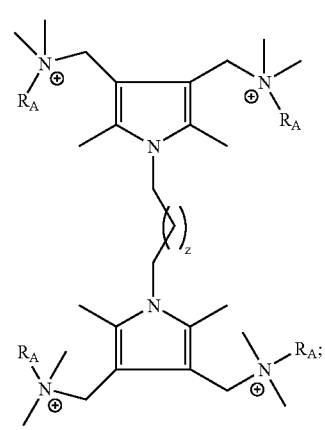

wherein each $R_A$ is independently selected from the group consisting of hydrogen, alkyl, cycloalkyl, phenyl, halo, alkoxy and hydroxyl;
wherein z is selected from the group consisting of 1 to 20, inclusive.

5. The tetraionic liquid salt of claim 4, wherein the at least one counterion is selected from the group consisting of halogen, $BF_4^-$, $PF_6^-$, $NTf_2^-$, $TfO^-$,

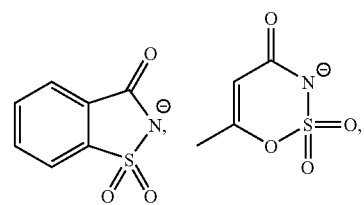

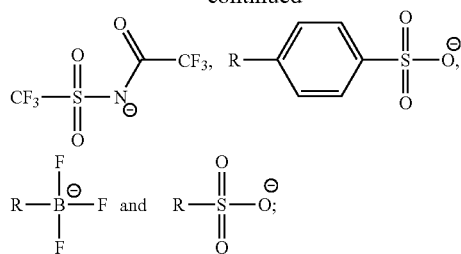

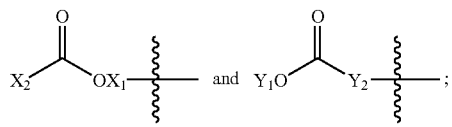

wherein R is selected from the group consisting of hydrogen, alkyl, hydroxyalkyl, carbocyclyl, heterocyclyl, halo, alkoxy, hydroxyl, alkylcarbonyl, alkylcarbonylalkylene, hydroxycarbonyl,

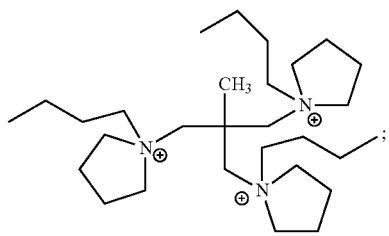

wherein $X_1$ is $C_1$-$C_{10}$-alkylene;

$X_2$ is selected from the group consisting of hydrogen, alkyl, alkoxy, amino and hydroxy;

$Y_1$ is selected from the group consisting of hydrogen and alkyl; and $Y_2$ is $C_1$-$C_{10}$-alkylene.

6. The tetraionic liquid salt of claim 5, wherein there are at least four counterions.

7. A triionic liquid salt comprising a triionic species, wherein the triionic species corresponds in structure to

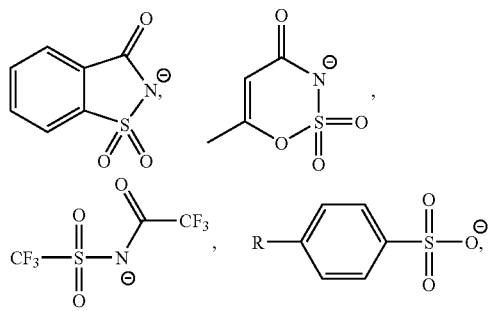

and at least one counterion.

8. The triionic liquid salt of claim 7, wherein the at least one counterion is selected from the group consisting of halogen, $BF_4^-$, $PF_6^-$, $NTf_2^-$, $TfO^-$,

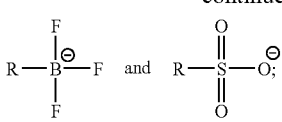

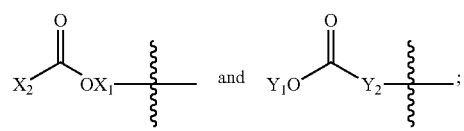

wherein R is selected from the group consisting of hydrogen, alkyl, hydroxyalkyl, carbocyclyl, heterocyclyl, halo, alkoxy, hydroxyl, alkylcarbonyl, alkylcarbonylalkylene, hydroxycarbonyl,

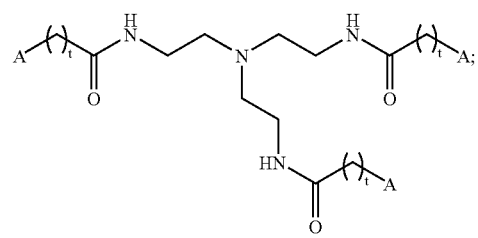

wherein $X_1$ is $C_1$-$C_{10}$-alkylene;

$X_2$ is selected from the group consisting of hydrogen, alkyl, alkoxy, amino and hydroxy;

$Y_1$ is selected from the group consisting of hydrogen and alkyl; and $Y_2$ is $C_1$-$C_{10}$-alkylene.

9. A triionic liquid salt comprising a triionic species which corresponds in structure to:

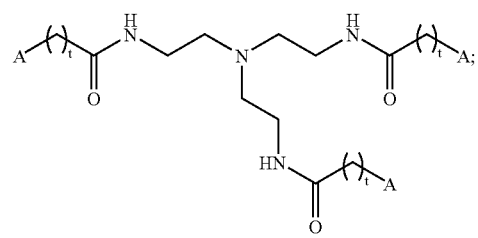

and at least one counterion;

wherein each t is independently selected from the group consisting of 1 to 20, inclusive; wherein each A is an independently selected monoionic group, wherein:

the monoionic group is selected from the group consisting of alkylene, alkenylene, alkynylene, (—$CH_2$-carbocyclyl-$CH_2$—)$_n$, and polysiloxyl; wherein alkylene, alkenylene, and alkynylene optionally contain one or more heteroatoms selected from the group consisting of O, N, S and Si;

wherein the monoionic group is substituted with a cationic group selected from the group consisting of heterocyclyl, ammonium and phosphonium; wherein the cationic group optionally is substituted with one or more substituents independently selected from the group consisting of alkyl, carbocyclyl, heterocyclyl, halo, alkoxy and hydroxyl;

wherein the alkyl optionally is substituted with one or more substituents selected from the group consisting of hydroxy and phenyl.

10. The triionic liquid salt of claim 9, wherein the triionic species corresponds in structure to a formula selected from the group consisting of:

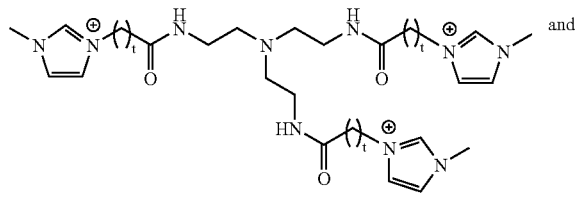 and

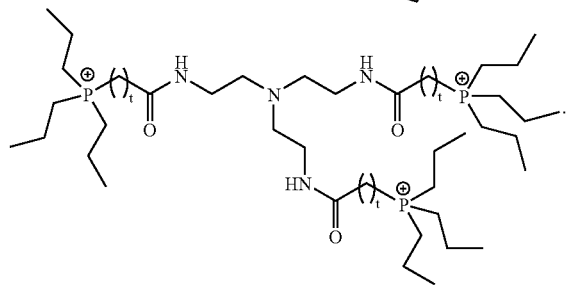

11. The triionic liquid salt of claim 10, wherein the at least one counterion is selected from the group consisting of halogen, $BF_4^-$, $PF_6^-$, $NTf_2^-$, $TfO^-$,

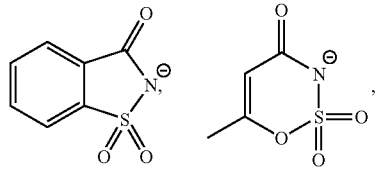

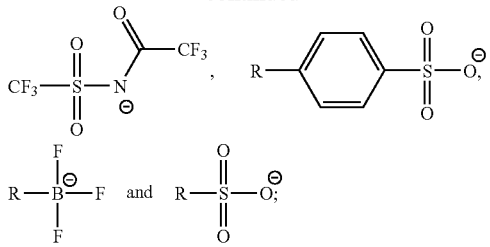

wherein R is selected from the group consisting of hydrogen, alkyl, hydroxyalkyl, carbocyclyl, heterocyclyl, halo, alkoxy, hydroxyl, alkylcarbonyl, alkylcarbonylalkylene, hydroxycarbonyl,

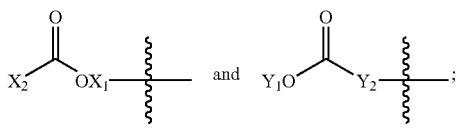

wherein
$X_1$ is $C_1$-$C_{10}$-alkylene;
$X_2$ is selected from the group consisting of hydrogen, alkyl, alkoxy, amino and hydroxy;
$Y_1$ is selected from the group consisting of hydrogen and alkyl; and
$Y_2$ is $C_1$-$C_{10}$-alkylene.

12. The triionic liquid salt of claim 10, wherein t is 5.

* * * * *